US012620478B2

(12) United States Patent
Takahashi et al.

(10) Patent No.: US 12,620,478 B2
(45) Date of Patent: May 5, 2026

(54) MEDICAL INFORMATION MANAGEMENT SYSTEM, MEDICAL INFORMATION MANAGEMENT METHOD, AND PROGRAM

(71) Applicant: FUJIFILM Corporation, Tokyo (JP)

(72) Inventors: Naoyuki Takahashi, Tokyo (JP); Masami Kitagawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 451 days.

(21) Appl. No.: 17/707,900

(22) Filed: Mar. 29, 2022

(65) Prior Publication Data

US 2022/0351844 A1 Nov. 3, 2022

(30) Foreign Application Priority Data

Apr. 30, 2021 (JP) ................................. 2021-077521

(51) Int. Cl.
*G16H 40/20* (2018.01)
*G16H 10/60* (2018.01)
(Continued)

(52) U.S. Cl.
CPC ............. *G16H 40/20* (2018.01); *G16H 10/60* (2018.01); *G16H 20/10* (2018.01); *G06F 3/0482* (2013.01); *G06F 3/0486* (2013.01)

(58) Field of Classification Search
CPC .. G06F 3/04847; G06F 3/0486; G06F 3/0482; G16H 20/10; G16H 40/20; G16H 15/00; G16H 40/63; G16H 10/60
(Continued)

(56) References Cited

U.S. PATENT DOCUMENTS

| | | | | |
|---|---|---|---|---|
| 2008/0086333 A1* | 4/2008 | Hertel | ................... | G06Q 10/10 |
| | | | | 705/2 |
| 2014/0172864 A1* | 6/2014 | Shum | ................ | G06F 17/30598 |
| 2017/0220748 A1* | 8/2017 | Okabe | ................... | G16H 30/40 |

FOREIGN PATENT DOCUMENTS

| | | | | | |
|---|---|---|---|---|---|
| CA | 2831300 A1 * | 3/2012 | ............. | G06Q 10/10 |
| JP | 2016024793 | 2/2016 | | |
| WO | WO-2014110280 A2 * | 7/2014 | ........... | G06F 3/0481 |

OTHER PUBLICATIONS

Author(s): Bendixen Title: Interactive tools for inpatient medication tracking Journal: Jamia [online]. Publication date: 2016.[retrieved on: Jun. 29, 2024 ]. Retrieved from the Internet: <URL:https://academic.oup.com/jamia/article/23/1/144/2380197> (Year: 2016).*

(Continued)

*Primary Examiner* — Igor N Borissov
(74) *Attorney, Agent, or Firm* — JCIPRNET

(57) ABSTRACT
A medical information management system comprises a processor configured to display a display field having a biological information display field where biological information of a target patient is displayed along a time axis and an administration information display field where administration information is displayed, and an input list where a plurality of medicine regions in correlation with combination information of a plurality of medicines and doses are arranged, receives an input of dragging a first region from the input list and dropping the first region to a second region of the display field, adds information indicating administration with a medicine and a dose correlated with the first region at a time corresponding to a position of a second region of the display field where the drop input is received, to updates the administration information, and updates the display of the administration information display field.

18 Claims, 40 Drawing Sheets

(51) Int. Cl.
  *G16H 20/10*        (2018.01)
  *G06F 3/0482*        (2013.01)
  *G06F 3/0486*        (2013.01)

(58) Field of Classification Search
  USPC ........................................................... 705/3
  See application file for complete search history.

(56)                    References Cited

OTHER PUBLICATIONS

Author(s): Engels Title: Prescriber knowledge and perceptions Journal: Sagepub [online]. Publication date: 2015.[retrieved on: Nov. 11, 2024 ]. Retrieved from the Internet: <URL:https://journals. sagepub.com/doi/pdf/10.1310/hpj5004-287> (Year: 2015).*

Author(s): Belden, J Title: Designing a medication timeline for patients and physicians Journal: Jamia [online]. Publication date: 2018.[retrieved on: Mar. 21, 2025 ]. Retrieved from the Internet: <URL:https://pubmed.ncbi.nlm.nih.gov/30590550/> (Year: 2018).*

* cited by examiner

| PALETTE | | | | | |
|---|---|---|---|---|---|
| O2 | L/min | 6 | 1 | 2 | 3 |
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg/ml | mg | 50 | 10 | 20 | 30 |
| ROCURONIUM 50 10 mg/ml | mg/h | 40 | 20 | 15 | 10 |
| FENTANYL 100 50 μg/ml | ug | 100 | 200 | 50 | 25 |
| ULTIVA 2 0.1 mg/ml | u/k/m | 0.2 | 0.25 | 0.5 | 0.1 |
| ULTIVA 2 0.1 mg/ml | mg/kg | | | 0.03 | 0.04 |
| EPHEDRINE 4 mg/ml | mg | | | 12 | |
| NEOSYNESIN 4 mg/ml | mg | | | 0.2 | |
| ATROPINE 0.5 mg/ml | mg | 0.5 | 0.25 | | |
| BRIDION 100 mg/ml | mg | 200 | 100 | | |
| FLUMAZENIL 0.1 mg/ml | mg | 0.2 | 0.3 | 0.1 | |
| NICARDIPINE 1 mg/ml | mg | 0.5 | 1 | 2 | |
| NICARDIPINE 1 mg/ml | mg/h | 2 | 3 | 4 | 10 |

Figure 7:
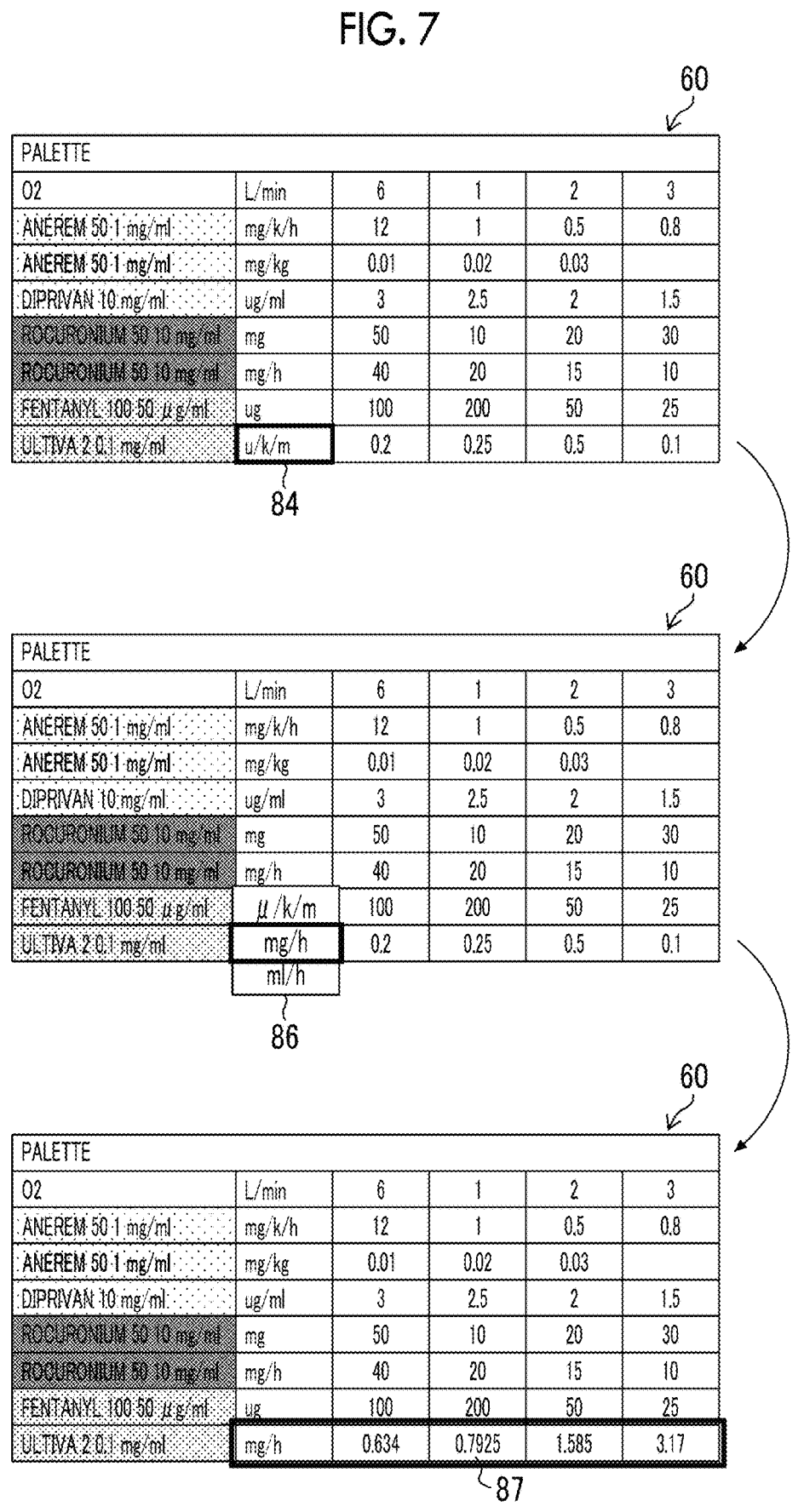

| PALETTE | | | | | |
|---|---|---|---|---|---|
| O2 | L/min | 6 | 1 | 2 | 3 |
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg/ml | mg | 50 | 10 | 20 | 30 |
| ROCURONIUM 50 10 mg/ml | mg/h | 40 | 20 | 15 | 10 |
| FENTANYL 100 50 μg/ml | ug | 100 | 200 | 50 | 25 |
| ULTIVA 2 0.1 mg/ml | u/k/m | 0.2 | 0.25 | 0.5 | 0.1 |

84

60

| PALETTE | | | | | |
|---|---|---|---|---|---|
| O2 | L/min | 6 | 1 | 2 | 3 |
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg/ml | mg | 50 | 10 | 20 | 30 |
| ROCURONIUM 50 10 mg/ml | mg/h | 40 | 20 | 15 | 10 |
| FENTANYL 100 50 μg/ml | μ/k/m | 100 | 200 | 50 | 25 |
| ULTIVA 2 0.1 mg/ml | mg/h | 0.2 | 0.25 | 0.5 | 0.1 |
| | ml/h | | | | |

86

60

| PALETTE | | | | | |
|---|---|---|---|---|---|
| O2 | L/min | 6 | 1 | 2 | 3 |
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg/ml | mg | 50 | 10 | 20 | 30 |
| ROCURONIUM 50 10 mg/ml | mg/h | 40 | 20 | 15 | 10 |
| FENTANYL 100 50 μg/ml | ug | 100 | 200 | 50 | 25 |
| ULTIVA 2 0.1 mg/ml | mg/h | 0.634 | 0.7925 | 1.585 | 3.17 |

| PALETTE | | | | | |
|---|---|---|---|---|---|
| O2 | L/min | 6 | 1 | 2 | 3 |
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg/ml | mg | 50 | 10 | 20 | 30 |
| ROCURONIUM 50 10 mg/ml | mg/h | 40 | 20 | 15 | 10 |
| FENTANYL 100 50 μg/ml | ug | 100 | 200 | 50 | 25 |
| ULTIVA 2 0.1 mg/ml | u/k/m | 0.2 | 0.25 | 0.5 | 0.1 |
| ULTIVA 2 0.1 mg/ml | mg/kg | 0.01 | 0.02 | 0.03 | 0.04 |
| EPHEDRINE 4 mg/ml | mg | 4 | 8 | 12 | |
| NEOSYNESIN 4 mg/ml | mg | 0.05 | 0.1 | 0.2 | |
| ATROPINE 0.5 mg/ml | mg | 0.5 | 0.25 | | |
| BRIDION 100 mg/ml | mg | 200 | 100 | | |
| FLUMAZENIL 0.1 mg/ml | mg | 0.2 | 0.3 | 0.1 | |
| NICARDIPINE 1 mg/ml | mg | 0.5 | 1 | 2 | |
| NICARDIPINE 1 mg/ml | mg/h | 2 | 3 | 4 | 10 |

| | | | | | |
|---|---|---|---|---|---|
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg/ml | mg | 50 | 10 | 20 | 30 |
| ROCURONIUM 50 10 mg/ml | mg/h | 40 | 20 | 15 | 10 |
| FENTANYL 100 50 μg/ml | ug | 100 | 200 | 50 | 25 |
| ULTIVA 2 0.1 mg/ml | u/k/m | 0.2 | 0.25 | 0.5 | 0.1 |
| ULTIVA 2 0.1 mg/ml | mg/kg | 0.01 | 0.02 | 0.03 | 0.04 |
| EPHEDRINE 4 mg/ml | mg | 4 | 8 | 12 | |
| NEOSYNESIN 4 mg/ml | mg | 0.05 | 0.1 | 0.2 | |
| ATROPINE 0.5 mg/ml | mg | 0.5 | 0.25 | | |

CONTINUOUS ADMINISTRATION

ONE-SHOT ADMINISTRATION

FIG. 11

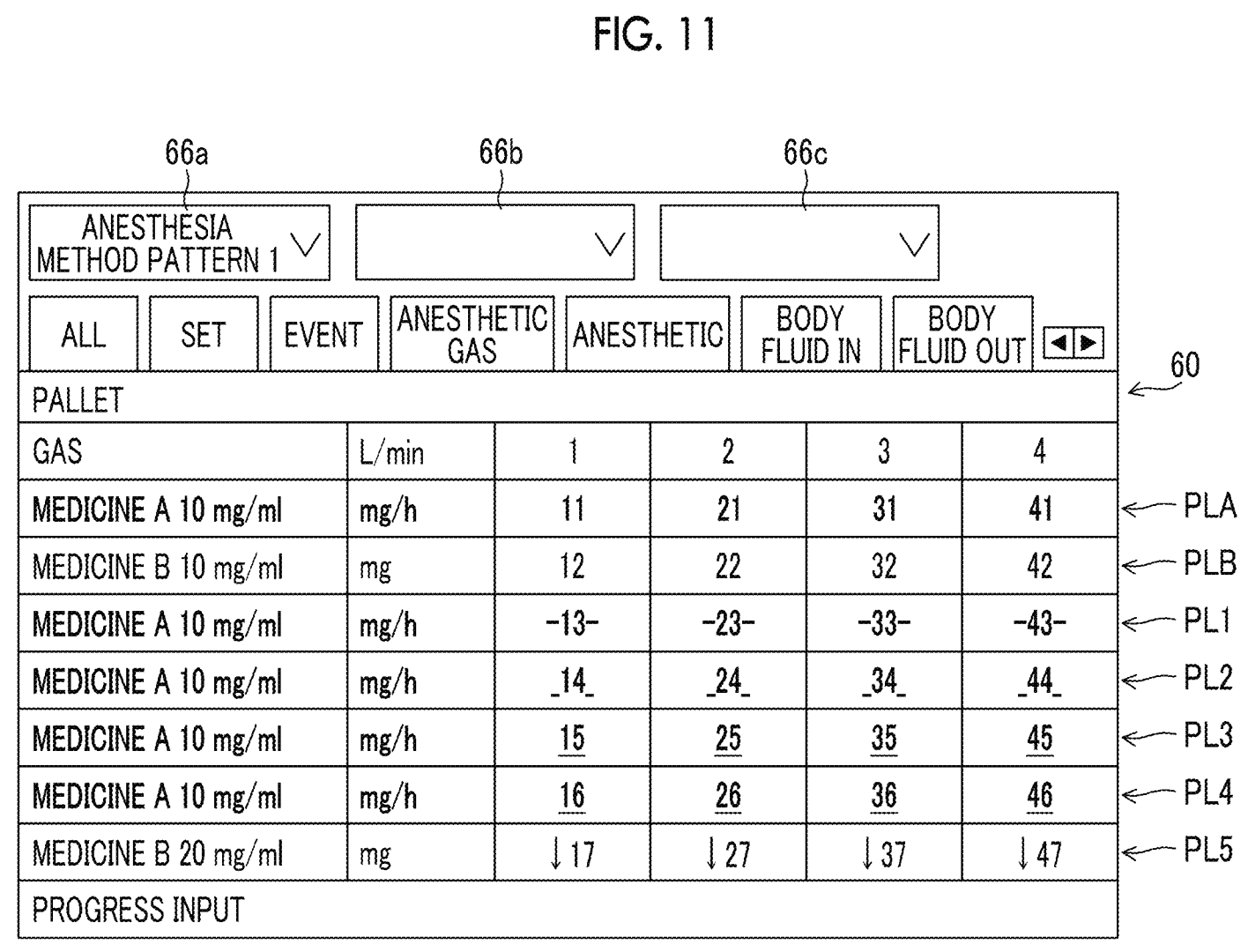

| ANESTHESIA METHOD PATTERN 1 ∨ | | | | | |
|---|---|---|---|---|---|
| ALL | SET | EVENT | ANESTHETIC GAS | ANESTHETIC | BODY FLUID IN | BODY FLUID OUT ▲▼ |

PALLET

| | | 1 | 2 | 3 | 4 | |
|---|---|---|---|---|---|---|
| GAS | L/min | | | | | |
| MEDICINE A 10 mg/ml | mg/h | 11 | 21 | 31 | 41 | ← PLA |
| MEDICINE B 10 mg/ml | mg | 12 | 22 | 32 | 42 | ← PLB |
| MEDICINE A 10 mg/ml | mg/h | −13− | −23− | −33− | −43− | ← PL1 |
| MEDICINE A 10 mg/ml | mg/h | _14_ | _24_ | _34_ | _44_ | ← PL2 |
| MEDICINE A 10 mg/ml | mg/h | 15 | 25 | 35 | 45 | ← PL3 |
| MEDICINE A 10 mg/ml | mg/h | 16 | 26 | 36 | 46 | ← PL4 |
| MEDICINE B 20 mg/ml | mg | ↓17 | ↓27 | ↓37 | ↓47 | ← PL5 |

PROGRESS INPUT 66a    66b    66c    60

FIG. 13

| GENERAL ANESTHESIA ⌄ | CAESAREAN SECTION ⌄ | ⌄ | | | | |
|---|---|---|---|---|---|---|
| | EVENT | REMARKS | | | | |
| GENERAL ANESTHESIA | | | | | | |
| CAESAREAN SECTION | L/min | 6 | 1 | 2 | 3 | |
| ANEREM 50 1 mg/ml | mg/k/h | 12 | 1 | 0.5 | 0.8 | |
| ANEREM 50 1 mg/ml | mg/kg | 0.01 | 0.02 | 0.03 | | |
| DIPRIVAN 10 mg/ml | ug/ml | 3 | 2.5 | 2 | 1.5 | |
| ROCURONIUM 50 10 mg/ml | mg | 50 | 10 | 20 | 30 | |
| ROCURONIUM 50 10 mg/ml | mg/h | 40 | 20 | 15 | 10 | |
| FENTANYL 100 50 µg/ml | ug | 100 | 200 | 50 | 25 | |
| ULTIVA 2 0.1 mg/ml | u/k/m | 0.2 | 0.25 | 0.5 | 0.1 | |
| ULTIVA 2 0.1 mg/ml | mg/kg | 0.01 | 0.02 | 0.03 | 0.04 | |
| EPHEDRINE 4 mg/ml | mg | 4 | 8 | 12 | | |
| NEOSYNESIN 4 mg/ml | mg | 0.05 | 0.1 | 0.2 | | |
| ATROPINE 0.5 mg/ml | mg | 0.5 | 0.25 | | | |
| BRIDION 100 mg/ml | mg | 200 | 100 | | | |
| FLUMAZENIL 0.1 mg/ml | mg | 0.2 | 0.3 | 0.1 | | |
| NICARDIPINE 1 mg/ml | mg | 0.5 | 1 | 2 | | |
| NICARDIPINE 1 mg/ml | mg/h | 2 | 3 | 4 | 10 | |
| NEW REMARKS | | | | | | |
| POSTOPERATIVE ANALGESIA | | | | | | |
| ↓ : INTUBATION | | | | | | |
| ↑ : EXTUBATION | | | | | | |

66a 66b 66c 60

| PALLET ITEM | | | | | |
|---|---|---|---|---|---|
| ANESTHESIA START + O2 | | | | | |
| O2 | L/min | 6 | 1 | 2 | 3 |
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg/ml | mg | 50 | 10 | 20 | 30 |
| ROCURONIUM 50 10 mg/ml | mg/h | 40 | 20 | 15 | 10 |
| FENTANYL 100 50 μg/ml | ug | 100 | 200 | 50 | 25 |
| ULTIVA 2 0.1 mg/ml | u/k/m | 0.2 | 0.25 | 0.5 | 0.1 |
| ULTIVA 2 0.1 mg/ml | mg/kg | 0.01 | 0.02 | 0.03 | 0.04 |
| EPHEDRINE 4 mg/ml | mg | 4 | 8 | 12 | |
| NEOSYNESIN 4 mg/ml | mg | 0.05 | 0.1 | 0.2 | |
| ATROPINE 0.5 mg/ml | mg | 0.5 | 0.25 | | |
| BRIDION 100 mg/ml | mg | 200 | 100 | | |
| FLUMAZENIL 0.1 mg/ml | mg | 0.2 | 0.3 | 0.1 | |

| DETAILED CLASSIFICATION SELECTION     ✕ |
| EVENT |
| ANESTHETIC GAS |
| ANESTHETIC |
| REMARKS |
| SET |

OK     CANCEL

Figure 21:
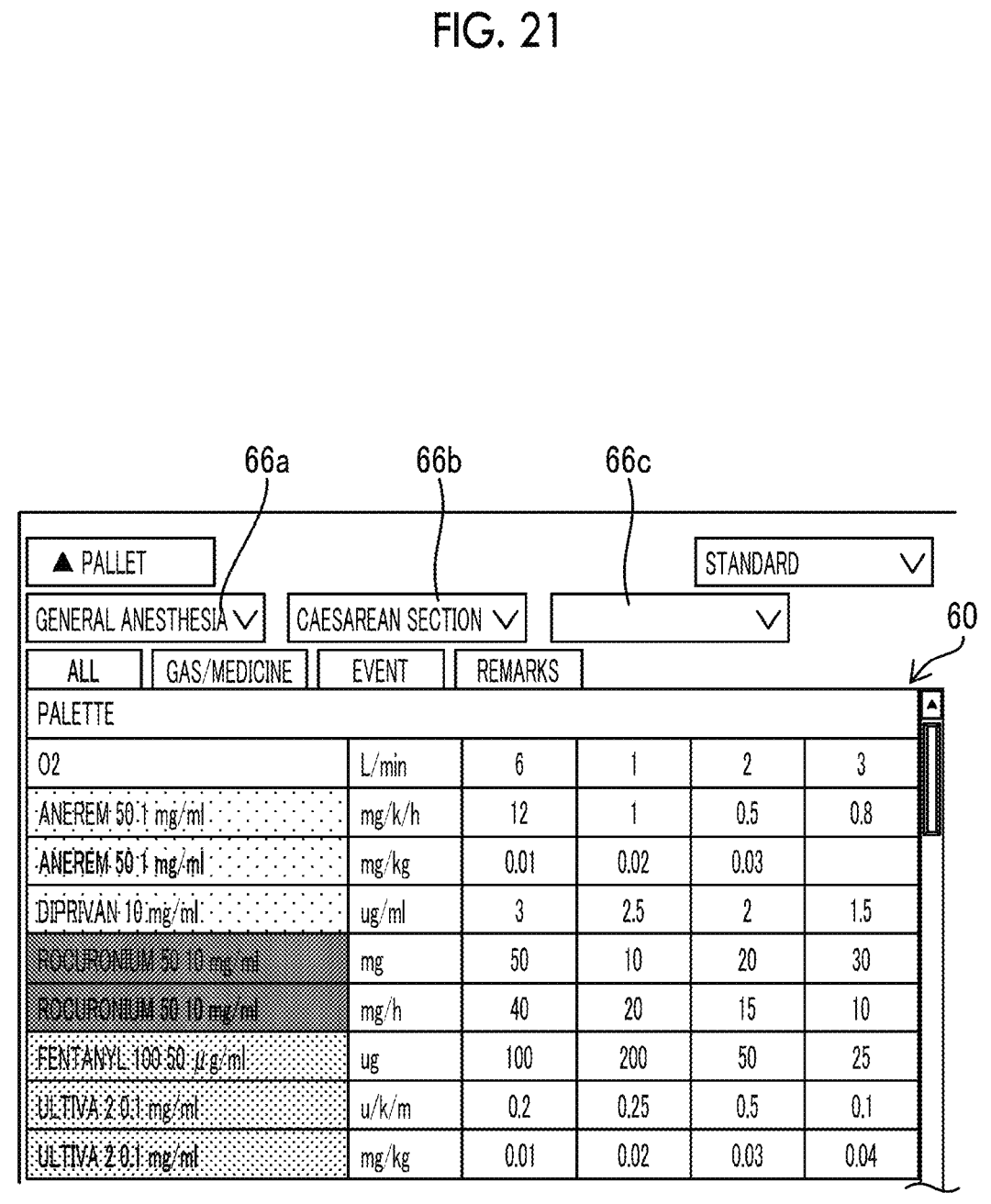

| ▲ PALLET | | | | | STANDARD ∨ |
|---|---|---|---|---|---|

| GENERAL ANESTHESIA ∨ | CAESAREAN SECTION ∨ | ∨ |
|---|---|---|

60

| ALL | GAS/MEDICINE | EVENT | REMARKS |
|---|---|---|---|

| PALETTE | | | | | |
|---|---|---|---|---|---|
| O2 | L/min | 6 | 1 | 2 | 3 |
| ANEREM 50 1 mg/ml | mg/k/h | 12 | 1 | 0.5 | 0.8 |
| ANEREM 50 1 mg/ml | mg/kg | 0.01 | 0.02 | 0.03 | |
| DIPRIVAN 10 mg/ml | ug/ml | 3 | 2.5 | 2 | 1.5 |
| ROCURONIUM 50 10 mg ml | mg | 50 | 10 | 20 | 30 |
| ROCURONIUM 50 10 mg ml | mg/h | 40 | 20 | 15 | 10 |
| FENTANYL 100 50 μg/ml | ug | 100 | 200 | 50 | 25 |
| ULTIVA 2 0.1 mg/ml | u/k/m | 0.2 | 0.25 | 0.5 | 0.1 |
| ULTIVA 2 0.1 mg/ml | mg/kg | 0.01 | 0.02 | 0.03 | 0.04 |

FLOW-SPECIFIC PATTERN SETTING

| FLOW | ANESTHESIA METHOD | TREATMENT DEPARTMENT | OTHERS |
|---|---|---|---|
| CARDIOVASCULAR SURGERY | GENERAL ANESTHESIA | DEPARTMENT OF CARDIOVASCULAR SURGERY | |
| GENERAL ANESTHESIA (INHALATION) | GENERAL ANESTHESIA | | |
| GENERAL ANESTHESIA (TIVA) | GENERAL ANESTHESIA | | |
| TOTAL (INHALATION) + EPIDURAL ANESTHESIA | GENERAL ANESTHESIA | | |
| TOTAL (TIVA) + EPIDURAL ANESTHESIA | GENERAL ANESTHESIA | | |
| TOTAL SPINAL ANESTHESIA | GENERAL ANESTHESIA | | |
| TOTAL CAUDAL ANESTHESIA | GENERAL ANESTHESIA | | |
| TOTAL SPINAL EPIDURAL ANESTHESIA | GENERAL ANESTHESIA | | |
| TOTAL + OBTURATOR NERVE BLOCK | GENERAL ANESTHESIA | | |
| SPINAL ANESTHESIA | LOCAL ANESTHESIA | | |
| SPINAL EPIDURAL ANESTHESIA | LOCAL ANESTHESIA | | |
| EPIDURAL ANESTHESIA | LOCAL ANESTHESIA | | |
| CAUDAL ANESTHESIA | LOCAL ANESTHESIA | | |
| SPINAL ANESTHESIA + OBTURATOR NERVE | LOCAL ANESTHESIA | | |
| OBTURATOR NERVE BLOCK | LOCAL ANESTHESIA | | |
| INTRAVENOUS ANESTHESIA | LOCAL ANESTHESIA | | |
| CAESAREAN SECTION (GENERAL ANESTHESIA) | GENERAL ANESTHESIA | CAESAREAN SECTION | |
| CAESAREAN SECTION (SPINAL ANESTHESIA) | LOCAL ANESTHESIA | CAESAREAN SECTION | |
| OPHTHALMOLOGY | LOCAL ANESTHESIA | | |
| LOCAL ANESTHESIA IN GENERAL | LOCAL ANESTHESIA | | |

CLOSE

FLOW-SPECIFIC PATTERN REGISTRATION

| | | |
|---|---|---|
| FLOW | TOTAL (TIVA) + EPIDURAL ANESTHESIA | |
| ANESTHESIA METHOD | GENERAL ANESTHESIA | SELECT DELETE |
| TREATMENT DEPARTMENT | | SELECT DELETE |
| OTHERS | | SELECT DELETE |

154

152

REGISTER　　CANCEL

| ALL | GAS/MEDICINE | EVENT | REMARKS | | | |
|------|------|------|------|------|------|------|
| PALETTE | | | | | | |
| O2 | L/min | 6 | 1 | 2 | 3 | |
| ANEREM 50 1 mg/ml | mg/k/h | 12 | 1 | 0.5 | 0.8 | |
| ANEREM 50 1 mg/ml | mg/kg | 0.01 | 0.02 | 0.03 | | |
| DIPRIVAN 10 mg/ml | ug/ml | 3 | 2.5 | 2 | 1.5 | |
| ROCURONIUM 50 10 mg/ml | mg | 50 | 10 | 20 | 30 | |
| ROCURONIUM 50 10 mg/ml | mg/h | 40 | 20 | 15 | 10 | |
| FENTANYL 100 50 μg/ml | ug | 100 | 200 | 50 | 25 | |
| ULTIVA 2 0.1 mg/ml | u/k/m | 0.2 | 0.25 | 0.5 | 0.1 | |
| ULTIVA 2 0.1 mg/ml | mg/kg | 0.01 | 0.02 | 0.03 | 0.04 | |
| EPHEDRINE 4 mg/ml | mg | 4 | 8 | 12 | | |
| NEOSYNESIN 4 mg/ml | mg | 0.05 | 0.1 | 0.2 | | |
| ATROPINE 0.5 mg/ml | mg | 0.5 | 0.25 | | | |
| BRIDION 100 mg/ml | mg | 200 | 100 | | | |
| FLUMAZENIL 0.1 mg/ml | mg | 0.2 | 0.3 | 0.1 | | |
| NICARDIPINE 1 mg/ml | mg | 0.5 | 1 | 2 | | |
| NICARDIPINE 1 mg/ml | mg/h | 2 | 3 | 4 | 10 | |
| NEW REMARKS | | | | | | |
| POSTOPERATIVE ANALGESIA | | | | | | |
| ↓: INTUBATION | | | | | | |
| ↑: EXTUBATION | | | | | | |
| AA: ANESTHESIA START | | | | | | |
| AA: ANESTHESIA END | | | | | | |
| BB: OPERATION START | | | | | | |
| BB: OPERATION END | | | | | | |
| DI: DIFFERENTIAL LUNG VENTILATION START | | | | | | |
| DI: DIFFERENTIAL LUNG VENTILATION END | | | | | | |

Figure 27:
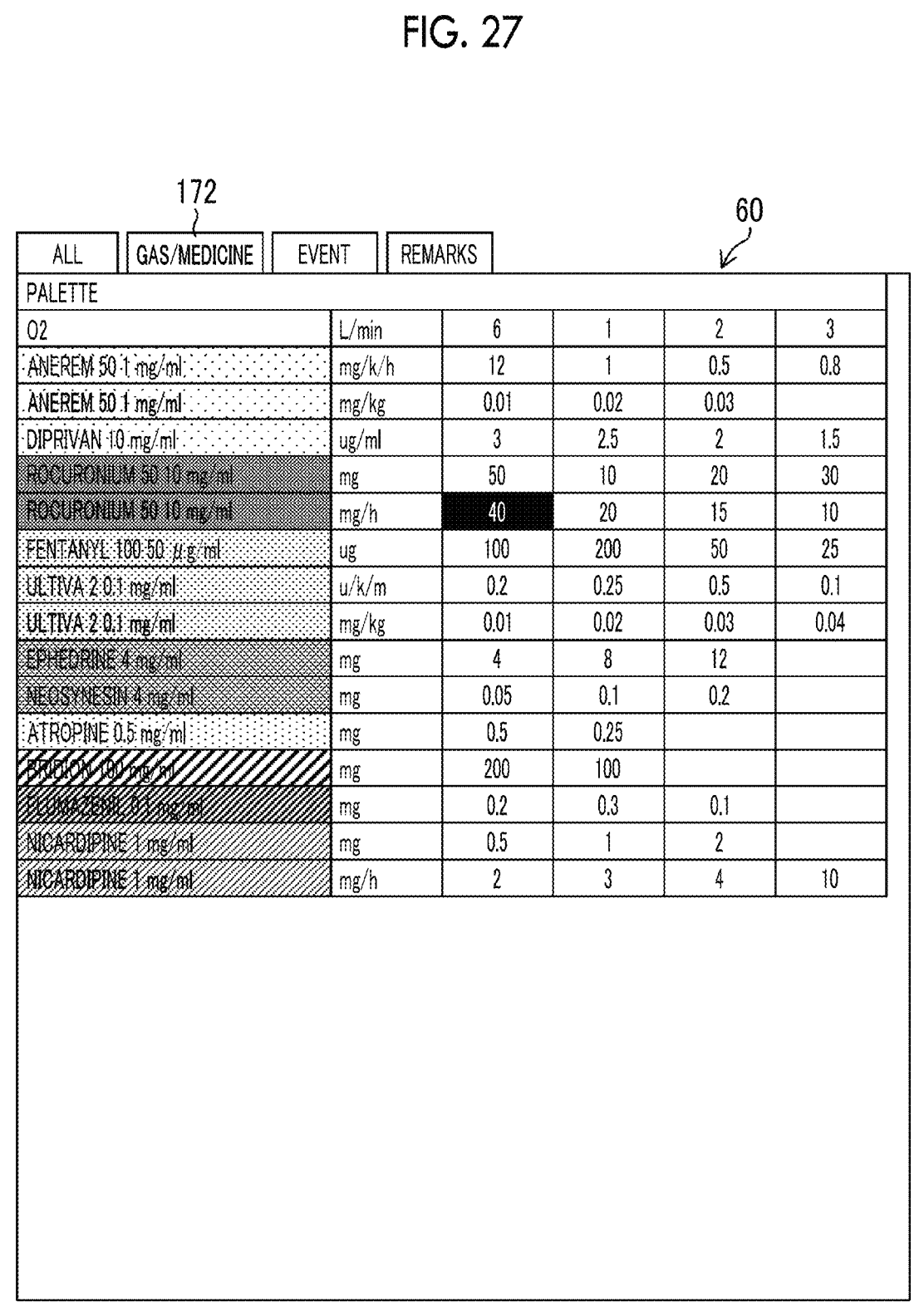

| ALL | GAS/MEDICINE | EVENT | REMARKS | | | |
|---|---|---|---|---|---|---|
| PALETTE | | | | | | |
| O2 | L/min | 6 | 1 | 2 | 3 | |
| ANEREM 50 1 mg/ml | mg/k/h | 12 | 1 | 0.5 | 0.8 | |
| ANEREM 50 1 mg/ml | mg/kg | 0.01 | 0.02 | 0.03 | | |
| DIPRIVAN 10 mg/ml | ug/ml | 3 | 2.5 | 2 | 1.5 | |
| ROCURONIUM 50 10 mg/ml | mg | 50 | 10 | 20 | 30 | |
| ROCURONIUM 50 10 mg/ml | mg/h | 40 | 20 | 15 | 10 | |
| FENTANYL 100 50 μg/ml | ug | 100 | 200 | 50 | 25 | |
| ULTIVA 2 0.1 mg/ml | u/k/m | 0.2 | 0.25 | 0.5 | 0.1 | |
| ULTIVA 2 0.1 mg/ml | mg/kg | 0.01 | 0.02 | 0.03 | 0.04 | |
| EPHEDRINE 4 mg/ml | mg | 4 | 8 | 12 | | |
| NEOSYNESIN 4 mg/ml | mg | 0.05 | 0.1 | 0.2 | | |
| ATROPINE 0.5 mg/ml | mg | 0.5 | 0.25 | | | |
| BRIDION 100 mg/ml | mg | 200 | 100 | | | |
| FLUMAZENIL 0.1 mg/ml | mg | 0.2 | 0.3 | 0.1 | | |
| NICARDIPINE 1 mg/ml | mg | 0.5 | 1 | 2 | | |
| NICARDIPINE 1 mg/ml | mg/h | 2 | 3 | 4 | 10 | |

| ALL | GAS/MEDICINE | EVENT | REMARKS |
| --- | --- | --- | --- |

| PALETTE |
| --- |
| ↓: INTUBATION |
| ↑: EXTUBATION |
| AA: ANESTHESIA START |
| AA: ANESTHESIA END |
| BB: OPERATION START |
| BB: OPERATION END |
| DI: DIFFERENTIAL LUNG VENTILATION START |
| DI: DIFFERENTIAL LUNG VENTILATION END |
| PP: PNEUMOPERITONEUM START |
| PP: PNEUMOPERITONEUM END |
| HA: HYPOTHERMIC ANESTHESIA START |
| HA: HYPOTHERMIC ANESTHESIA END |
| HT: HYPERTHERMIA START |
| HT: HYPERTHERMIA END |
| PR: PRINGLE START |
| PR: PRINGLE END |
| MI: MICRO START |
| MI: MICRO END |
| TO: HYSTEROTOMY |
| BD: BABY DELIVERY |
| PD: PLACENTA DELIVERY |

MEDICAL INFORMATION MANAGEMENT SYSTEM, MEDICAL INFORMATION MANAGEMENT METHOD, AND PROGRAM

The present application claims priority under 35 U.S.C. § 119 to Japanese Patent Application No. 2021-077521 filed on Apr. 30, 2021. Each of the above application is hereby expressly incorporated by reference, in its entirety, into the present application.

BACKGROUND OF THE INVENTION

1. Field of the Invention

The present disclosure relates to a medical information management system, a medical information management method, and a program, and in particular, to an information processing technique and a user interface technique suitable for recording and management of information regarding medicines or the like administered in an operation or the like.

2. Description of the Related Art

JP2016-24793A describes an anesthesia recording management apparatus that records a history of anesthesia administered in an operation or an examination along with biological information. An anesthesia recording field displayed on a display unit of the anesthesia recording management apparatus described in JP2016-24793A includes a biological information history field that displays transition of the biological information, and an anesthesia information history field that displays transition of the anesthesia information, with the horizontal axis as a time axis. In a case of inputting the anesthesia information including information regarding an anesthetic and information regarding medication, an operator inputs information to input fields, such as a time input field, an anesthetic input field, and a numerical value input field, of an input window, and presses a register button, whereby the anesthesia information is registered.

SUMMARY OF THE INVENTION

An object of the present disclosure is to provide a medical information management system, a medical information management method, and a program capable of, in a case where a plurality of pieces of medical information including biological information of a target patient and administration information of medicines to the target patient or event information indicating an event (matter) with respect to medical practice to the target patient (hereinafter, referred to as administration information and the like) are displayed along a common time axis, and the administration information and the like are input, simplifying input work of the administration information and the like compared to a case where contents of the administration information and the like and time periods are input individually.

A medical information management system according to an aspect of the present disclosure is a medical information management system comprising a processor, and a storage device in which a program that is executed by the processor is stored. The processor executes the program to display a display field having a biological information display field where biological information of a target patient is displayed along a time axis and an administration information display field where administration information including information regarding an administered medicine, a dose, and an administration timing to the target patient in a period corresponding to a display range of the time axis of the biological information display field is displayed, and an input list where a plurality of medicine regions in correlation with combination information of a plurality of medicines and doses are arranged, receive an input of dragging a first region from among the plurality of medicine regions of the input list and dropping the first region to a second region of the display field, add information indicating that a medicine and a dose correlated with the first region is administered to the target patient at a time in the period corresponding to a position of the second region of the display field to update the administration information in a case where the input of dragging the first region and dropping the first region to the second region is received, and update the display of the administration information display field based on the updated administration information.

The term "medicine" includes a concept of medical gas that is represented by oxygen or nitrous oxide (laughing gas), and transfusions. With the medical information management system of this aspect, a user as a person who uses the system can simply input administration information by dragging the medicine region on the input list and dropping the medicine region to the display field, and can display the administration information updated reflecting input information in the administration information display field.

In a medical information management system according to another aspect of the present disclosure, the second region may be a region in the biological information display field.

In a medical information management system according to another aspect of the present disclosure, the processor may display information indicating a time in the period corresponding to a drag position of the first region and information indicating a medicine and a dose correlated with the first region in the biological information display field in a case where the first region is dragged into the biological information display field.

In the medical information management system according to the aspect of the present disclosure, the processor may display a line segment perpendicular to the time axis depending on a drag position of the first region in a case where the first region is dragged into the display field.

In a medical information management system according to another aspect of the present disclosure, in the first region on the input list, the dose may be displayed as a first dose indicated by a numerical value in a first unit, and the processor may display a second dose indicated by a numerical value in a second unit different from the first unit in a case where the first region is designated on the input list.

In a medical information management system according to another aspect of the present disclosure, the processor may changes a display format of characters of a medicine and a dose in the input list depending on a type of the medicine or an administration method.

In a medical information management system according to another aspect of the present disclosure, the processor may receive an input of display setting including an instruction for display of a part of a plurality of medicines and doses of the medicines displayed in the input list in a different display format, and may display the part of the input list in the different display format based on the display setting.

In a medical information management system according to another aspect of the present disclosure, the processor may receive an input of setting including an instruction for at least one of change, addition, or deletion regarding at least one item among medicines and doses of the medicines displayed in the input list, and may display the plurality of medicine regions in the input list depending on the setting.

In a medical information management system according to another aspect of the present disclosure, the processor may have a plurality of list patterns in which at least one of a medicine or a dose displayed in the input list is different, may receive an input of designating a list pattern for use from the plurality of list patterns, and may display the plurality of medicine regions indicating input candidates of medicines and doses corresponding to the designated list pattern in the input list.

In a medical information management system according to another aspect of the present disclosure, at least one of the plurality of list patterns may be correlated with a type of an operation or a user, and an input of designating the type of the operation or the user may be performed to designate the list pattern for use.

In a medical information management system according to another aspect of the present disclosure, at least one medicine region among the plurality of medicine regions in the input list may be in correlation with a set of information including a plurality of medicines and doses of the medicines.

In a medical information management system according to another aspect of the present disclosure, the display field may further have a supplementary information display field where supplementary information regarding a matter within the period of the display range is displayed, the input list includes a plurality of supplementary regions in correlation with a plurality of supplementary items to be input candidates, and the processor may receive an input of dragging a third region from the plurality of supplementary regions of the input list and dropping the third region to a fourth region of the display field, may add information indicating that a matter of a supplementary item correlated with the third region is executed at a time in the period corresponding to a position of the fourth region of the display field, to update the supplementary information in a case where the input of dragging the third region and dropping the third region to the fourth region is received, and may update display of the supplementary information display field based on the updated supplementary information.

In a medical information management system according to another aspect of the present disclosure, the supplementary information may include at least one of event information or remarks information, the plurality of supplementary items may include at least one of an event item or a remarks item, and the plurality of supplementary regions may include at least one of an event region in correlation with the event item or a remarks region in correlation with the remarks item.

In a medical information management system according to another aspect of the present disclosure, the processor may receive an input of setting including an instruction for at least one of change, addition, or deletion regarding at least one item among medicines, doses of the medicines, and a supplementary item displayed in the input list, and may display the plurality of medicine regions and the plurality of supplementary regions in the input list depending on the setting.

In a medical information management system according to another aspect of the present disclosure, the processor may have a plurality of list patterns in which at least one of a medicine, a dose of each medicine, or a supplementary item displayed in the input list is different, may receive an input of designating a list pattern for use from the plurality of list patterns, and may display the plurality of medicine regions and the plurality of supplementary regions indicating input candidates of medicines, doses of the medicines, and supplementary items corresponding to the designated list pattern in the input list.

In a medical information management system according to another aspect of the present disclosure, the input list may include a set region in correlation with a set of information regarding a supplementary, a medicine, and a dose, and the processor may receive an input of dragging the set region of the input list and dropping the set region to a fifth region of the display field, may add a record indicating that a matter of a supplementary item correlated with the set region is executed at a time in the period corresponding to a position of the fifth region of the display field, to update the supplementary information and may add information indicating that a medicine and a dose correlated with the set region are administered to the target patient, to update the administration information in a case where the input of dragging the set region and dropping the set region to the fifth region of the display field is received, and may update the display of the supplementary information display field based on the updated supplementary information and may update the display of the administration information display field based on the updated administration information.

In a medical information management system according to another aspect of the present disclosure, the processor may acquire the biological information of the target patient from at least one of a biological information sensor or a data server, and may display a graph of the acquired biological information in the biological information display field.

A medical information management system according to another aspect of the present disclosure may further comprise a display device that displays the display field and the input list, and an input device that receives an operation of drag-and-drop.

A medical information management method according to another aspect of the present disclosure is a medical information management method that is executed by a computer, and comprises, at the computer, acquiring biological information of a target patient, displaying, on a display device, a display field having a biological information display field where the acquired biological information is displayed along a time axis and an administration information display field where administration information including information regarding an administered medicine, a dose, and an administration timing to the target patient in a period corresponding to a display range of the time axis of the biological information display field is displayed, and an input list where a plurality of medicine regions in correlation with combination information of a plurality of medicines and doses are arranged, receiving an input of dragging a first region from among the plurality of medicine regions included in the input list and dropping the first region to a second region of the display field, adding information indicating that a medicine and a dose correlated with the first region is administered to the target patient at a time in the period corresponding to a position of the second region of the display field, to update the administration information in a case where the input of dragging the first region and dropping the first region to the second region is received, and updating the display of the administration information display field based on the updated administration information.

A non-transitory computer recording medium storing a program according to another aspect of the present disclosure causes a computer to realize a function of displaying a display field having a biological information display field where biological information of a target patient is displayed along a time axis and an administration information display field where administration information including information regarding an administered medicine, a dose, and an administration timing to the target patient in a period corresponding to a display range of the time axis of the biological information display field is displayed, and an input list where a plurality of medicine regions in correlation with combination information of a plurality of medicines and doses are arranged, a function of receiving an input of dragging a first region from among the plurality of medicine regions of the input list and dropping the first region to a second region of the display field, a function of adding information indicating that a medicine and a dose correlated with the first region is administered to the target patient at a time in the period corresponding to a position of the second region of the display field, to update the administration information in a case where the input of dragging the first region and dropping the first region to the second region is received, and a function of updating the display of the administration information display field based on the updated administration information.

According to the present disclosure, it is possible to simplify user's input work of administration information.

BRIEF DESCRIPTION OF THE DRAWINGS

FIG. 2 is an example of a login screen in the medical information management system according to the embodiment.

FIG. 6 is a display example of doses in a plurality of units that are displayed in a case where a medicine region on the input list is designated.

FIG. 7 is another display example of doses in a plurality of units that are displayed in a case where a medicine region on the input list is designated.

FIG. 8 is a display example showing a part of the input list.

FIG. 9 is an enlarged view of a part of the input list.

FIG. 11 is a diagram showing an example of highlighting of pallet items of the input list.

FIG. 13 is a display example of the input list.

FIG. 18 is an example of a classification selection screen on which selection of a classification of a pallet item is received.

FIG. 21 is an example of an input list that is displayed in association with an operation flow.

FIG. 23 is an example of a flow-specific pattern setting screen on which an input of setting a flow-specific pattern is received.

FIG. 24 is an example of a flow-specific pattern registration screen.

FIG. 26 is an example of an input list that displays all types of pallet items including medicines, events, and remarks.

FIG. 27 is an example of an input list 60 that displays pallet items sorted into a category of medicines.

FIG. 28 is an example of an input list that displays pallet items sorted into a category of events.

FIG. 30 is an explanatory view showing an example in a case of simultaneously inputting a plurality of input items made in a set to a pallet.

FIG. 31 is a screen transition diagram showing an example of an operation procedure in a case of inputting administration information without using a pallet.

FIG. 34 is a screen example in a case of inputting remarks information without using a pallet.

FIG. 40 is a block diagram showing a configuration example of the medical information management system according to the embodiment.

DESCRIPTION OF THE PREFERRED EMBODIMENTS

Hereinafter, preferred embodiments of the present disclosure will be described in detail referring to the accompanying drawings. In the specification, the same components are represented by the same reference signs, and overlapping description will not be repeated.

Embodiment 1

System Configuration Example

Figure 1:
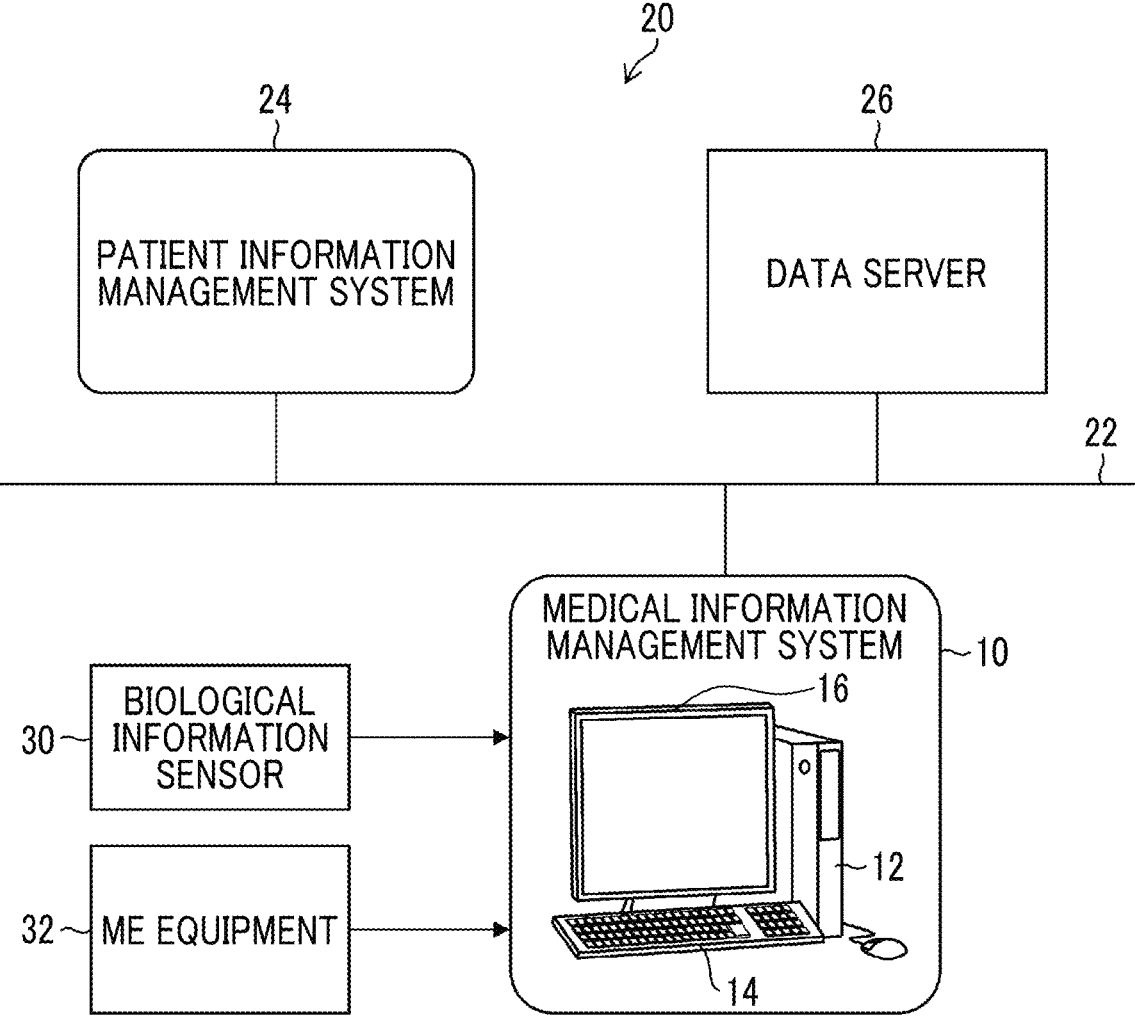
FIG. 1 is a block diagram showing an example of a medical information system including a medical information management system according to an embodiment.

FIG. 1 is a block diagram showing an example of a medical information system 20 including a medical information management system 10 according to an embodiment. The medical information management system 10 is an information processing system for medical support that acquires biological information of a target patient and information regarding medicines and the like administered to the target patient and records and manages such information in relation with a common time axis. A use place of the medical information management system 10 is not particularly limited, and the medical information management system 10 is used in, for example, an operating room, an intensive care unit (ICU), or an emergency room (ER) in a medical institution.

The medical information management system 10 is realized by a combination of hardware of a computer and software. Software is synonymous with a program. The medical information management system 10 is configured using an information processing apparatus 12. The information processing apparatus 12 includes a processor, a memory, a storage, and a communication interface (not shown). The medical information management system 10 may further include an input device 14 and a display device 16. The input device 14 and the display device 16 function as a user interface of the information processing apparatus 12.

In FIG. 1, although the configuration of a work station is illustrated, a form of hardware of the computer is not particularly limited, and may be a personal computer, may be a tablet terminal, or may be a server computer. A server that provides a processing function of the medical information management system 10 may be an on-premises server or may be a cloud server. The processing function of the medical information management system 10 may be realized by distributed computing using a plurality of computers.

The input device 14 is a device that receives an input from a user and transfers the input to the information processing apparatus 12, and may be, for example, a keyboard, a mouse, a touch panel, other pointing devices, or an appropriate combination thereof. The display device 16 is a device that displays a display screen under the control of the information processing apparatus 12, and may be, for example, a liquid crystal display, an organic electro-luminescence (OEL) display, an inorganic electro-luminescence (IEL) display, or an appropriate combination thereof.

The user as a person who uses the system can input various inputs from the input device 14 while confirming information displayed on the display device 16. In the embodiment, although an example where a mouse is used as the input device 14 has been illustrated, a form in which the input device 14 and the display device 16 are integrally configured, such as a touch display, may be made. An operation using the mouse may be replaced with a corresponding touch operation and executed.

The medical information management system 10 can acquire the biological information of the target patient from various biological information sensors 30. The biological information includes, for example, at least one vital data of a respiratory rate, a pulse rate, blood pressure, body temperature, electroencephalogram, or blood oxygen saturation. The biological information is synonymous with the term "vital information" or "vital sign information". The biological information sensors 30 are sensors that generate vital data of the target patient. The biological information sensors

30 may be connected to a biological information monitor (not shown), and the medical information management system 10 may acquire the biological information through the biological information monitor.

The medical information management system 10 may automatically acquire various kinds of data from medical engineering (ME) equipment 32. The ME equipment 32 may be, for example, an anesthesia machine, a syringe pump, a transfusion pump, or an appropriate combination thereof. Data acquired from the ME equipment 32 includes, for example, an administered medicine, a dose of the medicine, an amount of ventilation, an oxygen concentration, airway pressure, and a gas flow rate.

The medical information system 20 is a computer system that supports medical office work and medical treatment in a medical institution, and includes a patient information management system 24, a data server 26, and the medical information management system 10. The medical information system 20 may include one or more modalities (medical equipment), such as a computed tomography (CT) apparatus and a magnetic resonance imaging (MRI) apparatus, a medical image management system, a clinical examination system, a reservation system, and an accounting system. The patient information management system 24 is a system that manages attribute information of the target patient, such as name, sex, and age, and may be, for example, an electronic medical record system or an in-hospital data warehouse (DWH).

The medical information management system 10 is connected to the patient information management system 24 and the data server 26 to be communicable through a communication line 22. The medical information management system 10 can acquire the attribute information of the target patient, such as name, sex, and age, from the patient information management system 24. The medical information management system 10 can store data of the biological information and the administration information of the target patient in the data server 26 or can acquire data from the data server 26.

The medical information management system 10 may be configured as a composite medical support system that supports complicated work in the progress of an operation from preoperative work, such as reception of an order of an operation and a schedule, to intraoperative anesthesia records and nursing records, a postoperative state at the time of an exit from a room, and postoperative rounds.

Outline of Functions of Medical Information Management System 10

Hereinafter, a main function of the medical information management system 10 will be described using a specific example of a display screen. Various functions of the medical information management system 10 are realized by a processor executing a program. Here, a program that causes the processor to realize a medical information management function of the medical information management system 10 is referred to as a medical information management program.

Figure 2:
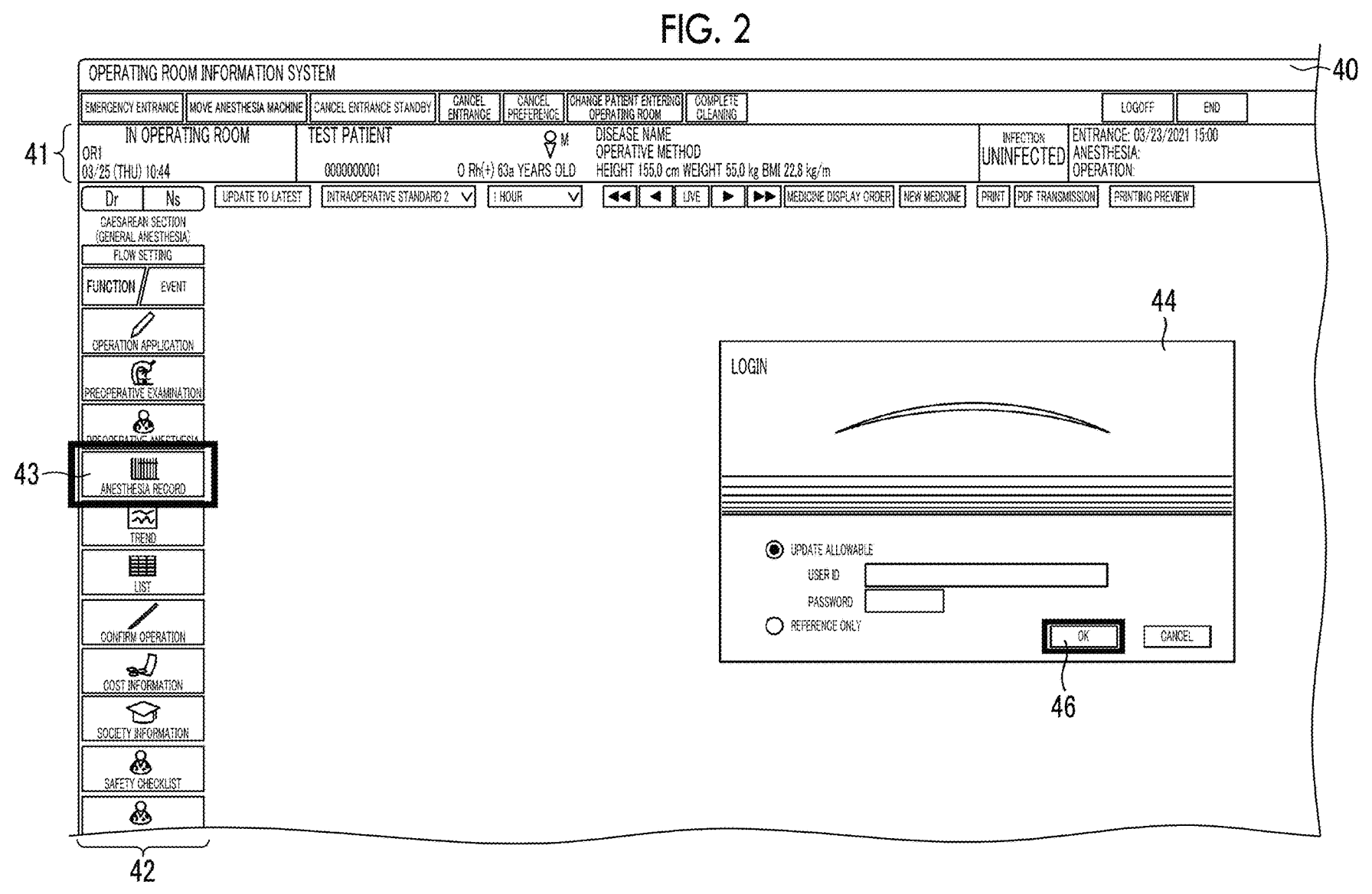

FIG. 2 is a screen example showing an example of a procedure of a login operation in the medical information management system 10. An application screen 40 that is displayed on the display device 16 with the start of the medical information management program has a patient information display field 41 that displays entrance information of the target patient, the name of the target patient, and the like, in a screen upper portion, and has a scrollable navigation bar 42 on a screen left side.

The display "test patient" of a name field in the patient information display field 41 of FIG. 2 is convenient display, and actually, the name of the target patient is displayed in the name field.

The navigation bar 42 is a tool bar in which a plurality of function buttons (icons) corresponding to an operation work flow are arranged in a vertical direction. Here, an example of a case where an anesthesia record is created by the medical information management system 10 is shown.

In a case of recording an anesthesia record, an operator depresses an anesthesia record button 43 of the navigation bar 42. The expression "depress" or "press" on a graphical user interface (GUI) button, such as a function button, includes a concept of an operation to perform an input of a command corresponding to a button by an operation to click, touch, select, or designate the button.

Figure 3:
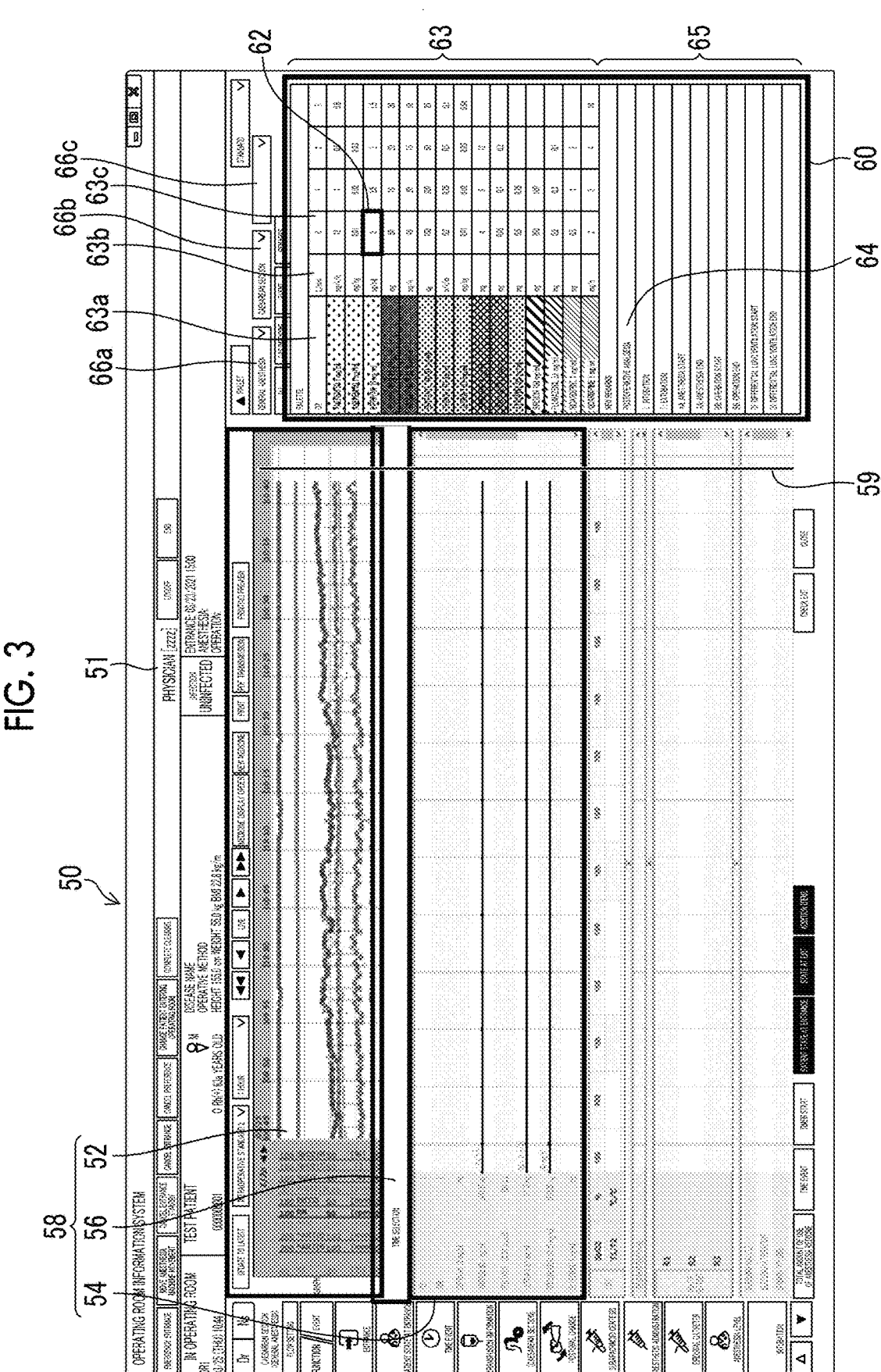
FIG. 3 is an example of an anesthesia recording screen in the medical information management system according to the embodiment.

In a case where the anesthesia record button 43 is depressed, a login screen 44 shown in FIG. 2 is displayed. The login screen 44 has input fields of a user identification (ID) and a password, and receives an input from the user. In a case where the user inputs the user ID and the password from the input device 14 and depresses an OK button 46, an anesthesia recording screen 50 shown in FIG. 3 is displayed. In the embodiment, although the login screen 44 is displayed in a case where the anesthesia record button 43 is depressed, and the user inputs the user ID; however, the present disclosure is not limited thereto. The login screen 44 for inputting the user ID may be displayed in a case where the medical information management program is started. The application screen 40 may be displayed after the user ID is input on the login screen 44, and the anesthesia recording screen 50 may be displayed with the depression of the anesthesia record button 43. The display of at least one of the login screen 44 or the application screen 40 may not performed. For example, the anesthesia recording screen 50 may be displayed when the medical information management program is started.

FIG. 3 is an example of the anesthesia recording screen 50. The anesthesia recording screen 50 has a user name display field 51 in an uppermost portion, and the user name is displayed in the user name display field 51 during login. The display of a user name, such as "physician [ZZZ]" in the user name display field 51 of FIG. 3 is convenient display, and actually, the user name associated with the logged-in user ID is displayed.

The anesthesia recording function of the medical information management system 10 automatically records intraoperative vital sign data every second, fetches data from the ME equipment 32, and reflects data in the anesthesia record. The intraoperative anesthesia record can be referred to from a nurses' station, a physician common room, or the like through the communication line 22 in real time.

The anesthesia recording screen 50 includes a recording information display field 58 having a biological information display field 52, an administration information display field 54, and a supplementary information display field 56, and an input list 60 that provides input candidates of information regarding medicines, events, and remarks. The recording information display field 58 is an example of a "display field" in the present disclosure. In the embodiment, the recording information display field 58 has the administration information display field 54 and the supplementary information display field 56, but may have at least the biological information display field 52 and at least one of the administration information display field 54 or the supplementary information display field 56. The input list 60 has the input candidates of information regarding medicines, events, and remarks, but may have at least one of medicines, events, or remarks. Although the anesthesia recording screen 50 for anesthesia recording is illustrated as a display screen on which the recording information display field 58 and the input list 60 are displayed, the present disclosure is not limited thereto. A medical information display screen including the recording information display field 58 and the input list 60 may be used.

The biological information display field 52 is a display area where the biological information of the target patient is displayed along a time axis. In the biological information display field 52, at least one of a respiratory rate, a pulse rate, blood pressure, body temperature, electroencephalogram, or blood oxygen saturation, and preferably, data of a plurality of types of vital items is displayed in a graph. In FIG. 3, the horizontal axis (horizontal direction) represents a time axis, and the vertical axis (vertical direction) represents a value of each vital item. A graph of time-series vital data displayed in the biological information display field 52 is referred to as a vital graph.

A display range of the time axis in the biological information display field 52 includes at least a part of a period (medical practice period) during which medical practice to the target patient is performed. The period (time range) corresponding to the display range of the time axis displayed in the biological information display field 52 and the scale of the time axis may be automatically set based on the program or may be designated by the operator through the input device 14.

The administration information display field 54 is a display area where administration information including a medicine (administered medicine) administered to the target patient, a dose, and an administration time is displayed. In a case of continuous administration, the administration time includes a concept of an administration period including an administration timing (administration start) and an administration end. In a case of one-shot administration, the administration time is an administration timing. The "timing" may be recorded as information of time. The medicine is not limited to an anesthetic, and may be other medicines, at least one of medical gas that is represented by oxygen or nitrous oxide (laughing gas) or a transfusion, or a combination thereof.

The supplementary information display field 56 is a display area where event information and/or remarks information is displayed. The event information is, for example, information regarding a matter having a start point and an end point, such as an anesthesia start or an anesthesia end. The remarks information is information that is recorded with respect to one point of time, and includes regarding other matters that the event information. In the specification, the term "supplementary information" is used as an inclusive concept including the event information and the remarks information.

The supplementary information display field 56 may be configured such that an event display field where the event information is displayed and a remarks display field where the remarks information is displayed may be divided and disposed into separate rows. For example, the supplementary information display field 56 is classified into upper and lower two rows, the upper end is the remarks display field, and the lower end is the event display field.

The administration information display field 54 and the supplementary information display field 56 display the administration information and the supplementary information along the time axis common to the biological information display field 52, respectively. That is, the administration information display field 54 can display the administration information including information regarding the administered medicine, the dose, and the administration timing to the target patient in the period corresponding to the display range of the time axis of the biological information display field 52. The supplementary information display field 56 can display the supplementary information in the period corresponding to the display range of the time axis of the biological information display field 52.

In a case where the display range of the time axis displayed in the recording information display field 58 includes a current time, a line segment 59 to be a mark indicating a position of the current time on the time axis is displayed in the recording information display field 58. The line segment 59 is a straight line in the vertical direction perpendicular to the time axis and is displayed as a single line segment having a length extending over the biological information display field 52, the administration information display field 54, and the supplementary information display field 56. The line segment 59 may be displayed only in the biological information display field 52 and any one of the administration information display field 54 or the supplementary information display field 56. Alternatively, the line segment 59 may be a line segment split in each display field of the biological information display field 52, the administration information display field 54, and the supplementary information display field 56.

The input list 60 is displayed on a right side of the recording information display field 58. In the medical information management system 10, a pallet input function is implemented as a function of supporting input work of data of the user. The pallet input function is a function capable of simply inputting data at any position on the screen with a drag-and-drop function from input candidates (hereinafter, referred to as a pallet) disposed in a dice shape. The input candidates disposed in a dice shape are configured of, for example, medicines and doses. A region (item) to be a target of drag-and-drop on the input list 60 is referred to as a "pallet item".

The input list 60 includes a medicine list 63 in which a plurality of medicine regions 62 in correlation with combination information of a plurality of medicines and doses are arranged. The medicine list 63 is displayed in a table format in which a medicine type cell 63a indicating a type of a medicine, a unit cell 63b indicating an administration unit of the medicine, and a plurality of dose cells 63c indicating a medicine dose represented in the administration unit are arranged in a row direction (horizontal direction). Each of a plurality of dose cells 63c is a medicine region 62 corresponding to a pallet item. For example, as combination information of a medicine and a dose, information for specifying a type of a medicine "DIPRIVAN 10 mg/ml" and information indicating that the dose of the medicine is "3 μg/ml" correspond to the medicine region 62 attached with a numerical value of the dose, "3", in a third row from the top in the input list 60 of FIG. 3. In this case, the pallet item (medicine region 62) in correlation with the combination information of the medicine and the dose is referred to as a medicine pallet.

The input list 60 is not limited to the medicine list 63, and may include a supplementary list 65 in which a plurality of supplementary regions 64 as pallet items of supplementary information are arranged. A supplementary item corresponds to each of a plurality of supplementary regions 64. A plurality of supplementary regions 64 may include a plurality of event regions as pallet items in correlation with event information and a plurality of remarks regions as pallet items of remarks information. A pallet item (event region) in correlation with the event information is referred to as an event pallet, and a pallet item (remarks region) in correlation with the remarks information is referred to as a remarks pallet. The event pallet and the remarks pallet are inclusively referred to as a supplementary pallet. A plurality of supplementary items include at least one of an event item or a remarks item.

Although the input list 60 shown in FIG. 3 is an example of a list in which all types of pallet items of the medicine pallet, the event pallet, and the remarks pallet are displayed in a list, the present disclosure is not limited to the input list 60 where all types of pallet items are displayed, and an input list may be sorted for each type of an input item, such as medicines, events, or remarks, and the display of the input list may be switched through tab selection.

Hereinafter, Embodiments 2 to 10 of the medical information management system 10 will be described. In the embodiments, common configurations are represented by the same reference signs, and description will not be repeated.

Embodiment 2

The pallet item of the input list 60 can be inserted (drop operation) into any region of the recording information display field 58 including biological information display field 52, the administration information display field 54, and the supplementary information display field 56, regardless of the type of the input item, such as medicines, events, or remarks. For example, the medicine region 62 can be of course dragged and dropped to the administration information display field 54, and the medicine region 62 can also be dragged and dropped to the biological information display field 52.

Figure 4:
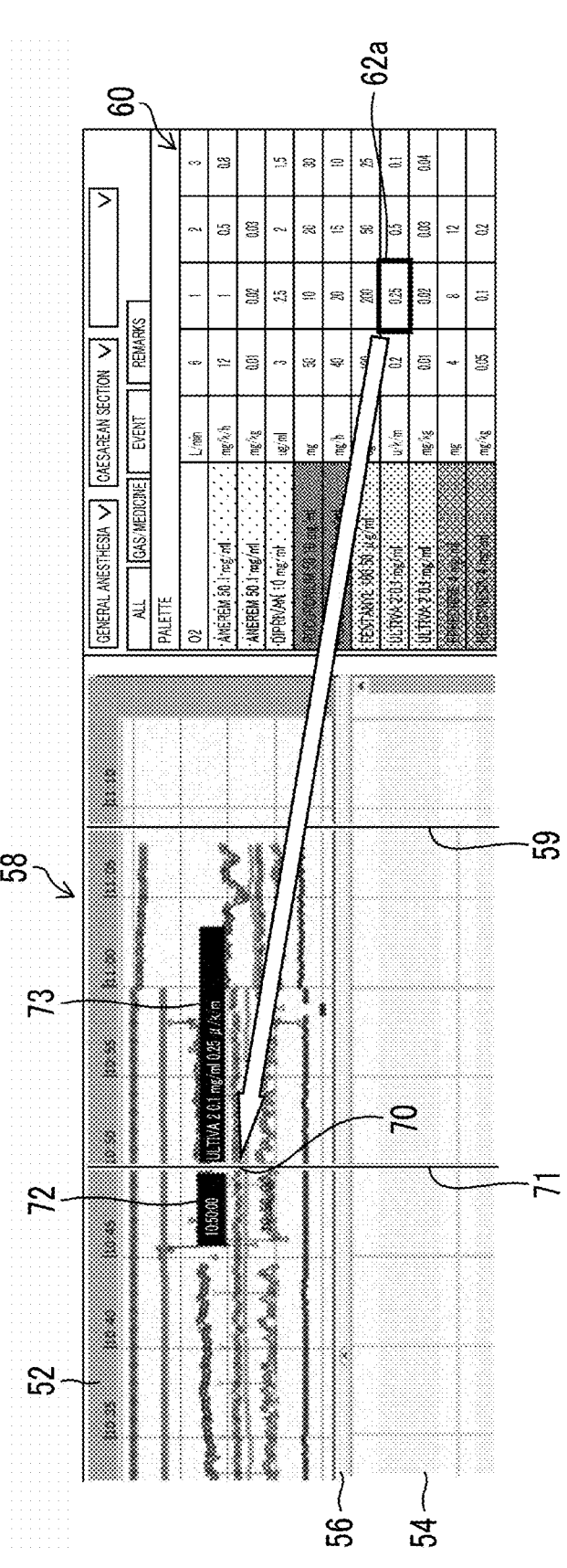
FIG. 4 is an enlarged view showing a display example in a case where a medicine region on an input list is dragged and moved into a biological information display field.

FIG. 4 is an enlarged view showing a display example in a case where a medicine region 62a on the input list 60 is dragged and moved into the biological information display field 52. A medicine correlated with the medicine region 62a is "ULTIVA 2", and a dose is 0.25 μ/k/m. The notation "ULTIVA 2" means "ULTIVA intravenous 2 mg". ULTIVA is Registered Trademark, and a generic name is remifentanil hydrochloride. "μ/k/m" of the administration unit of continuous administration means "μg/kg/minute". The medicine region 62a is an example of a "first region" in the present disclosure.

In a case where a pallet item is dragged from the input list 60 and is moused over the recording information display field 58, a line segment 71 in a vertical direction perpendicular to the time axis of the recording information display field 58 is displayed depending on a mouse position such that a position (mouse position) of a mouse pointer is easily understood. In addition to the line segment 71, information correlated with the pallet and time information corresponding to the line segment 71 are displayed near the mouse position.

In a case of the example shown in FIG. 4, in a case where the medicine region 62a on the input list 60 is moved to a region 70 in the biological information display field 52 with a drag operation, the line segment 71 to be a mark is displayed at a position of a time corresponding to the mouse position in the biological information display field 52, that is, a drag position (a position of the region 70). In addition, time information 72 indicating the time corresponding to the line segment 71 and medicine information 73 correlated with the medicine region 62*a* are displayed near the region 70. The region 70 is an example of a "second region" in the present disclosure.

Similarly to the line segment 59 indicating the current time, it is preferable that the line segment 71 indicating the mouse position in mouseover is displayed as a single line segment having a length extending over the biological information display field 52, the administration information display field 54, and the supplementary information display field 56. The line segment 71 may be displayed only in the biological information display field 52 and any one of the administration information display field 54 or the supplementary information display field 56. Alternatively, the line segment 71 may be a line segment split in each display field of the biological information display field 52, the administration information display field 54, and the supplementary information display field 56. It is preferable that the line segment 71 is displayed in a display aspect different from the line segment 59 indicating the current time. For example, the line segment 71 and the line segment 59 may be displayed in different colors. For example, the line segment 71 indicating the time corresponding to the drag position is displayed in blue, and the line segment 59 indicating the current time is displayed in red. Alternatively, one of the line segment 71 and the line segment 59 may be displayed by a solid line, and the other line segment may be displayed by a broken line.

Figure 5:
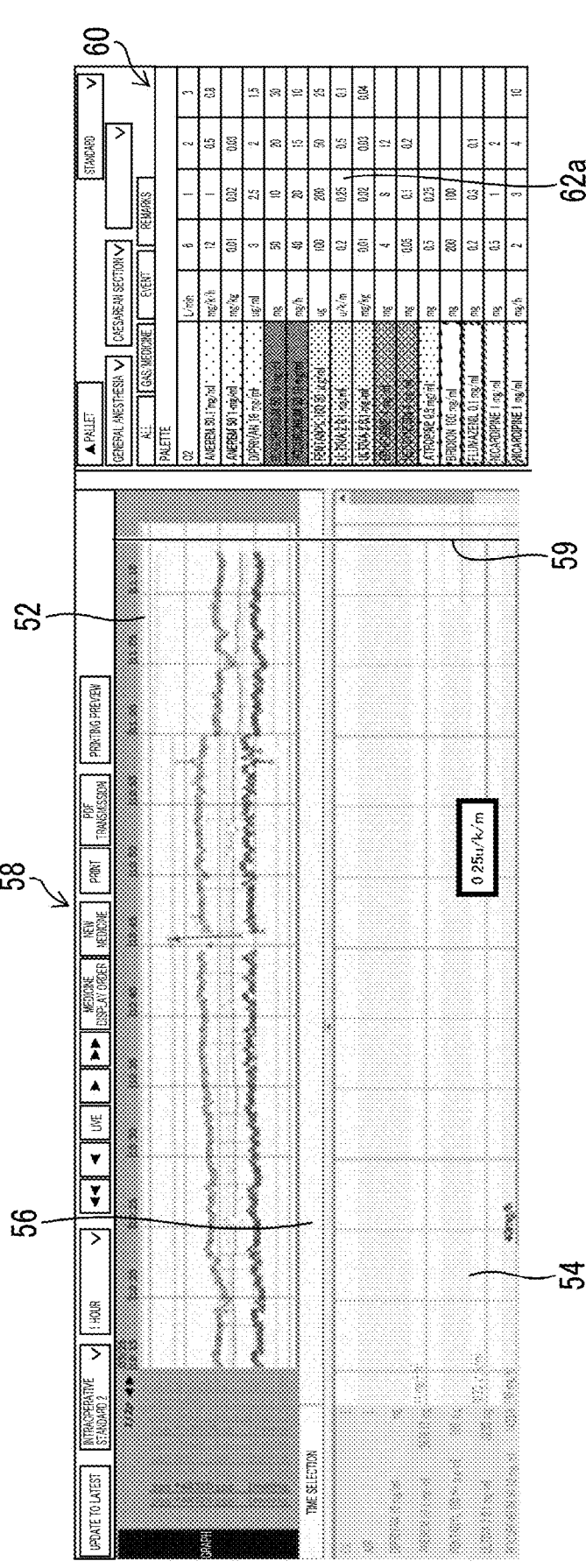
FIG. 5 is a display example of a recording information display field in a case where a drop input is made to a drag position shown in FIG. 4.

FIG. 5 shows a display example in a case where the medicine region 62*a* is dropped to the region 70 in the biological information display field 52 shown in FIG. 4. In a case where the medicine region 62*a* is dropped and input to the region 70 in the biological information display field 52, information indicating that administration is performed to the target patient with the medicine and the dose correlated with the medicine region 62*a* is added to a time corresponding to the drop position to update the administration information, and the display of the administration information in the administration information display field 54 is updated.

In a case where a medicine name correlated with the medicine region 62*a* is in a column of a medicine name on a left side in the administration information display field 54, a numerical value indicating the dose is displayed at a position of a time corresponding to the drop position in the row (display region) of the medicine name. On the other hand, in a case where the medicine name correlated with the medicine region 62*a* is not in the column of the medicine name on the left side in the administration information display field 54, the row of the medicine name designated in the medicine region 62*a* is added to the administration information display field 54 with the drop operation of the medicine region 62*a*, and the numerical value indicating the dose is displayed in the added row.

In the administration information display field 54, medicine information scheduled to be used may be stored in correlation with the patient information or operation information to a patient, at the time of initial display of the administration information display field 54, the medicine information scheduled to be used may be read, rows of one or more medicines scheduled to be used are disposed, and a dose is input to a row corresponding to a medicine designated in a pallet. Alternatively, a configuration may be made in which a row corresponding to a medicine is disposed based on data regarding an administered medicine and a dose acquired from the ME equipment 32, and the dose is input to a row corresponding to a medicine designated in a pallet. A configuration may be made in which a row of a specific medicine is not disposed in the administration information display field 54 at first, a row of a medicine name designated in a pallet is added, and a dose is input to the added row.

In a case where the display of the administration information display field 54 is updated, the line segment 71 indicating the time corresponding to the drag position in the biological information display field 52, the time information 72, and the medicine information 73 shown in FIG. 4 are brought into non-display.

According to Embodiment 2, in a case of inputting information regarding medicines, events, or remarks, the user can perform recording on more accurate date and time focusing on, such as change in the vital graph, such as a rise in blood pressure in a case where a vasopressor is administered or a temporary stop of expiratory gas in a case where intubation is performed.

Here, although an example where the administration information is input ex post, the medicine region 62*a* may be input to the region of the current time with a drag-and-drop operation.

Although an example where the medicine region 62*a* is inserted into the biological information display field 52 has been described in FIGS. 4 and 5, the medicine region 62*a* of the input list 60 may be inserted into the supplementary information display field 56 or the supplementary region 64 of the input list 60 may be inserted into the administration information display field 54, and a flexible input of drag-and-drop free from a relationship between a type of an input item of a pallet and an item of the recording information display field 58 can be performed. The supplementary region 64 to be dragged on the input list 60 is an example of a "third region" in the present disclosure, and a region of a drop destination in the recording information display field 58 for the dragged supplementary region 64 is an example of a "fourth region" in the present disclosure. Even in a case where the supplementary region 64 is dragged to the recording information display field 58, similarly to the case of the medicine region 62*a* described referring to FIG. 4, the time information 72 and the content of the supplementary item are displayed on the right and left sides of the mouse position.

In the specification, the term "drag" includes a concept of designating a target region and moving in a state in which the target region is designated. The term "drop" includes a concept of selecting an insertion destination of the target region. In regard to the term "drag", moving the designated target region on the screen is not always required. For example, the medicine region 62*a* on the input list 60 may be designated by one click, the pointer may be moved in the designated state, and the region 70 may be selected by one click.

Designating a region, such as the medicine region 62*a*, on the input list 60 is included in the concept of the term "drag". Selecting a region, such as the region 70, on the recording information display field 58 is included in the concept of the term "drop". The description itself of the medicine region 62*a* may not be moved during drag. For example, in a case of an operation of an input using a touch panel, such as a tablet terminal, designating the medicine region 62*a* on the input list 60 with a touch operation and selecting the region 70 on the biological information display field 52 are included in the concept of drag-and-drop.

Embodiment 3

The mouse pointer is placed (mouseover) over the numerical value of the medicine dose on the pallet, whereby not only the administration unit of the numerical value displayed in the pallet but also doses converted into other units can be displayed.

FIG. 6 is a display example of doses in a plurality of units that are displayed in a case where a medicine region 62b on the input list 60 is designated. A dose correlated with the medicine region 62b of the input list 60 is 0.2 μ/k/m, and a numerical value "0.2" is labeled to the medicine region 62b. In a case where the mouse point is placed over the numerical value of the medicine region 62b, as shown in FIG. 6, a pop-up 80 where the dose of 0.2 μ/k/m correlated with the medicine region 62b, a value (0.63 mg/h) converted into units of mg/h, and a value (6.343 ml/h) converted into units of ml/h are simultaneously displayed in parallel.

The unit "μ/k/m" of the dose is an example of a "first unit" in the present disclosure, and "0.2 μ/k/m" as the numerical value in the unit is an example of a "first dose" in the present disclosure. Each of "mg/h" and "ml/h" is an example of a "second unit" in the present disclosure, and each of 0.63 mg/h and 6.343 ml/h is an example of a "second dose" in the present disclosure.

In FIG. 6, although the pop-up 80 is displayed in a pull-down manner below the medicine region 62b, the pop-up 80 may be displayed beside or above the medicine region 62b or may be displayed on the medicine region 62b in a superimposed manner. With this, it is possible to allow the user to confirm the doses in a plurality of units.

FIG. 7 shows another display example of doses in a plurality of units. As shown in an upper section of FIG. 7, in a case where a unit region 84 on a pallet is selected, as shown in a middle section of FIG. 7, a menu of other units is displayed in a pull-down manner. The user can select another unit from a pull-down menu 86. In a case where another unit is selected from the pull-down menu 86, as shown in a lower section of FIG. 7, numerical value information of a dose based on the selected unit is displayed. The numerical value information of the dose based on the selected unit may be displayed in a pallet format similarly to the pallet in the original unit, and a region 87 with numerical values may function as a pallet item on which an operation of drag-and-drop can be performed.

The numerical value information of the dose based on the unit relating to the selection may be displayed in parallel with the pallet of the dose in the original unit vertically or may be displayed on the display region of the pallet of the dose in the original unit in a superimposed manner.

Embodiment 4

The medicine list 63 in the input list 60 may be different in display form depending on a classification of a medicine. For example, the medicine type cell 63a in the medicine list 63 may be displayed with a background by color depending on the classification of the medicine disposed in the medicine type cell 63a. FIG. 8 is a display example showing a part of the input list 60. The backgrounds of the medicine type cells 63a of a plurality of medicines listed in the input list 60 are displayed by color, for example, with drug efficacy-specific color codes recommended by Japanese Society of Anesthesialogists. The drug efficacy-specific color codes are defined conforming to International Standard Correspondence (ISO26825). For example, a standard color code of a medicine syringe label is defined by drug efficacy in such a manner that an induction medicine is yellow, benzodiazepine is orange, a benzodiazepine antagonist is orange diagonal stripes, a muscle relaxant is red, and a neuromuscular antagonist is red diagonal stripes. A title of a medicine in the input list 60 is colored with the drug efficacy-specific color code, whereby improvement of visibility is achieved. A color of text indicating a medicine may be different depending on a classification of a medicine or text may be different in size or font. A display aspect of a row in correlation with a medicine including not only the medicine type cell 63a but also the unit cell 63b and a plurality of dose cells 63c may be different depending on a classification of a medicine.

Embodiment 5

In the medicine list 63 of the input list 60, a display aspect may be different depending on administration methods of medicines. For example, in the medicine list 63, characters indicating a medicine disposed in the medicine type cell 63a of a medicine to be administered by continuous administration and characters indicating a dose disposed in the dose cell 63c are displayed in thick characters, and characters indicating a medicine disposed in the medicine type cell 63a of a medicine to be administered by one-shot administration and characters indicating a dose disposed in the dose cell 63c are displayed in thin characters.

FIG. 9 is an enlarged view of a part of the input list 60. Like a region indicated by a surrounding frame line in FIG. 9, even for the same medicine, characters indicating a medicine name, an administration unit, and a dose in a row of the pallet to be input candidates in continuous administration are displayed in thick characters, and characters in a row of the pallet to be input candidates in one-shot administration are displayed in thin characters. In this case, the difference in administration method is differentiated by the difference in display format of characters, whereby improvement of visibility is expected. The size of characters of any one of the medicine type cell 63a or the dose cells 63c may be different depending on the administration method. The characters disposed in the medicine type cell 63a or the dose cells 63c or the color of background of the region may be different depending on the administration method.

Figure 10:
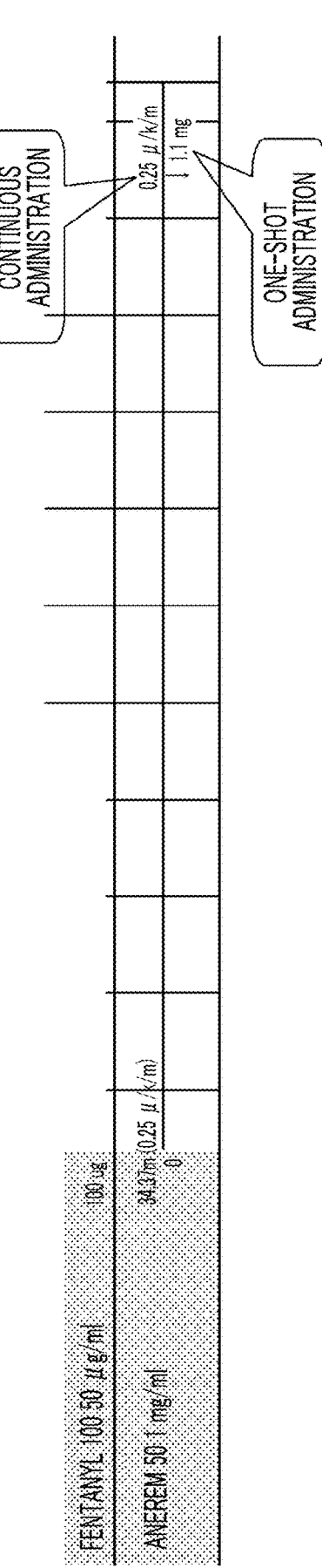
FIG. 10 is an enlarged view of a part of an administration information display field.

FIG. 10 is an enlarged view showing a part of the administration information display field 54. In the administration information display field 54, a display region is divided for each medicine, and information indicating a dose and an administration timing is displayed in the display region. Both administration methods of continuous administration and one-shot administration may be used. In a case of such a medicine, the display region of the medicine in the administration information display field 54 includes a continuous administration display region where information regarding continuous administration is displayed and a one-short administration display region where information regarding one-short administration is displayed.

For example, a display region of a dose regarding "ULTIVA 2 0.1 mg/ml" illustrated in FIG. 10 is classified into an upper section and a lower section, information regarding the dose in a case where continuous administration is performed is displayed in the continuous administration display region of the upper section, and information regarding the dose in a case where one-shot administration is performed is displayed in the one-shot administration display region of the lower section. Information regarding the dose in continuous administration may be displayed in the lower section, and information regarding the dose in one-shot administration may be displayed in the upper section.

In regard to an input of an end time in a case of continuous administration, the line segment 59 at the present time (current time) may be input or an administration end button (pallet) may be provided in the input list 60 and the administration end button may be dragged and dropped to input information for setting the end time.

Embodiment 6

A part of pallet items in the input list 60 can be highlighted. The term "highlighting" means making a display aspect different to achieve relative visual differentiation. The display format of the characters, such as thick characters and thin characters, is an example of a display aspect. A color of characters, a background color, font, addition of an underline or a symbol, or a combination of such elements may be elements that make the display aspect different. A region to be highlighted in the input list 60 and an instruction regarding the display aspect may be set by the user. Display setting regarding highlighting is an example of "display setting including an instruction for display in different display formats" in the present disclosure.

For example, a configuration may be made in which the mouse pointer is placed over a desired pallet item in the input list 60 and a right click is made, such that execution (on) and release (off) of highlighting can be switched. The on/off function of highlighting is implemented, whereby it is possible to use the on/off function of highlighting for the purpose of marking a pallet of a dose in the input list 60 that is highly likely to be used in a present operation, by highlighting in advance.

A configuration may be made in which a pallet item used once in the input list 60 is automatically highlighted. In an operation or the like, the same medicine is often repeatedly administered with the same dose by one-shot administration. Accordingly, it is convenient for the dose administered once being highlighted on the input list 60.

FIG. 11 shows an example of highlighting of pallet items. Each of a medicine pallet row indicated by a reference sign PLA of FIG. 11 and a medicine pallet row indicated by a reference sign PLB is an example of a display aspect in a state in which highlighting is released. The medicine pallet row of each of reference signs PL1 to PL5 illustratively shows variation of a display aspect in a state in which highlighting is executed.

As an aspect of highlighting, for example, like a first example of highlighting shown in the medicine pallet row PL1, a display aspect where "-" (hyphen) is attached before and after a number indicating a dose on a pallet may be employed.

The present disclosure is not limited to the first example, and like a second example shown in the medicine pallet row PL2, a display aspect where "_" (underscore) is attached before and after a number indicating a dose on a pallet may be employed.

In addition, like a third example shown in the medicine pallet row PL3 and a fourth example shown in the medicine pallet row PL4, a display aspect where a number indicating a dose on a pallet is underlined may be employed.

As an aspect of highlighting in a case of a medicine B to be administered by one-shot administration, for example, like a fifth example shown in the medicine pallet row PL5, a display aspect where "↑" (downward arrow) is attached before or after a number indicating a dose on a pallet may be employed.

In FIG. 11, although an example where each of four items (regions) in the row is highlighted for each of the medicine pallet rows PL1 to PL5 has been shown, only a part of regions in the row may be highlighted. Instead of or in combination with the display aspects illustrated in FIG. 11, a display aspect where the color of the characters is changed or the background color of the region is changed may be employed.

Embodiment 7

A maintenance function of performing various settings regarding the input list 60 can be used and a plurality of patterns of an input candidate group to be displayed in the input list 60 can be defined. The contents of pallet portions that are displayed as the input list 60 can be simply changed with selective switching or the like of combo boxes 66*a*, 66*b*, and 66*c*. The medical information management system 10 has a maintenance function capable of registering a pattern (hereinafter, referred to as a "pallet item pattern") of arrangement of pallet items to be displayed in the input list 60 in advance.

A pallet item pattern of each anesthesia method, a pallet item pattern of each operative method, or the like is set in advance using the maintenance function. With this, the pallet can be expanded to the input list 60 by creating any pallet item pattern and selecting a name (pallet pattern name) of a pallet item pattern depending on purposes or the like.

Figure 12:
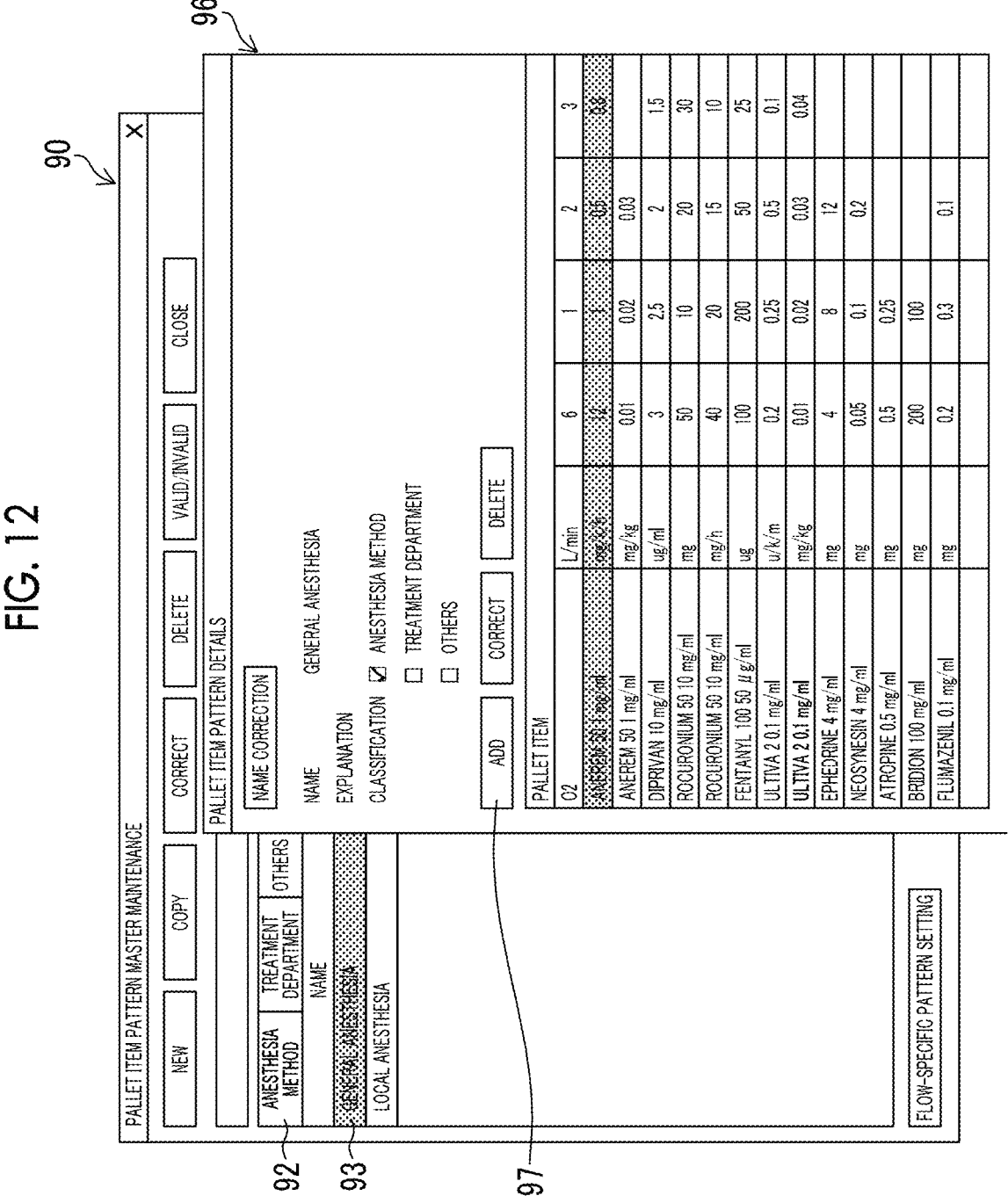
FIG. 12 is an example of a maintenance screen for various settings regarding the input list.

FIG. 12 is an example of a maintenance screen 90 for performing various setting regarding the input list 60. The medical information management system 10 includes a maintenance program that provides a maintenance function. The maintenance program may be provided as software for setting (maintenance tool) separate from the medical information management program or may be incorporated into the medical information management program as a module. Here, an example where the maintenance program separate from the medical information management program is configured will be described. The user can start the maintenance program to designate a medicine and a dose, an event, remarks, and the like to the pallet of the input list 60.

In a case where the maintenance function is started, the maintenance screen 90 shown in FIG. 12 is displayed. In the maintenance screen 90, sorting tabs 92 of pattern titles, such as an anesthesia method and a treatment department, are provided. FIG. 12 shows an example of a detailed setting screen 96 of a pallet item pattern of "general anesthesia" that is displayed in a case where the user selects the sorting tab 92 of "anesthesia method" to designate an item 93 of "general anesthesia" from among the anesthesia methods. Note that "general anesthesia" means "general anesthesia", and "local anesthesia" means "local anesthesia". Each of a plurality of pallet item patterns selectable with the sorting tab 92 is an example of a "list patter" in the present disclosure.

In the detailed setting screen 96, the user selects a target desired to be added to the pallet from a list of medicines, events, and remarks, and depresses a button 97. With this, a pallet item pattern (input candidate group) correlated with an anesthesia method and/or an operative method is registered. In regard to the starting of the maintenance function, a configuration may be made in which a "set button" (not shown) is displayed in an upper portion of the input list 60, and the user depresses the set button, such that the maintenance function is started.

FIG. 13 is a display example of the input list 60. FIG. 13 shows an example of a pallet that is displayed in the input list 60 in a case where "general anesthesia" and "Caesarean section" are selected from combo boxes 66*a* and 66*b* in an upper portion of the input list 60. "Caesarean section" is an example of an operative method. In this case, a pallet defined in a pallet item pattern of "general anesthesia" and "general anesthesia" is expanded to the input list 60.

Example of Operation Procedure for Registering Pallet Item Patten

An example of an operation procedure for registering a pallet item pattern using the maintenance function will be described referring to FIGS. 14 to 18.

Figure 14:
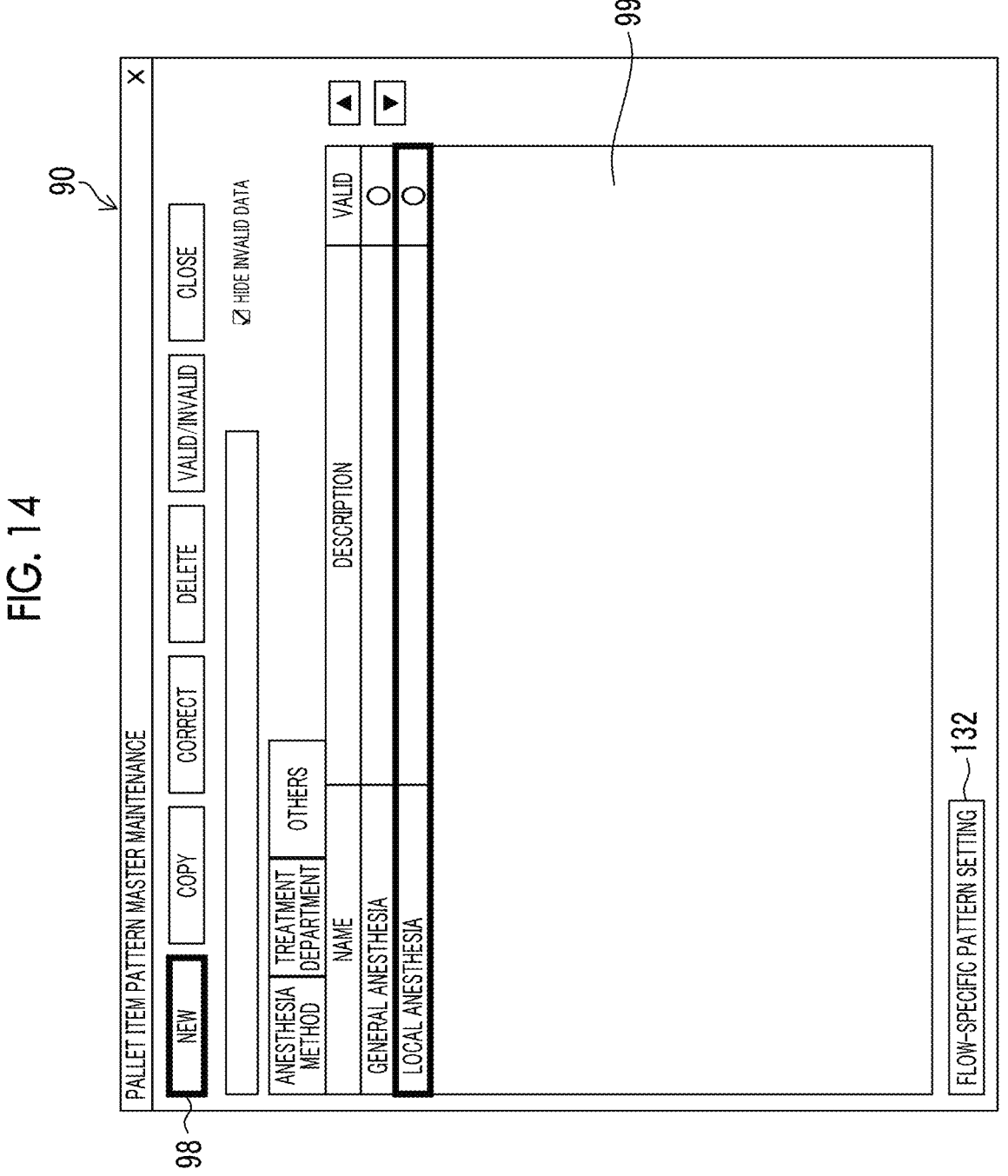
FIG. 14 is an example of the maintenance screen.
Figure 15:
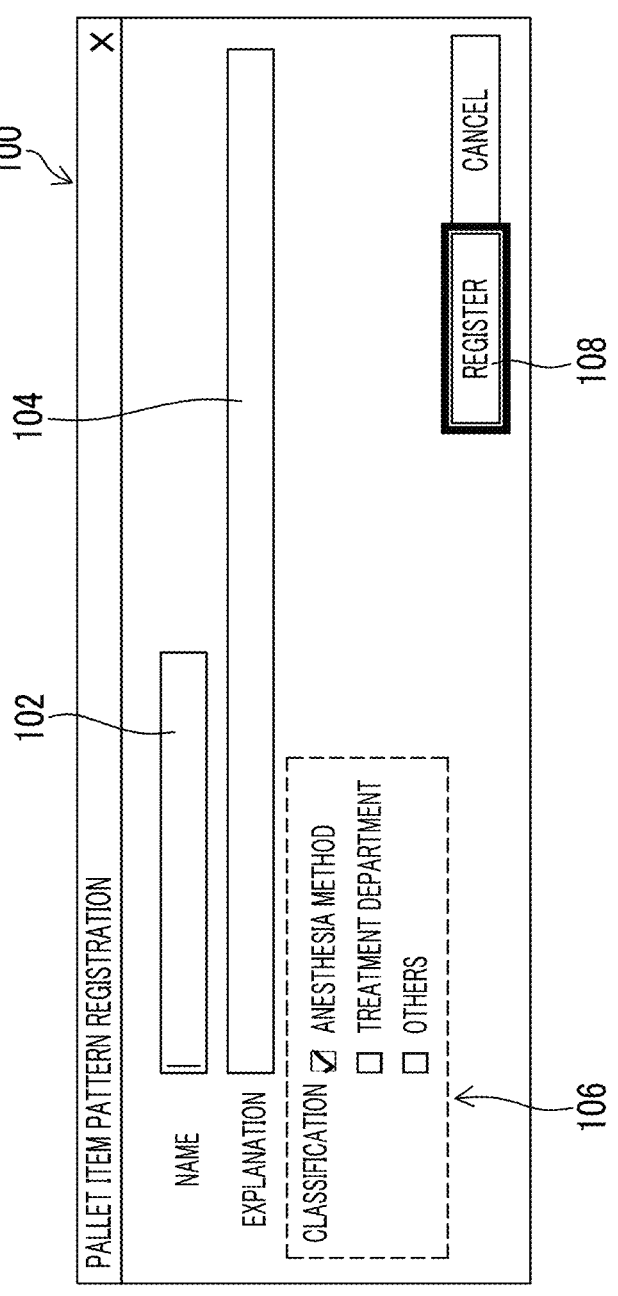
FIG. 15 is an example of a registration screen on which registration of a pallet item pattern is received.
Figure 16:
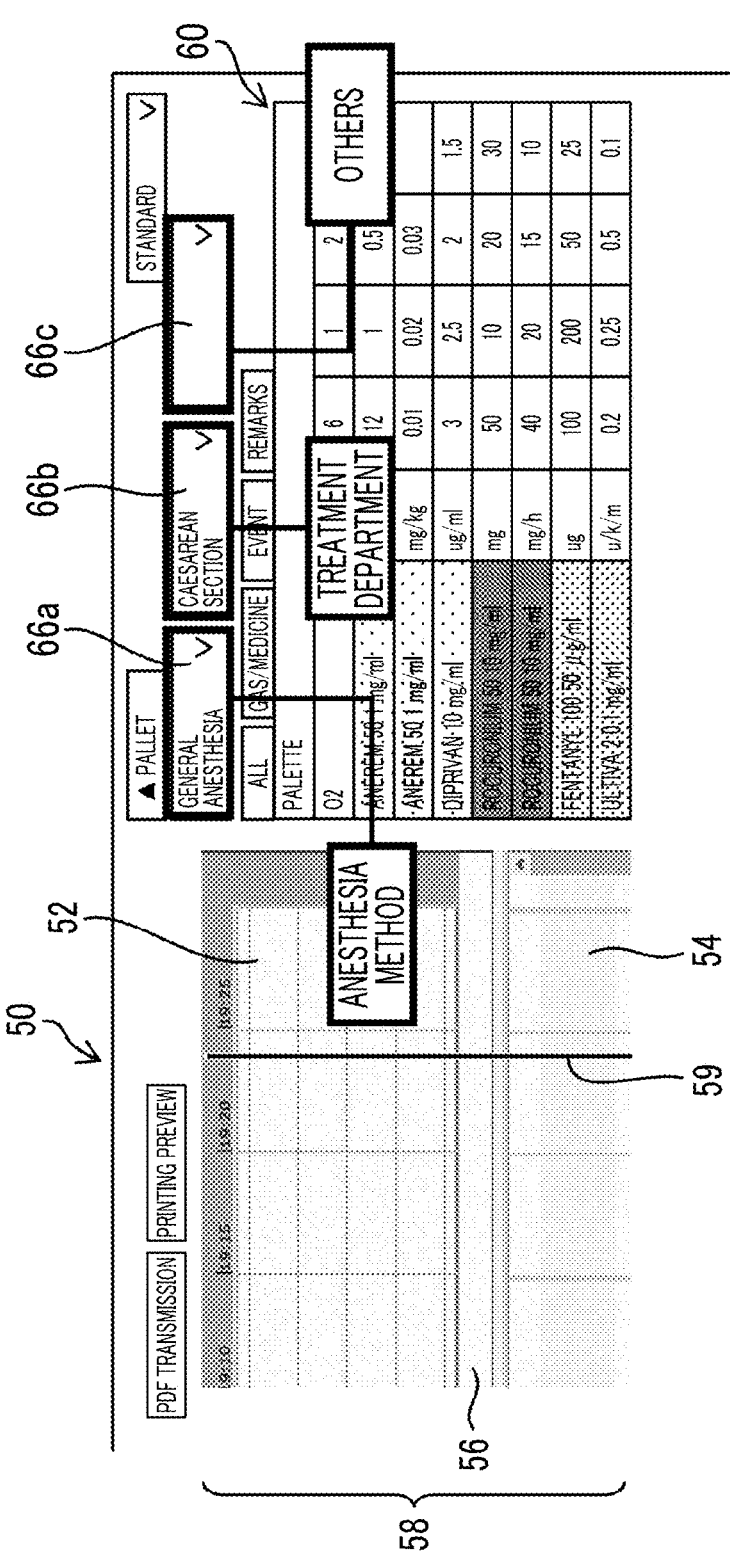
FIG. 16 is an explanatory view showing roles of combo boxes displayed in an upper portion of the input list.

In a case where a new button 98 of the maintenance screen 90 shown in FIG. 14 is depressed, a registration screen 100 shown in FIG. 15 is displayed. The registration screen 100 has a name input field 102, an explanation input field 104, and a check box 106 of classifications. The user inputs a name (pallet pattern name) of a new pallet item pattern to the name input field 102 and inputs explanation regarding the pallet item pattern to the explanation input field 104 as necessary. A plurality of classifications can be selected from "anesthesia method", "treatment department", and "others". The three types of classifications correspond to the three combo boxes 66a, 66b, and 66c displayed in the upper portion of the input list 60 of the anesthesia recording screen 50 as in FIG. 16, and the pallet item pattern to be newly added is displayed as an option in the selected combo boxes 66a, 66b, and 66c.

The user can register a new pallet pattern name by inputting necessary matters on the registration screen 100 of FIG. 15 and depressing a register button 108.

The maintenance screen 90 shown in FIG. 14 has a registered pattern list display field 99 where a list of registered pallet item patterns is displayed. FIG. 14 shows a state in which a pallet item pattern of "general anesthesia" and a pallet item pattern of "local anesthesia" are registered. A pallet item pattern added by new registration is listed in the registered pattern list display field 99.

Figure 17:
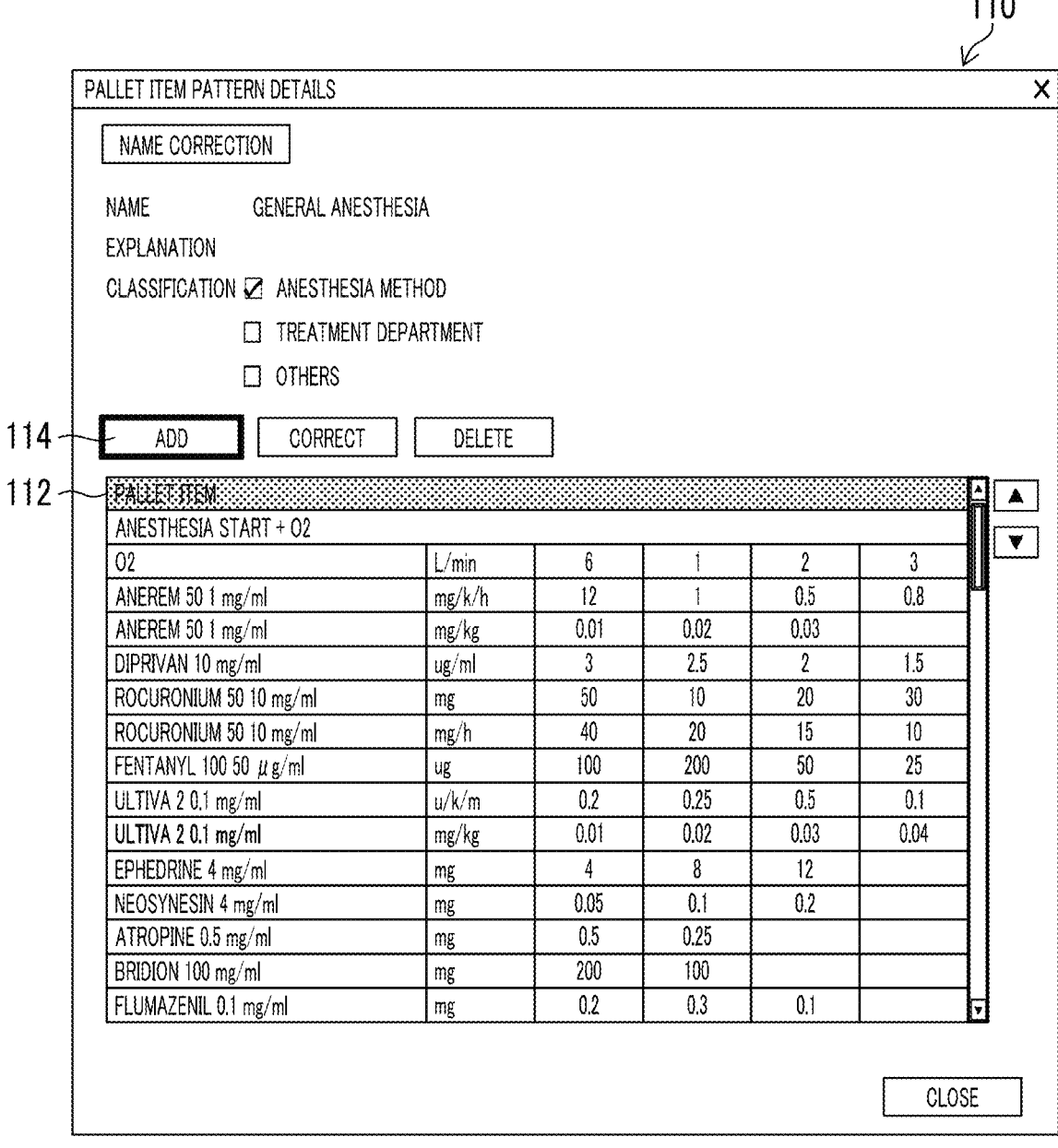
FIG. 17 is an example of a detailed setting screen of a pallet item pattern.

In a case where the pallet pattern name is newly registered from the registration screen 100 of FIG. 15 or selects a target pallet pattern name from the list of registered pallet item patterns, a detailed setting screen 110 of each pallet item pattern shown in FIG. 17 is displayed.

FIG. 17 is an example of the detailed setting screen 110 for the pallet item pattern of "general anesthesia". The detailed setting screen 110 has a pallet item list display field 112 where a list of pallet items (input items) defined in the pallet item pattern is displayed, and an add button 114.

Figure 18:
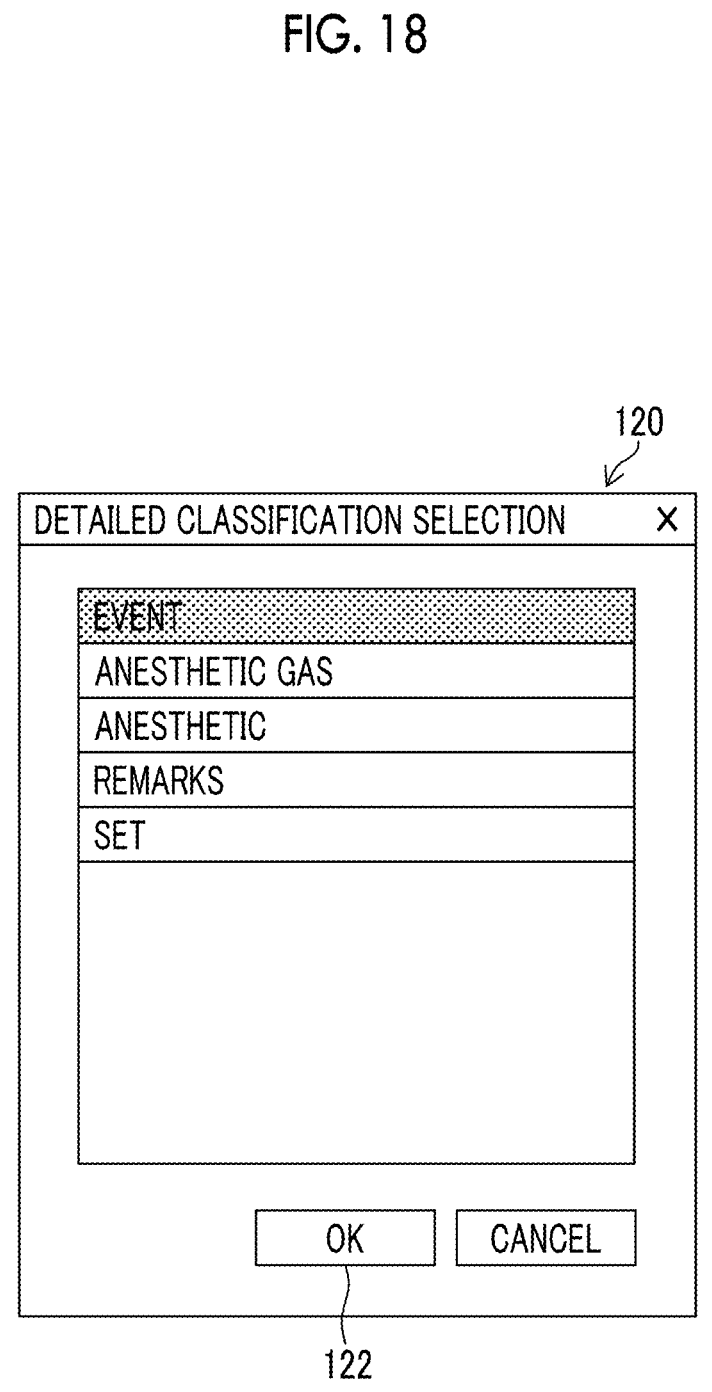

In a case of adding a pallet item, the user depresses the add button 114 to display a classification selection screen 120 shown in FIG. 18 and selects an item to be added. On the classification selection screen 120, for example, selection candidates of five types of classifications of "event", "anesthesia gas", "anesthetic", "remarks", and "set" are displayed. The user selects the classification of the pallet item to be added, depresses an OK button 122, and adds a pallet item.

For example, in a case of additionally creating a pallet item of a set of information for inputting a plurality of input items, such as a combination of a plurality of medicines or a combination of a medicine and an event, in a batch, the user selects "set" on the classification selection screen 120 of FIG. 18 to create the pallet item. The user can input detailed information, such as a dose or a type of an event, from the detailed setting screen (not shown) of each pallet item to define a pallet item and can add a new pallet item. The added pallet item is listed in the pallet item list display field 112 of FIG. 17.

Function of Setting Pallet Item for Each Login User

As described above, other than the aspect where the pallet item pattern is set for the anesthesia method or the operative method, a pallet item pattern may be set for each login user.

In this case, depending on a user who logs in to the medical information management system 10, a pallet item pattern associated with the user is automatically switched.

A user who uses the medical information management system 10 can register a pallet item pattern suitable for the user in advance, and a function of automatically selecting the pallet item pattern (combo boxes 66a, 66b, and 66c) in a case where the user logs in may be implemented.

Embodiment 8

A pallet item pattern can be automatically expanded for each type of an operation, such as an anesthesia method or an operative method. That is, the medical information management system 10 has a function of switching contents of pallet portions displayed as the input list 60 in conjunction with selection of an anesthesia method or an operative method.

The type of the operation, such as an anesthesia method or an operative method, is referred to as an "operation flow". The medical information management system 10 can associate the pallet item pattern with the operation flow, and can perform association setting of both the pallet item pattern and the operation flow in advance, thereby automatically selecting a pallet item pattern for each type of the anesthesia method or the operative method when the anesthesia recording screen 50 is opened. The pallet item pattern associated with the operation flow is referred to as a "flow-specific pattern".

Figure 19:
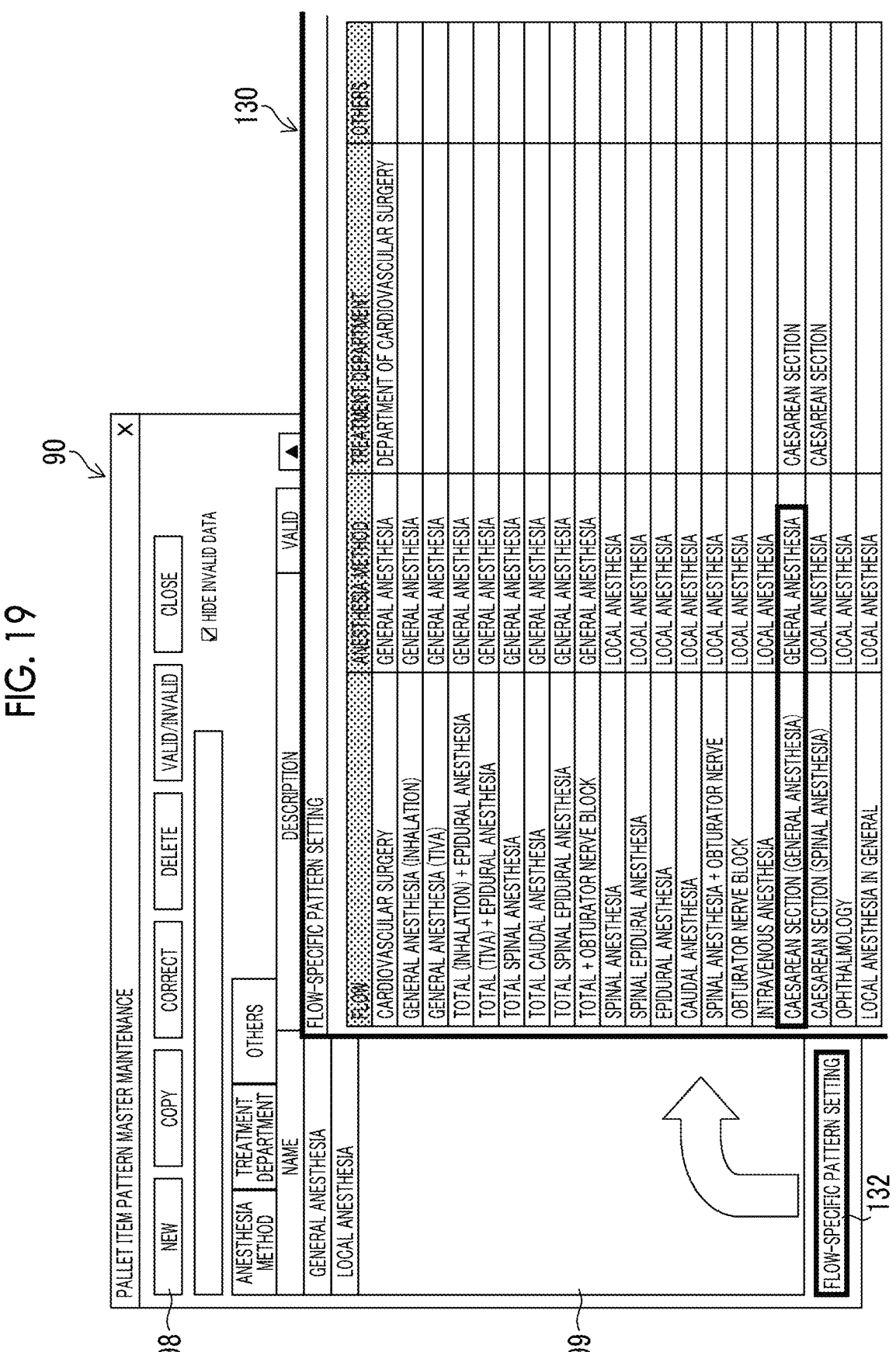
FIG. 19 is a screen example showing an example of an operation procedure for setting a flow-specific pattern.

FIG. 19 is an example of a flow-specific pattern setting screen 130 on which an input of setting of a flow-specific pattern is received. FIG. 19 shows an example where the flow-specific pattern setting screen 130 is displayed on the maintenance screen 90 in a superimposed manner. On the maintenance screen 90, a flow-specific pattern set button 132 is provided.

In a case where the flow-specific pattern set button 132 is depressed, the flow-specific pattern setting screen 130 is opened. The user can select an operation flow to be set from the flow-specific pattern setting screen 130 and can perform setting of a pallet item pattern that is initially displayed in the input list 60. A specific operation procedure example will be described below (FIGS. 22 to 25).

Figure 20:
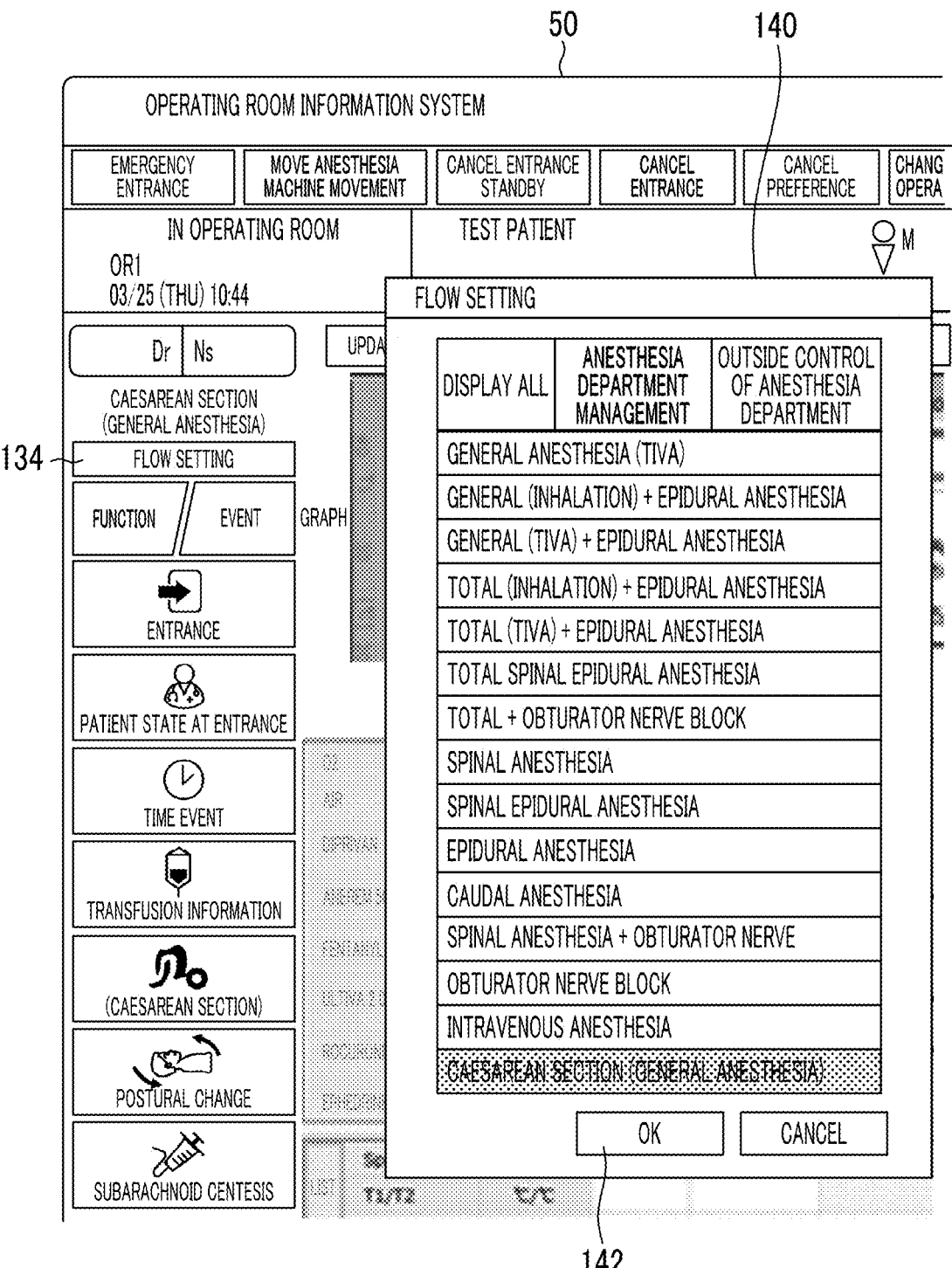
FIG. 20 is an example of a flow setting screen for setting an operation flow in the anesthesia recording screen.

FIG. 20 is an example of a flow setting screen 140 for setting an operation flow on the anesthesia recording screen 50. In a case where a flow set button 134 of the anesthesia recording screen 50 is depressed, the flow setting screen 140 is opened. On the flow setting screen 140, candidates of a plurality of operation flows are displayed in a list. The user can select an operation flow to be applied to the target patient from the list display and can depress an OK button 142, thereby setting the operation flow.

FIG. 21 is an example of an input list 60 that is displayed in association with the operation flow. FIG. 21 is an example of a pallet that is displayed in a case where an operation flow "Caesarean section (general anesthesia)" is set. In a case where "Caesarean section (general anesthesia)" is selected on the flow setting screen 140 of FIG. 20, and the OK button 142 is depressed, as shown in FIG. 21, a pallet item pattern associated with the operation flow "Caesarean section (general anesthesia)" is expanded to the input list 60.

Example of Operation Procedure in Case of Setting Flow-Specific Pattern

Here, an example of an operation procedure in a case of setting a flow-specific pattern will be described.

Figure 22:
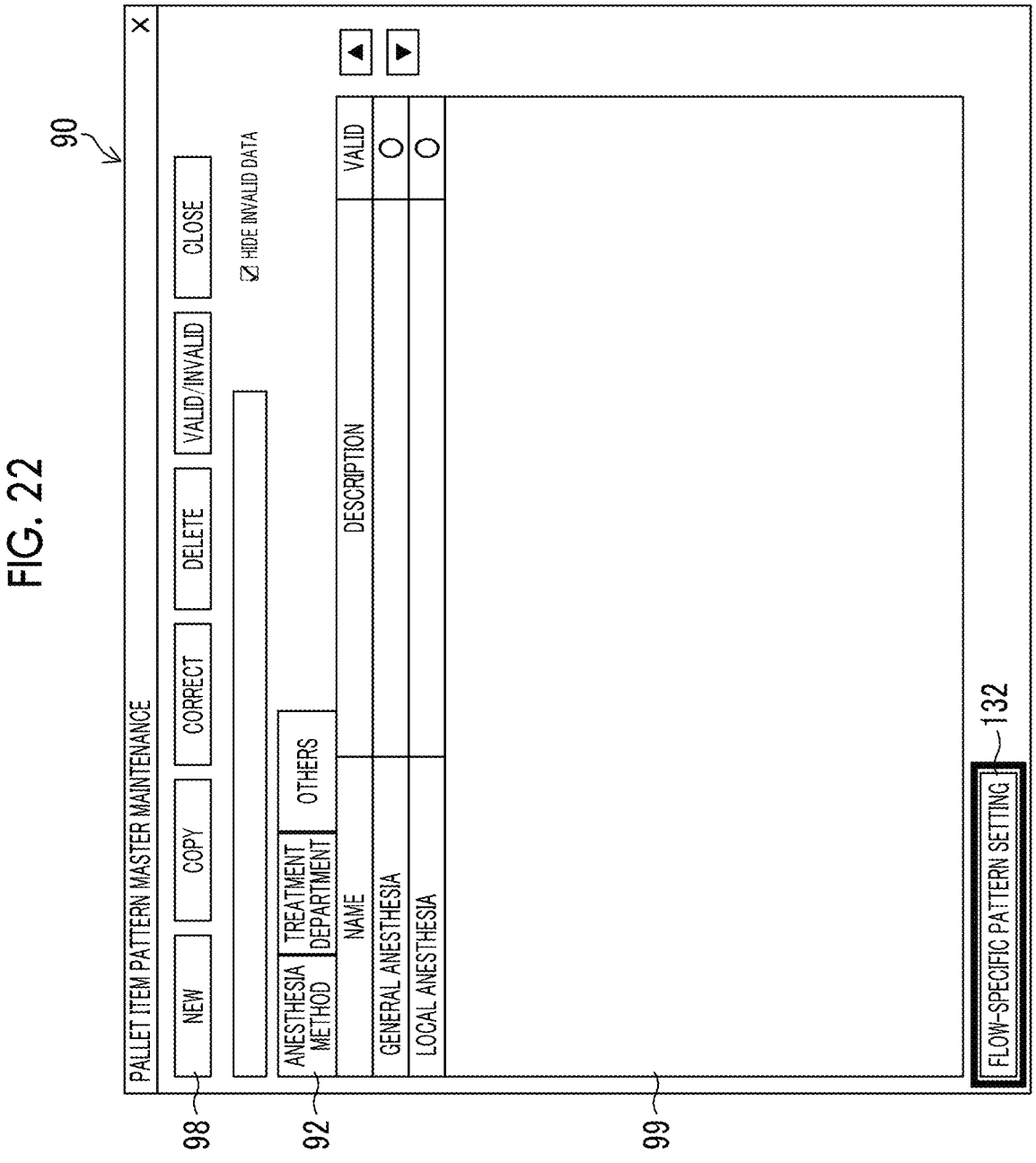
FIG. 22 is an example of a maintenance screen.

In a case of setting a flow-specific pattern, the user depresses the flow-specific pattern set button 132 of the maintenance screen 90 shown in FIG. 22. In a case where the flow-specific pattern set button 132 is depressed, the flow-specific pattern setting screen 130 shown in FIG. 23 is opened.

The user double-clicks an operation flow for which an initial display pattern is desired to be set, from the list of operation flows displayed on the flow-specific pattern setting screen 130. With the operation, a flow-specific pattern registration screen 150 shown in FIG. 24 is displayed.

FIG. 24 is an example of the flow-specific pattern registration screen 150. FIG. 24 shows an example of the flow-specific pattern registration screen 150 that is displayed in a case where an item "total (TIVA)+epidural anesthesia" is double-clicked from the flow-specific pattern setting screen 130 of FIG. 23. On the flow-specific pattern registration screen 150, a pallet item pattern that is initially displayed in each of "anesthesia method", "treatment department", and "others" is selected. "Total (TIVA)" means total intravenous anesthesia. "Epidural anesthesia" means epidural anesthesia.

Figure 25:
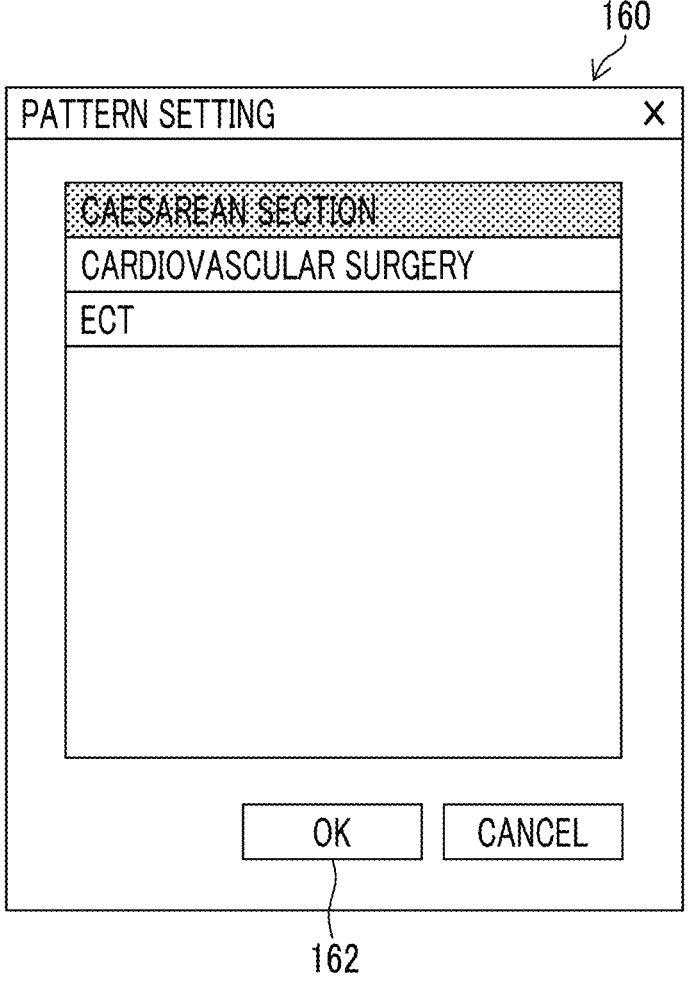
FIG. 25 is an example of a pattern setting screen.

For example, in a case where a select button 154 beside an input field 152 of "treatment department" in FIG. 24 is depressed, a pattern setting screen 160 shown in FIG. 25 is displayed. In a case where a pattern (for example, an item "Caesarean section") is selected from a list of candidates displayed on the pattern setting screen 160 and an OK button 162 is depressed, the pattern (for example, "Caesarean section") relating to the selection is input to the input field 152 of "treatment department" of the flow-specific pattern registration screen 150 shown in FIG. 24.

In a case where a register button 156 of the flow-specific pattern registration screen 150 shown in FIG. 24 is depressed, the flow-specific pattern is registered.

Embodiment 9

In the input list 60, different types of input items, such as medicines, events, and remarks, can be displayed in parallel on one screen. The input list 60 can display a plurality of pallets categorized for each type, such as "medicine", "event", and "remarks". That is, in the input list 60, all input items, such as medicines and events, can be displayed in parallel or only a specific category, such as medicines or events, can be narrowed down and displayed.

FIG. 26 is an example of an input list 60 that displays all types of pallet items including medicines, events, and remarks. The input list 60 has, for example, four types of tabs 171, 172, 173, and 174 of "all", "gas/medicine", "event", and "remarks", and display of a type corresponding to a tab of a selected pallet classification is performed.

In a case where the tab 171 of "all" is selected, as in FIG. 26, all types of pallet items are displayed in a list. The contents that are not displayed on one screen can be displayed by operating a knob of a scroll bar 176 or upper and lower arrows to moving the display region.

FIG. 27 is an example of an input list 60 that displays pallet items sorted in the category of medicines. In a case where the tab 172 of "gas/medicine" is selected, as in FIG. 27, pallet items that belong to the category of medicines are displayed in a list.

FIG. 28 is an example of an input list 60 that displays pallet items sorted into the category of events. In a case where the tab 173 of "event" is selected, as in FIG. 28, pallet items that belong to the category of events are displayed in a list.

Though not shown, in a case where the tab 174 of "remarks" is selected, pallet items that belong to the category of remarks are displayed in a list.

In Embodiment 10 described below, in a case where pallet items for which a set of a plurality of input items of different categories, such as a set of input items of medicines and events, is defined are registered, the pallet items of the set may be handled as pallet items that belong to a category of each of a plurality of input items. In a case where the pallet items with a set of a plurality of input items defined are registered, a tab "set" (not shown) may be provided in the input list 60. In a case where the tab "set" is selected, the pallet items of the set are displayed in a list.

Embodiment 10

A set of information regarding a plurality of medicines can be correlated with one pallet item. Not only medicines are made in a set, but also a medicine and an event, a medicine and remarks, or the like can be made in a set and can be correlated with one pallet, and a set of information of a plurality of input items can be simultaneously input with a drag-and-drop operation of one pallet item.

According to Embodiment 10, for example, a medicine and an event can be made in a set and simultaneously registered as a set, such as starting gas administration simultaneously with inhalation anesthesia start or administering a local anesthetic simultaneously with epidural anesthesia start.

Figure 29:
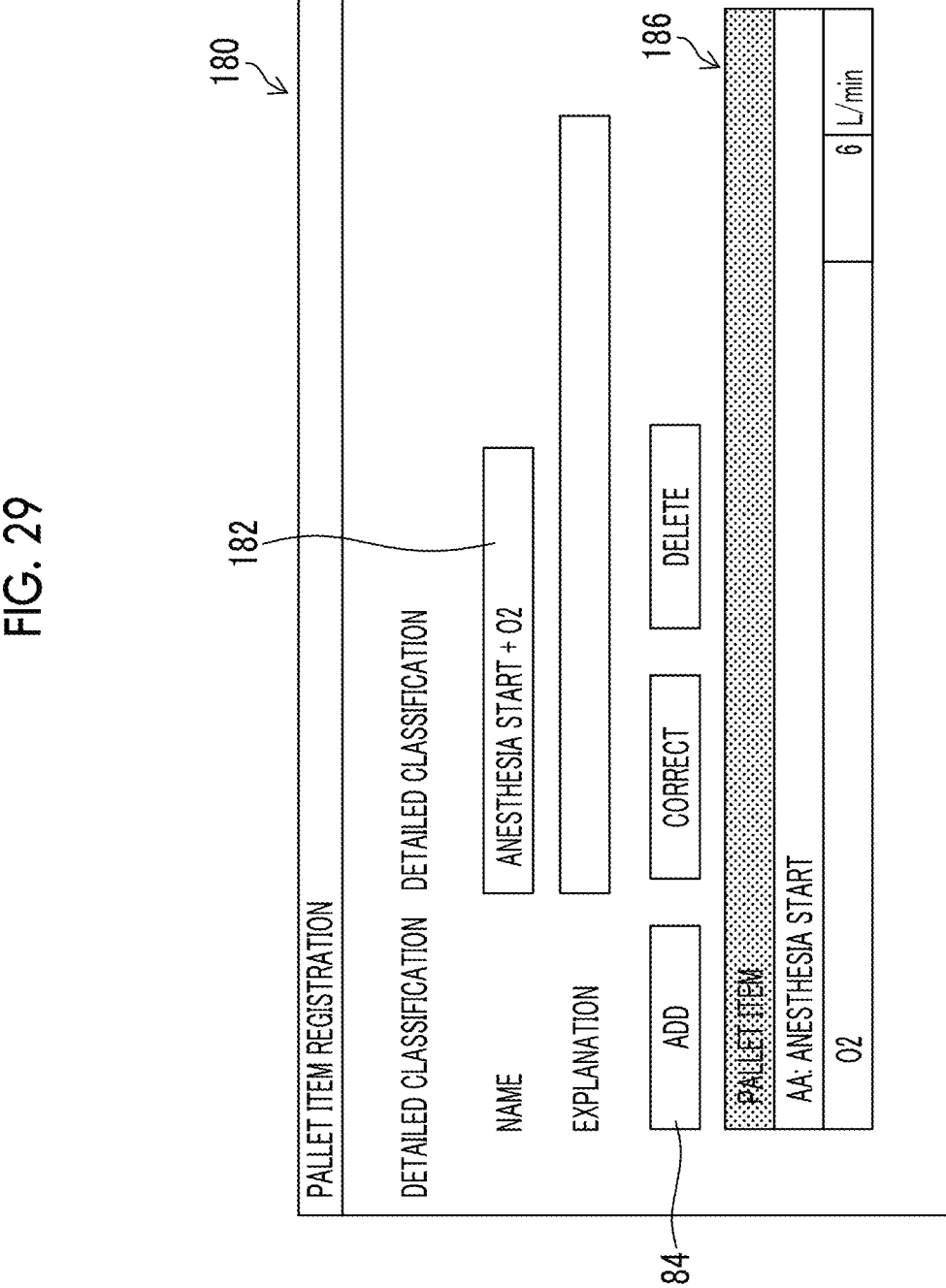
FIG. 29 is an example of a pallet item registration screen in a case of registering pallet items with a plurality of input items made in a set.

FIG. 29 is an example of a pallet item registration screen 180 in a case of registering pallet items with a plurality of input items made in a set. As described referring to FIGS. 14 to 18, "set" is selected on the classification selection screen 120 of FIG. 18 to create pallet items using the maintenance function.

In a case where "set" is selected on the classification selection screen 120 of FIG. 18, the pallet item registration screen 180 shown in FIG. 29 is displayed. The user can input a name (set name) of a set of pallet items to a name input field 182 and can depress an add button 184 to set items of pallet items to be specifically associated with respect to the set name. Then, the input items made in a set are listed in a pallet item display field 186.

FIG. 29 shows an example where a set name "anesthesia start+02" is input to the name input field 182, and combination information of an event of anesthesia start and administration (dose 6 L/min) of oxygen is defined with respect to the set name. The pallet items with a plurality of input items made in a set are displayed in the input list 60.

Figure 30:
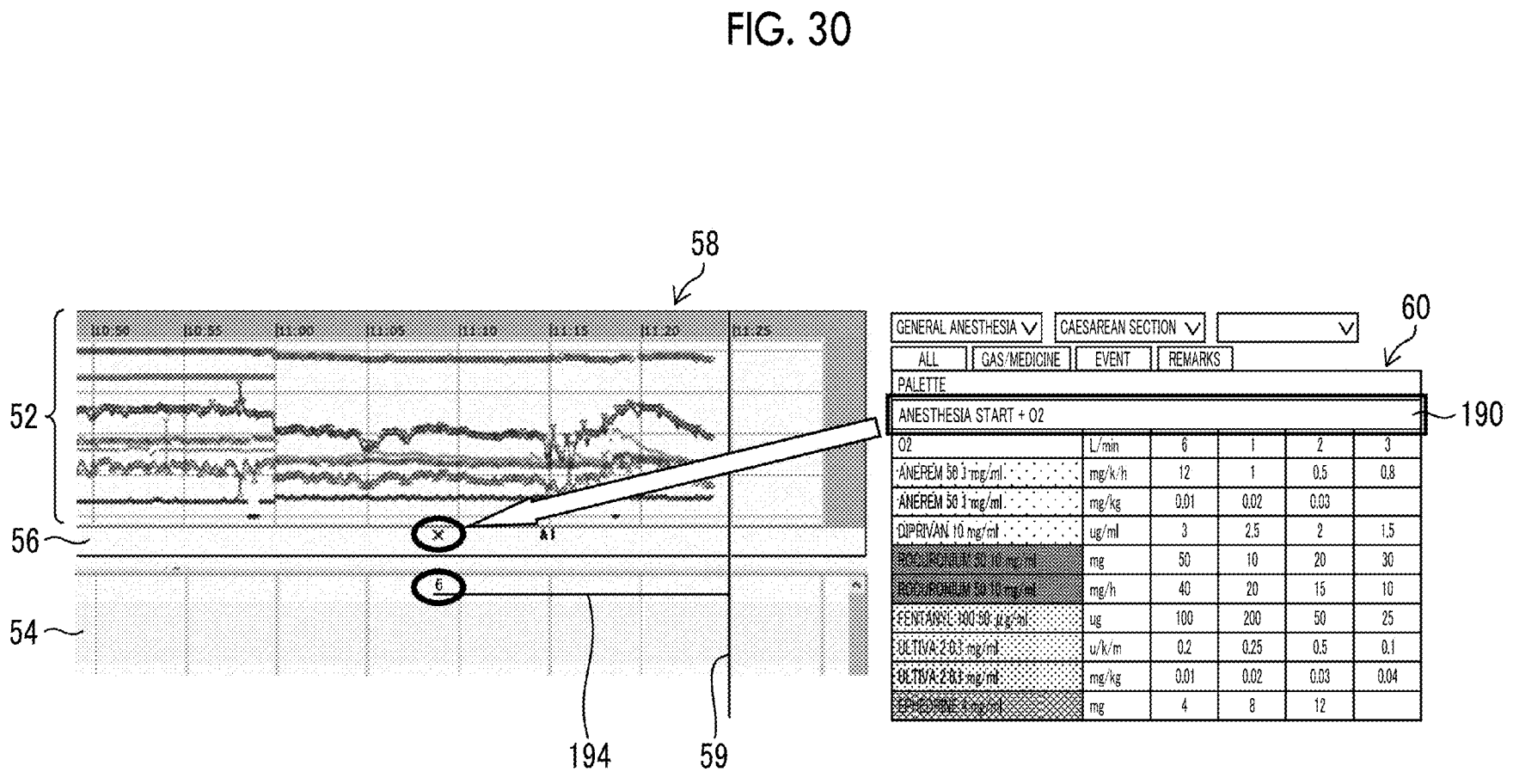

FIG. 30 is an explanatory view showing an example of a case of simultaneously inputting a plurality of input items made in a set to the pallet. For example, in a case where a set region 190 of "anesthesia start+02" is dragged from the input list 60 and is dropped to a region on the recording information display field 58, anesthesia is started at a time corresponding to the drop position, information indicating that oxygen is administered with 6 L/min is added to update the supplementary information and the administration information, and the display of the supplementary information display field 56 and the display of the administration information display field 54 are updated. The region of the drop destination in the recording information display field 58 for the set region 190 is an example of a "fifth region" in the present disclosure.

In the example of FIG. 30, a symbol (x) indicating the event of anesthesia start is displayed in the supplementary information display field 56, a character "6" indicating an oxygen dose is displayed in the display region of oxygen (O2) of the administration information display field 54, and a line 194 indicating that oxygen is in continuous administration is displayed. The types of the input items and the number of input items are not particularly limited. The pallet items made in a set are used, whereby it is possible to input a plurality of input items in a batch with a single drag-and-drop operation.

Example of Input Operation without Using Pallet

The medical information management system 10 also has a function of a manual input without using the pallet, in addition to the pallet input function. The user can input administration information, event information, and remarks information without using the pallet.

Figure 31:
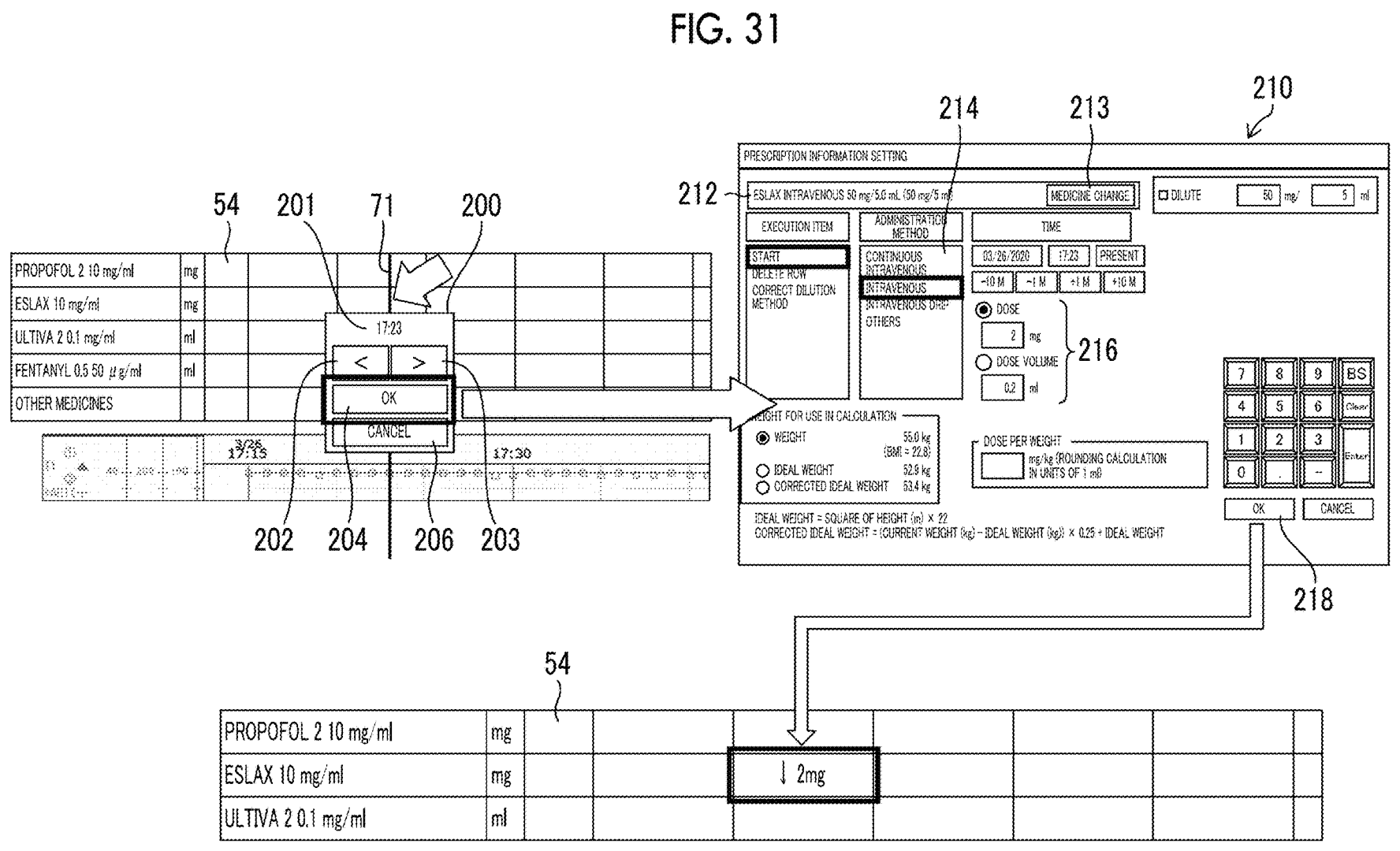

Example of Operation Procedure of Administration Information Input without Using Pallet FIG. 31 is a screen transition diagram showing an example of an operation procedure in a case of inputting administration information without using the pallet. The user can manually input the administration information with the following operation procedures 1A to 5A.

Procedure 1A: The user clicks any position on the administration information display field 54. In a case of inputting information regarding a medicine displayed in a medicine column of the administration information display field 54, a click is made on a medicine row of the target medicine in the administration information display field 54, and a medicine name input field 212 in an administration information input screen 210 described below is automatically input.

With the click operation, a time designation menu 200 and a line segment 71 are displayed at the click position. The time designation menu 200 includes a time display field 201, adjust buttons 202 and 203, an OK button 204, and a cancel button 206. In the time display field 201, a time corresponding to a click position is initially displayed.

Procedure 2A: The user operates the adjust buttons 202 and 203 to adjust a time. With the adjustment of the adjust buttons 202 and 203, a time of the time display field 201 and a position of the line segment 71 are updated.

Procedure 3A: In a case where the user depresses the OK button 204 in a state in which a desired time is designated, the administration information input screen 210 is displayed. The administration information input screen 210 includes a medicine name input field 212, an administration method selection field 214, a dose input field 216, and an OK button 218. In the medicine name input field 212, the medicine name of the medicine row corresponding to the click position of the administration information display field 54 is initially displayed with an automatic input.

Procedure 4A: In a case of changing the medicine name, the user can depress the change button 213 to display a pull-down menu (not shown) and can select a medicine name from the pull-down menu. The user can also add a new medicine name that is not in the pull-down menu. The user selects a medicine name and an administration method and inputs a dose on the administration information input screen 210.

Procedure 5A: After the input of each item on the administration information input screen 210 ends, the user depresses the OK button 218 to confirm the setting and registers the administration information.

Thus, in a case where the administration information is registered, the display of the administration information display field 54 is updated reflecting the registered administration information. In a lower section of FIG. 31, a display example of the administration information display field 54 in a state in which the administration information is registered with the procedure 5A is shown. In this example, in reflection of the setting confirmed on the administration information input screen 210, as surrounded by a thick-line quadrangular frame, information indicating a dose of one-shot administration of "↑2 mg" is displayed in a display region (medicine row) of a medicine name of "ESLAX 10 mg/ml" in the administration information display field 54.

Example of Operation Procedure of Event Information without Using Pallet

Figure 32:
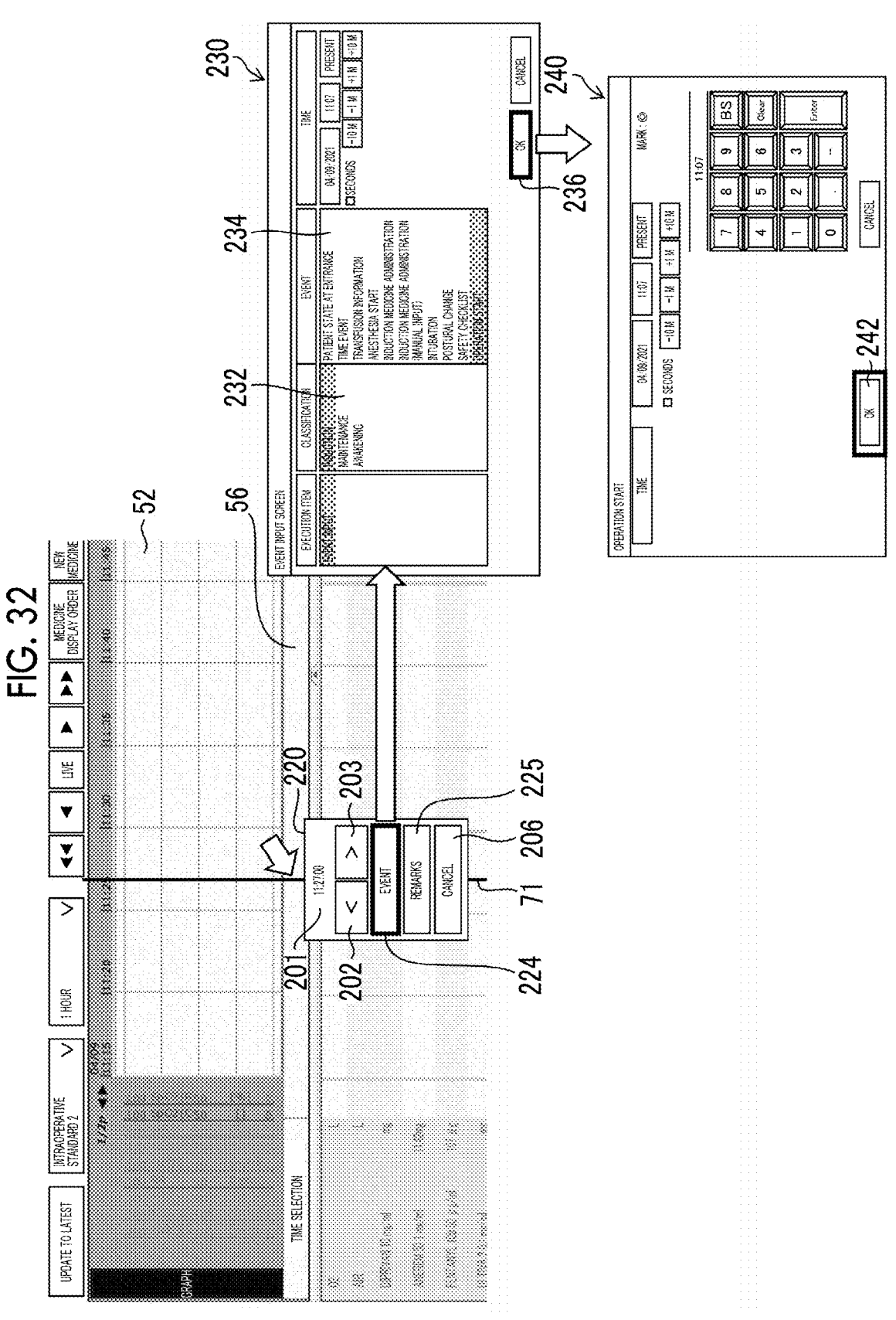
FIG. 32 is a screen transition diagram showing an example of an operation procedure in a case of inputting event information without using a pallet.

FIG. 32 is a screen transition diagram showing an example of an operation procedure in a case of inputting event information without using the pallet. The user can manually input the event information with the following operation procedures 1B to 5B.

Procedure 1B: The user clicks any position of the supplementary information display field 56. With the click operation, a time designation menu 220 and a line segment 71 are displayed at the click position. The time designation menu 220 includes a time display field 201, adjust buttons 202 and 203, an event button 224, a remarks button 225, and a cancel button 206. The roles of the time display field 201 and the adjust buttons 202 and 203 are as described referring to FIG. 31.

Procedure 2B: The user operates the adjust buttons 202 and 203 to adjust a time.

Procedure 3B: In a case where the user depresses the event button 224 in a state in which a desired time is designated, an event input screen 230 is displayed. The event input screen 230 includes a classification selection field 232 for selecting a classification of an event, an event selection field 234 for selecting an event item, and a select button 236. In the event selection field 234, types of events belonging to (sorted into) a classification selected in the classification selection field 232 are displayed.

Procedure 4B: The user selects a type of an event from the event selection field 234 on the event input screen 230 and depresses the select button 236.

Procedure 5B: In a case where the select button 236 is depressed, a confirmation screen 240 of the event relating to the selection is displayed. The user confirms a time of the event on the confirmation screen 240 and depresses the OK button 242. The user can correct the time of the event on the confirmation screen 240.

Thus, in a case where the event information is registered, the display of the supplementary information display field 56 is updated reflecting the registered event information, and a mark, a strip, or the like representing the type of the event is displayed in the supplementary information display field 56.

Figure 33:
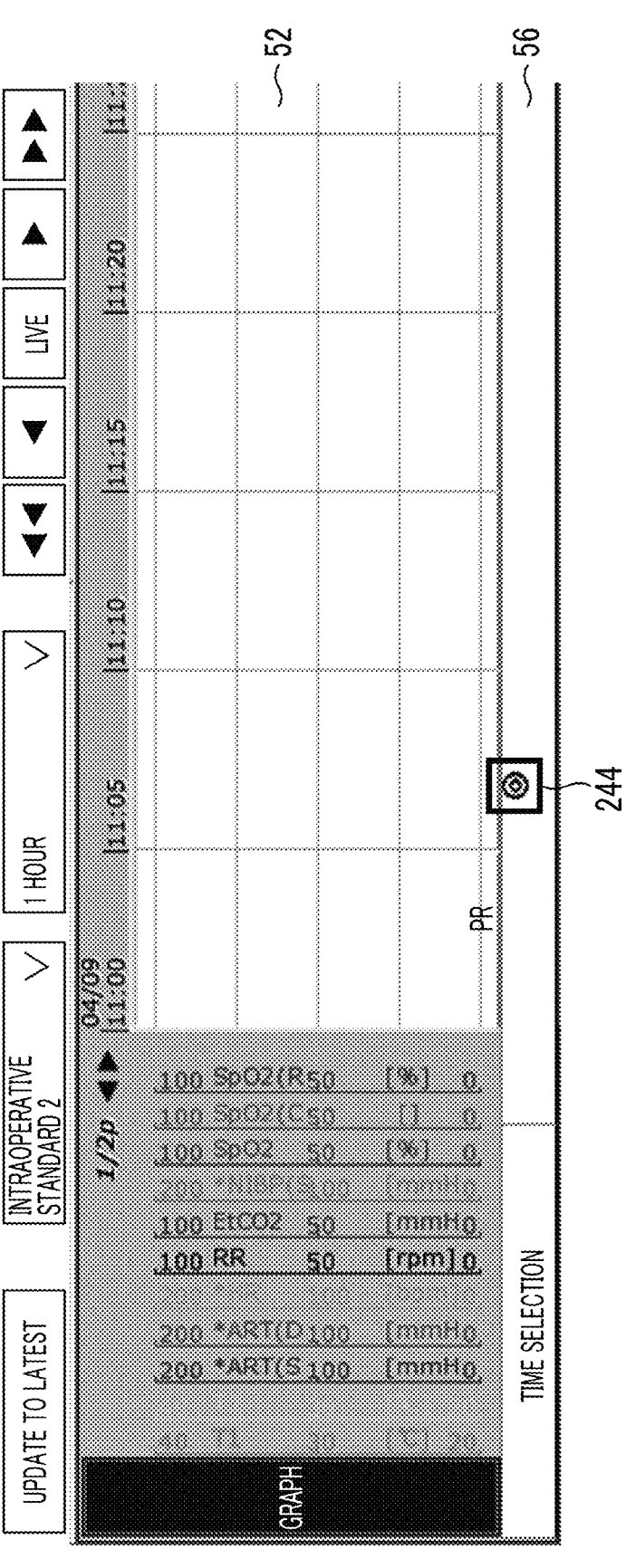
FIG. 33 is a display example of a supplementary information display field in a state in which the event information is registered.

FIG. 33 shows a display example of the supplementary information display field 56 in a state in which the event information is registered with the procedure 5B. In this example, in reflection of the content of the event confirmed through the event input screen 230 and the confirmation screen 240, a double circle mark 244 representing the event "operation start" is displayed at the time in the supplementary information display field 56.

Figure 34:
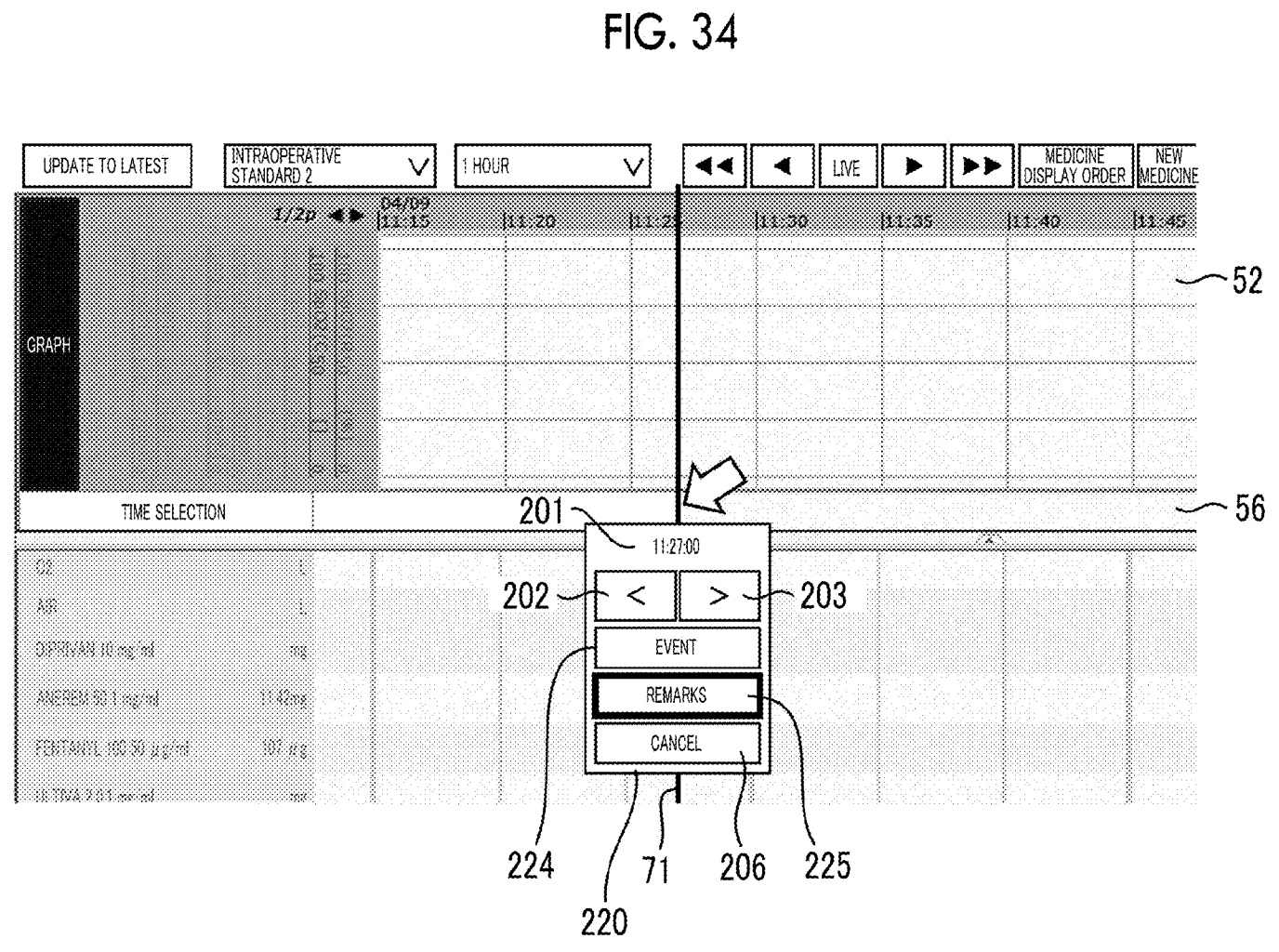

Example of Operation Procedure of Inputting Remarks Information without Using Pallet FIG. 34 is an example of a screen in a case of inputting remarks information without using the pallet. The user can manually input the remarks information with the following operation procedures 1C to 5C.

Procedure 1C: The user clicks any position of the supplementary information display field 56. As described referring to FIG. 32, with the click operation, the time designation menu 220 and the line segment 71 are displayed at the click position.

Procedure 2C: The user operates the adjust buttons 202 and 203 to adjust a time.

Figure 35:
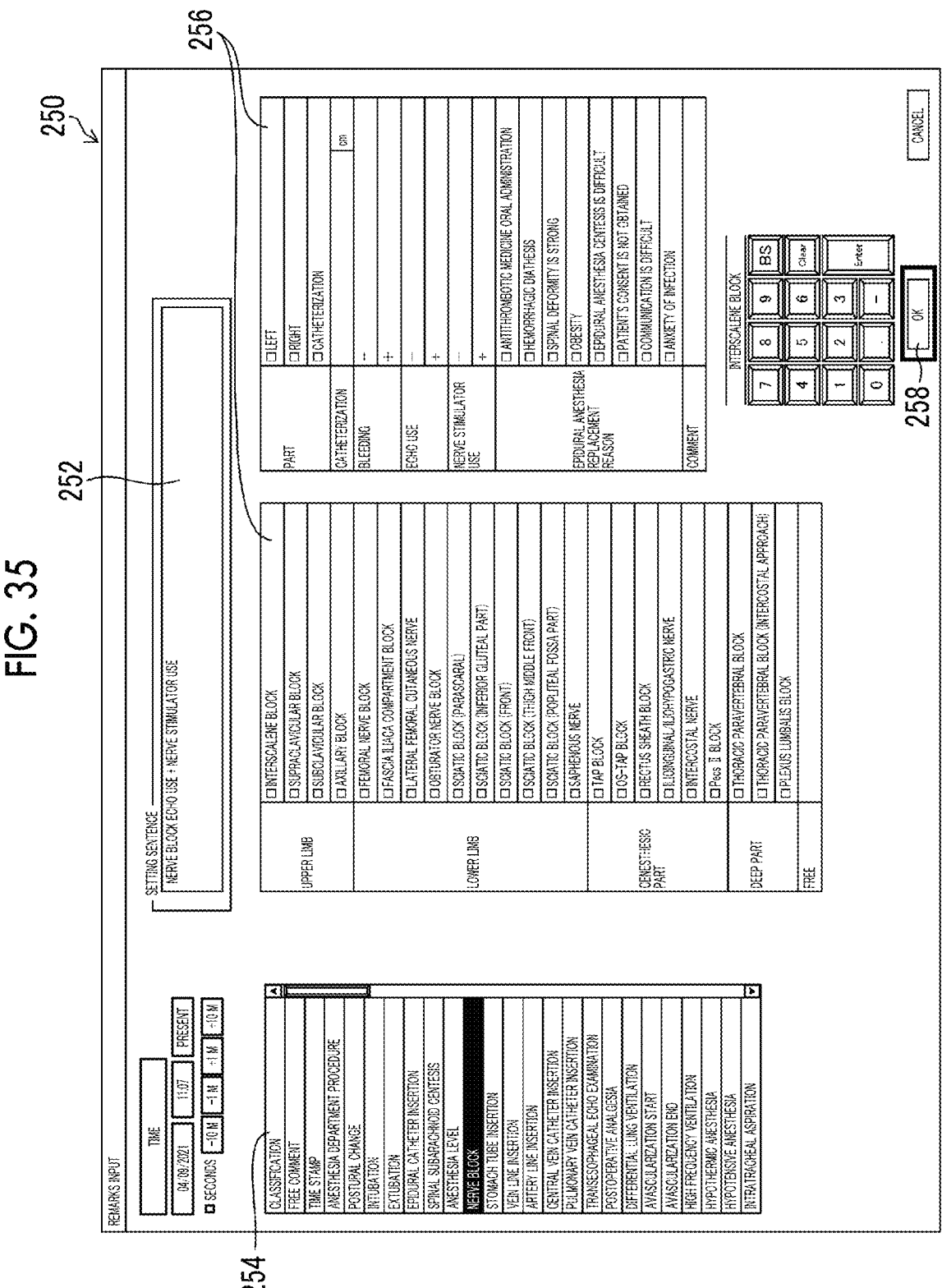
FIG. 35 is an example of a remarks input screen.

Procedure 3C: In a case where the user depresses the remarks button 225 in a state in which a desired time is designated, a remarks input screen 250 shown in FIG. 35 is displayed. The remarks input screen 250 includes a setting sentence display field 252 of remarks, a classification selection field 254, a template selection field 256, and an OK button 258. In the classification selection field 254, selection candidates of classifications of the contents of remarks are displayed. In the template selection field 256, options, such as a plurality of words and phrases and symbols, usable for creating a setting sentence are displayed. In the template selection field 256, only options selectable corresponding to an item selected in the classification selection field 254 may be displayed or selectable options may be differentiated.

Procedure 4C: The user can create a sentence (setting sentence) of remarks with an input of a template format for selecting the item from the selection candidates displayed in the classification selection field 254 and the template selection field 256. The created sentence is displayed in the setting sentence display field 252. An input of directly writing a sentence to the setting sentence display field 252 may be performed without depending on the template format.

Procedure 5C: After creating the setting sentence, the user confirms a time of a matter relating to remarks and depresses the OK button 258.

Thus, in a case where the remarks information is registered, the display of the supplementary information display field 56 is updated reflecting the registered remarks information, and a symbol corresponding to the remarks information is displayed at a position of a target time of a remarks display region in the supplementary information display field 56. The remarks display region may be, for example, a region of a lower portion of the biological information display field 52.

Figure 36:
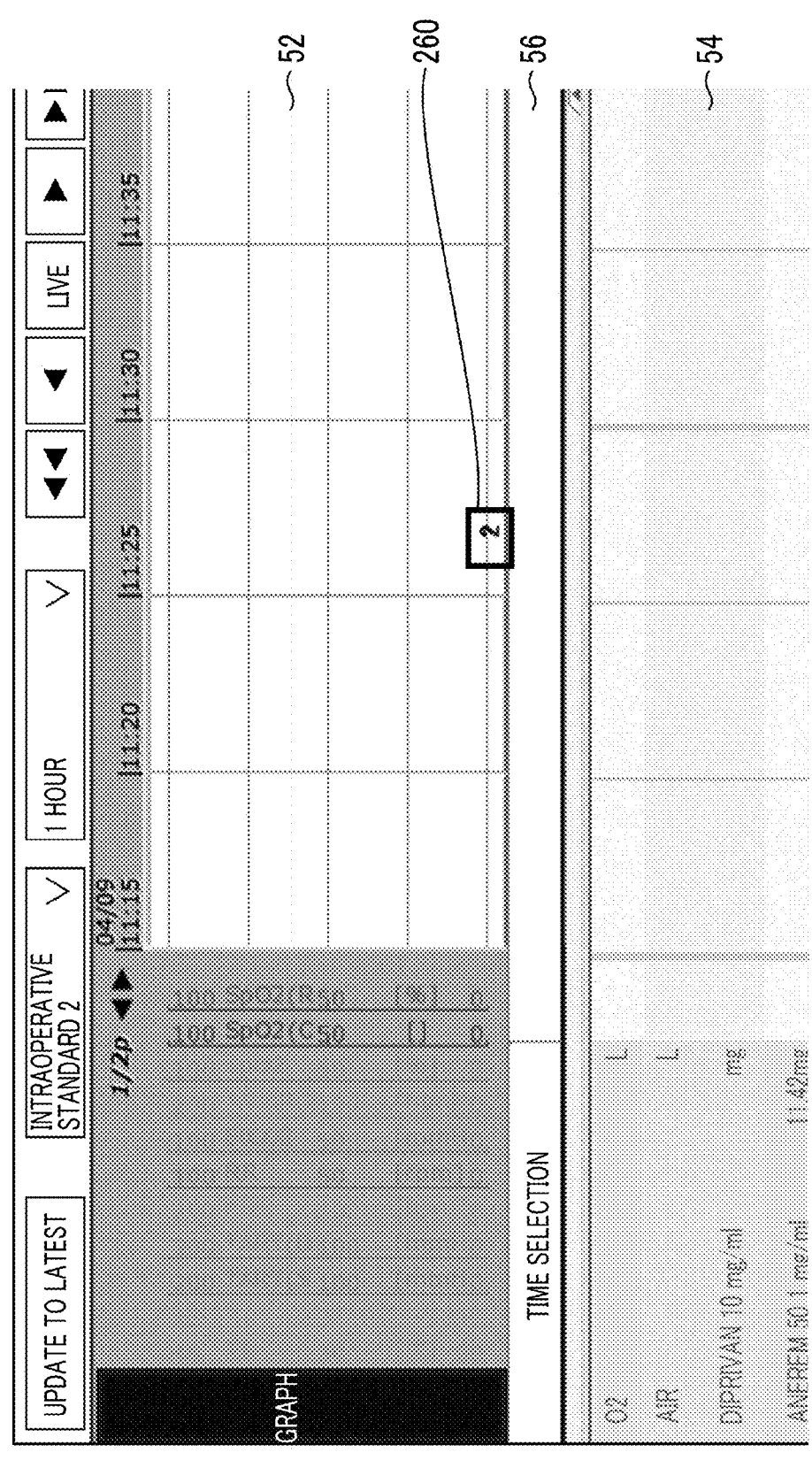
FIG. 36 is a display example of the supplementary information display field in a case where the remarks information is registered.

FIG. 36 shows a display example of the supplementary information display field 56 in a state in which the remarks information is registered with the procedure 5C. In this example, a symbol "2" representing a registration number (remarks number) of the remarks information is displayed in a region 260 corresponding to a position of a target time in the supplementary information display field 56. In a case where the symbol "2" indicating the remarks number is clicked or the mouse is placed over the symbol "2", a setting sentence (the content of remarks) associated with the symbol is displayed.

Function Capable of Selecting Registered Record and Adding Registered Record to Pallet The medical information management system 10 has a function capable of selecting a record registered with a manual input without using the pallet, on the region of the recording information display field 58 and adding the registered record to the pallet of the input list 60. For example, as described referring to FIGS. 31 to 36, the record registered with a manual input without using the pallet is "right-clicked", on the recording information display field 58 and an item "add to pallet" is clicked from a right-click menu, whereby an input item can be added to the pallet.

Figure 37:
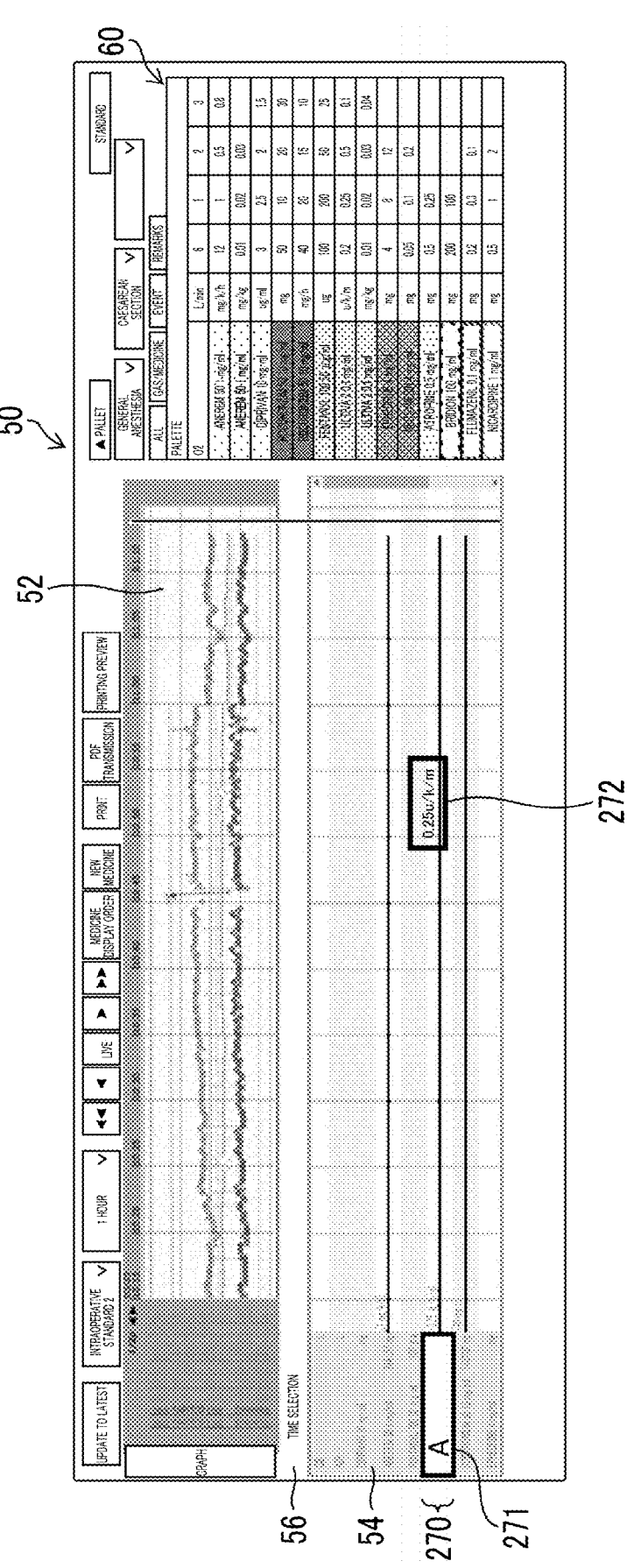
FIG. 37 is a screen example showing an example of an operation to add information regarding a medicine registered in the administration information display field to the input list.

FIG. 37 is a screen example showing an example of an operation to add information regarding a medicine recorded in the administration information display field 54 to the input list 60. It is assumed that, for example, information regarding a medicine name "A" displayed in a medicine row 270 of a medicine having a name "A" from among a plurality of medicines shown in the column of the medicine name in the administration information display field 54 shown in FIG. 37 and a dose "0.25 μ/k/m" is registered with a manual input without using the pallet (input list 60).

Figure 38:
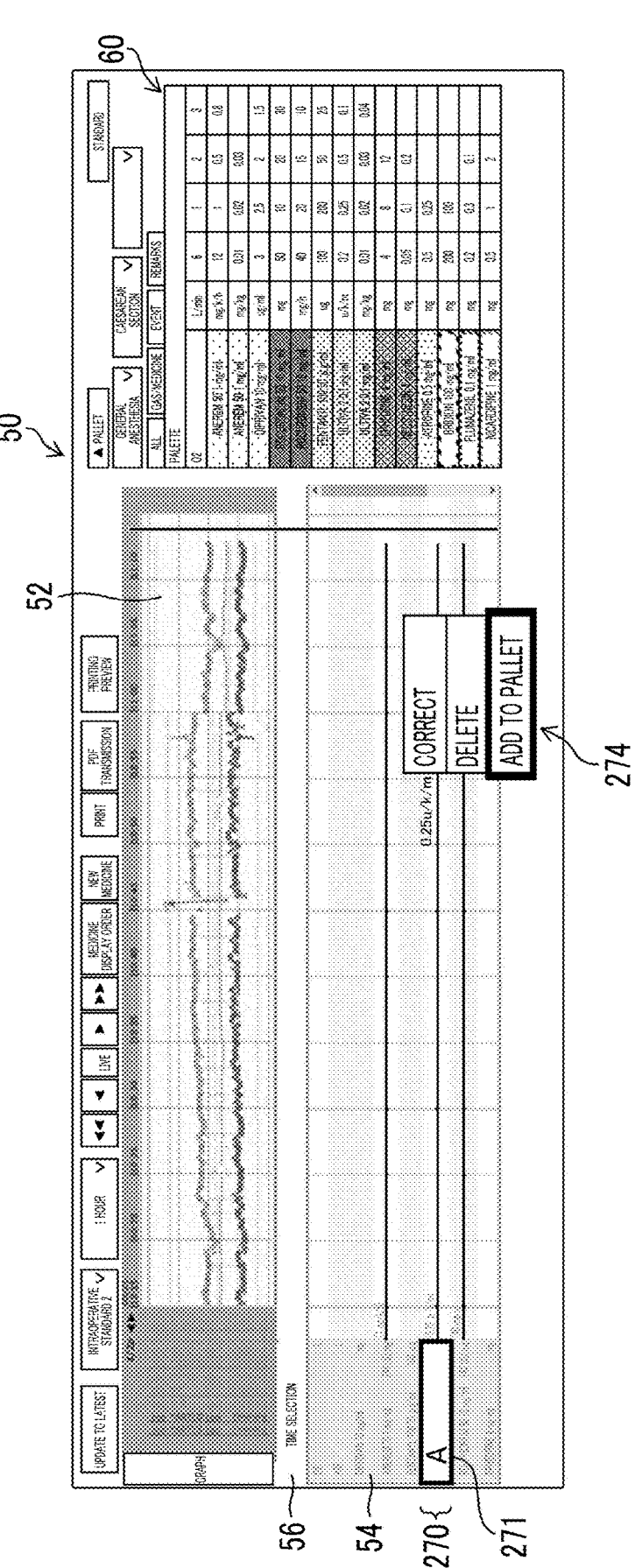
FIG. 38 is a display example in a case where a right click is made in a display region of a dose on the administration information display field.

In a case where the user selects a display region 271 of the medicine name "A" or a display region 272 of a numerical value "0.25 μ/k/m" of a dose in the medicine row 270 of the medicine "A" in the administration information display field 54 and performs a right-click operation, a right-click menu 274 shown in FIG. 38 is displayed.

FIG. 38 is a display example of a case where the user right-clicks on the display region 272 of the dose. In a case where the user selects the item "add to pallet" from the right-click menu 274, as shown in FIG. 39, a new row of the medicine "A" is added to the input list 60, and an item of the dose "0.25" is added.

The operation is not limited to the right-click operation, and the same processing may be executed by an operation of drag-and-drop. For example, in a case where the display region 272 of the dose is dragged and moved to the display region of the input list 60 and is dropped on the input list 60, as shown in FIG. 39, the new row of the medicine "A" is added to the input list 60, and the item of the dose "0.25" is added. The drag in this case includes a concept of designating a medicine and a dose on the administration information display field 54. The drop to the input list 60 includes a concept of designating a region in the input list 60.

It is possible to simply add an input item to a pallet with such a two-click operation or the drag-and-drop operation. With this function, it is possible to make the pallet grow while creating an administration record without starting the maintenance function.

Figure 39:
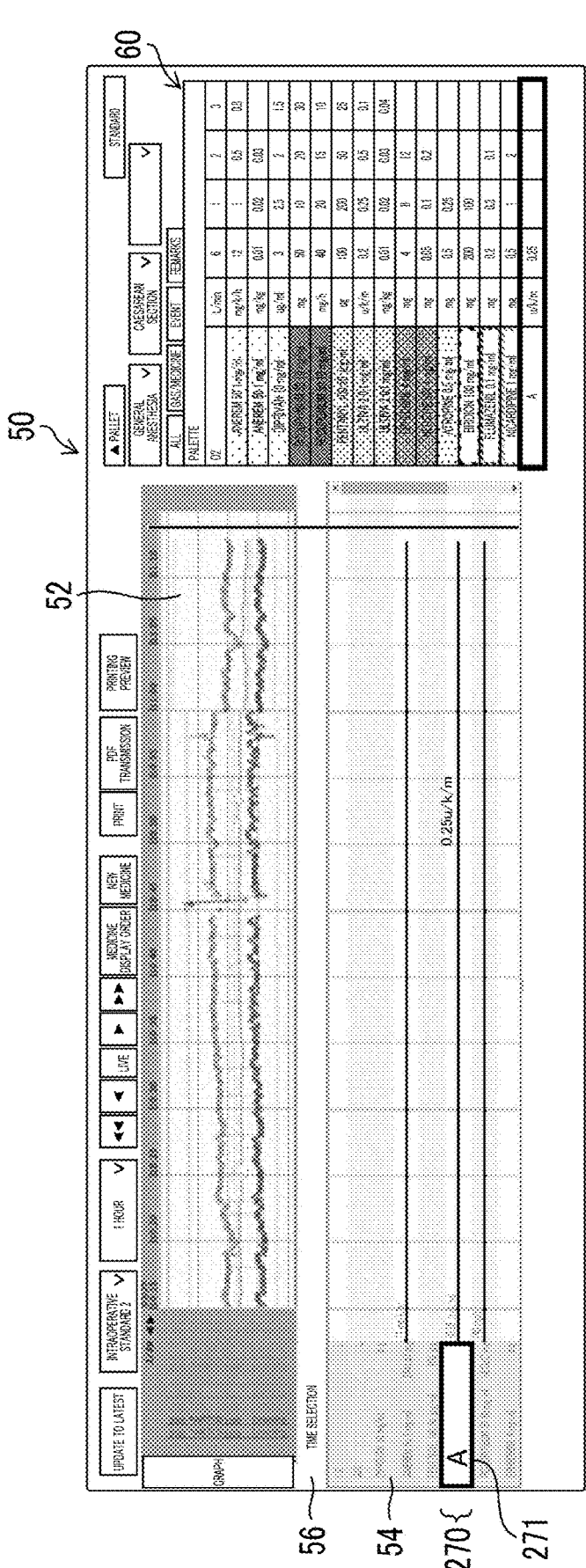
FIG. 39 is a display example showing a state in which a medicine pallet is added to the input list.

In FIGS. 37 to 39, although an example where the input items of the medicine and the dose are added to the pallet has been described, an event and/or remarks recorded in the supplementary information display field 56 can also be added to the pallet with the same operation.

Configuration Example of Medical Information Management System 10

Figure 40:
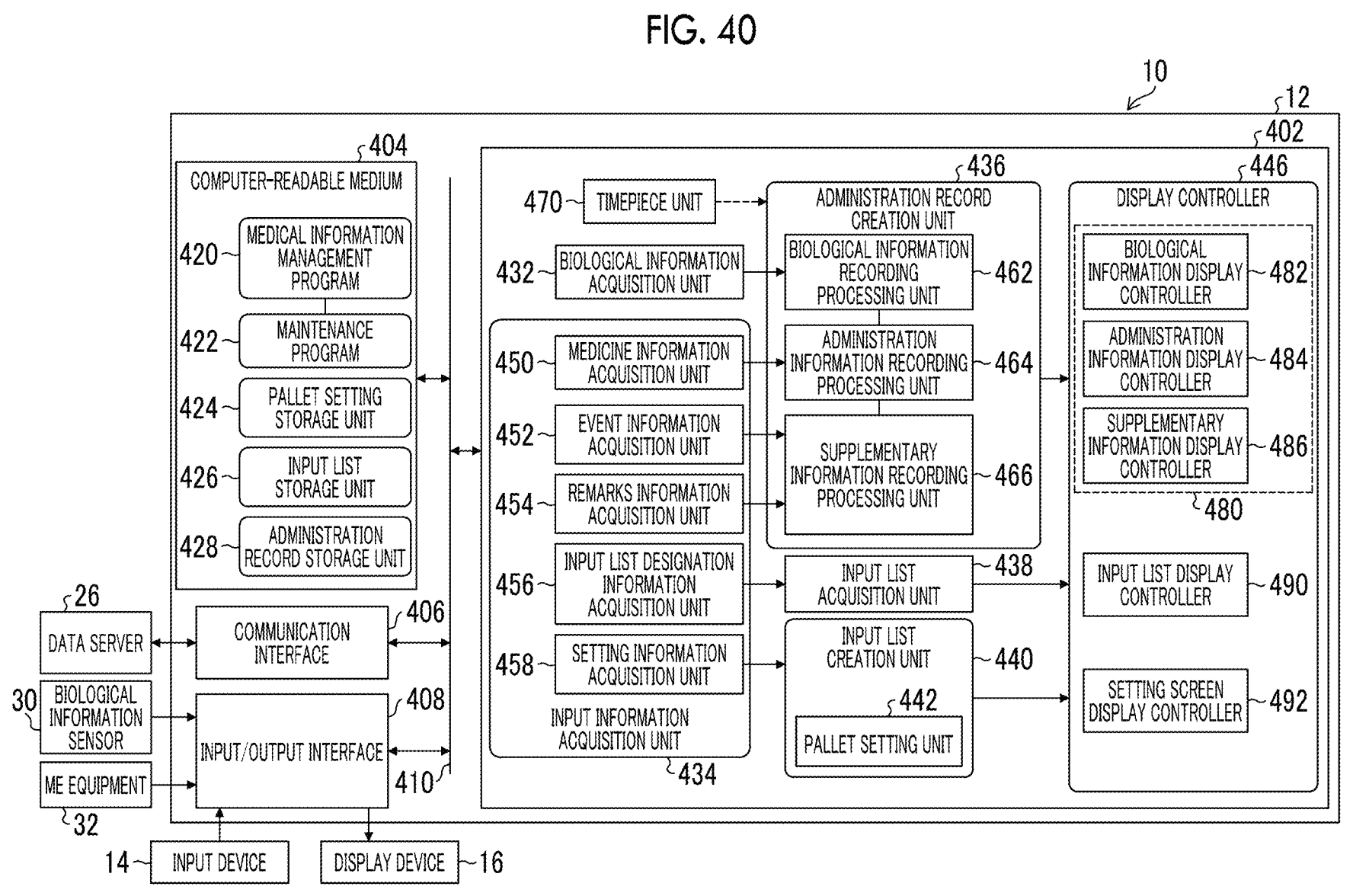

FIG. 40 is a block diagram showing a configuration example of the medical information management system 10 according to the embodiment. The information processing apparatus 12 that is used for the medical information management system 10 comprises a processor 402, a computer readable medium 404 that is a non-transitory tangible thing, a communication interface 406, and an input/output interface 408.

The processor 402 includes a central processing unit (CPU). The processor 402 may include a graphics processing unit (GPU). The processor 402 is connected to the computer readable medium 404, the communication interface 406, and the input/output interface 408 through a bus 410. The input device 14 and the display device 16 are connected to the processor 402 through the input/output interface 408. The biological information sensors 30 and the ME equipment 32 are connected to the processor 402 through the input/output interface 408.

The communication interface 406 is an interface that executes communication processing with an external apparatus in a wired or wireless manner and exchanges information with the external apparatus. The information processing apparatus 12 is connected to the communication line 22 through the communication interface 406 (see FIG. 1), and is connected to the data server 26 on a network in the medical institution and an external apparatus, such as other terminals, in a communicable manner.

The communication interface 406 can take a role as an information acquisition unit that receives an input of data to be processed, a processing request, and the like. The communication interface 406 can also take a role as an information output unit that outputs a processing result and the like of the information processing apparatus 12.

The computer readable medium 404 includes a memory as a main storage device and a storage as an auxiliary storage device. The computer readable medium 404 may be, for example, a semiconductor memory, a hard disk drive (HDD) device, a solid state drive (SSD) device, or a combination of a plurality of such devices. The computer readable medium 404 is an example of a "storage device" in the present disclosure.

In the computer readable medium 404, a plurality of programs including a medical information management program 420, a maintenance program 422, and a display control program (not shown), data, and the like are stored. The computer readable medium 404 includes a pallet setting storage unit 424, an input list storage unit 426, and an administration record storage unit 428. The pallet setting storage unit 424 stores setting information regarding the pallet of the input list 60 set using the maintenance program 422. The input list storage unit 426 stores data of the input list 60 including a plurality of registered pallet item patterns. The administration record storage unit 428 stores data of the administration record created using the medical information management program 420.

The processor 402 reads out the programs stored in the computer readable medium 404 and executes various kinds of processing in response to commands of the programs. The programs stored in the storage are loaded to the memory, and the processor 402 executes the programs, whereby the information processing apparatus 12 functions as means for executing various kinds of processing specified in the programs.

That is, the processor 402 executes the programs, such as the medical information management program 420 and the maintenance program 422, to function as a biological information acquisition unit 432, an input information acquisition unit 434, an administration record creation unit 436, an input list acquisition unit 438, an input list creation unit 440, and a display controller 446.

The biological information acquisition unit 432 receives an input of biological information from the biological information sensors 30 and acquires the biological information. The biological information acquisition unit 432 may acquire the biological information from the data server 26.

The input information acquisition unit 434 receives an input of various kinds of information from the input device 14 and sends commands, information, and the like to corresponding processing units depending on the contents of information input through the input device 14. The input information acquisition unit 434 includes a medicine information acquisition unit 450, an event information acquisition unit 452, a remarks information acquisition unit 454, an input list designation information acquisition unit 456, and a setting information acquisition unit 458.

The medicine information acquisition unit 450 acquires medicine information input with a drag-and-drop operation using the input list 60 or an operation of a manual input. Similarly, the event information acquisition unit 452 and the remarks information acquisition unit 454 acquire event information and remarks information input with a drag-and-drop operation using the input list 60 or an operation of a manual input, respectively.

The input list designation information acquisition unit 456 receives an input of information for designating a pallet item pattern to be displayed as the input list 60. The input list designation information acquisition unit 456 may acquire designation information of a pallet item pattern associated with selection of an operation flow or may acquire designation information of a pallet item pattern corresponding to a tab designated by a user's operation from the input device 14. The input list acquisition unit 438 reads out data of the corresponding input list 60 from the input list storage unit 426 based on the designation information acquired through the input list designation information acquisition unit 456.

The setting information acquisition unit 458 acquires information regarding various kinds of settings using the maintenance function and the like. The input list creation unit 440 creates the input list 60 based on the setting information acquired through the setting information acquisition unit 458. The input list creation unit 440 includes a pallet setting unit 442, and the pallet setting unit 442 executes processing regarding setting of the pallet, such as registration of pallet items and registration of a pallet item pattern. Pallet setting information set by the pallet setting unit 442 is stored in the pallet setting storage unit 424.

The processor 402 receives an input of setting including at least one instruction of change, addition, or deletion for at least one item of a medicine or a dose of each medicine displayed in the input list 60 from the user on the maintenance screen 90, and displays the pallet including a plurality of medicine regions 62 in the input list 60 depending on the setting.

The administration record creation unit 436 creates an administration record represented the anesthesia record illustrated in FIG. 3. The administration record creation unit 436 includes a biological information recording processing unit 462, an administration information recording processing unit 464, and a supplementary information recording processing unit 466. The biological information recording processing unit 462 executes processing of recording the biological information acquired through the biological information acquisition unit 432. The biological information recording processing unit 462 includes a processing function of graphing the time-series biological information by item of the biological information.

The administration information recording processing unit 464 executes processing of recording the administration information including the medicine information and the administration timing of the medicine acquired through the medicine information acquisition unit 450. The supplementary information recording processing unit 466 executes processing of recording the supplementary information acquired through the event information acquisition unit 452 or the remarks information acquisition unit 454. The biological information recording processing unit 462, the administration information recording processing unit 464, and the supplementary information recording processing unit 466 record the information items in association with a common time axis.

The processor 402 comprises a timepiece unit 470, and the timepiece unit 470 generates date and time information including date and a current time. Date, the current time, a time range (period), and the like recognized by the timepiece unit 470, and information input through the biological information acquisition unit 432 and the input information acquisition unit 434 can be managed in time series.

The display controller 446 executes processing of generating data for display to be displayed on the display device 16. The display controller 446 includes a recording information display controller 480, an input list display controller 490, and a setting screen display controller 492. The recording information display controller 480 generates data for display to be displayed in the recording information display field 58 described referring to FIG. 3 and controls the display of the recording information display field 58.

The recording information display controller 480 includes a biological information display controller 482, an administration information display controller 484, and a supplementary information display controller 486. The biological information display controller 482 generates data for display including the biological information for performing the display of the biological information display field 52. The administration information display controller 484 generates data for display including administration information for performing the display of the administration information display field 54. The supplementary information display controller 486 generates data for display including the supplementary information for performing the display of the supplementary information display field 56.

The input list display controller 490 generates data for display for performing the display of the input list 60 and controls the display of the input list 60.

The setting screen display controller 492 generates data for display for performing the display of various setting screens and controls the display of the setting screens.

The functions and the operation of the medical information management system 10 are as described above. A method of creating the administration record and managing medical information with the medical information management system 10 is an example of a medical information management method in the present disclosure.

Program that Operates Computer

A program that causes a computer to realize a part or the whole of at least one function among various processing functions in the medical information management system 10 described in the above-described embodiment can be recorded on a computer readable medium that is a tangible non-transitory information storage medium, such as an optical disc, a magnetic disk, or a semiconductor memory, and the program can be provided through the information storage medium.

Instead of the aspect where the program is stored in such a non-transitory computer readable medium and provided, a program signal can be provided as a download service using a communication line, such as the Internet.

A part or all of the processing functions of the medical information management system 10 may be realized by cloud computing and can be provided as a cloud service of software as a service (SaaS).

Hardware Configuration of Each Processing Unit

The hardware structures of processing units that execute various kinds of processing, such as the biological information acquisition unit 432, the input information acquisition unit 434, the administration record creation unit 436, the input list acquisition unit 438, the input list creation unit 440, and the display controller 446 in the medical information management system 10, are, for example, various processors described below.

Various processors include a CPU that is a general-purpose processor executes a program to function as various processing units, a GPU that is a processor specialized for image processing, a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like.

One processing unit may be configured of one of various processors described above or may be configured of a combination of two or more processors of the same type or different types. For example, one processing unit may be configured of a plurality of FPGAs, a combination of a CPU and an FPGA, or a combination of a CPU and a GPU. A plurality of processing units may be configured of one processor. As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that realizes all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined.

Advantages of the Embodiment (1) With the medical information management system 10 according to the embodiment, the input of dragging and dropping the medicine region 62 on the input list 60 to the region of the recording information display field 58 is received, and the administration information of the administration information display field 54 is updated reflecting the drag-and-drop input. With this, it is possible to simplify user's input work of the administration information.

(2) Since the medicine region 62 of the input list 60 can be dragged and dropped to the region of the biological information display field 52, it is possible to record the administration information at a place of an appropriate time on the time axis while confirming transition over time of the biological information. Similarly, since the supplementary region 64 of the input list 60 can be dragged and dropped to the region of the biological information display field 52, it is possible to record the supplementary information at a place of an appropriate time on the time axis while confirming transition over time of the biological information.

(3) Since it is possible to simply display the dose in a unit different from the unit of the dose displayed in the input list 60, it is possible to allow the user to confirm the dose in a plurality of units in a case of inputting data.

(4) In regard to the display of the input list 60, since various kinds of differentiation display can be set, it is possible to increase visibility.

(5) It is possible to switch the display of the input list 60 depending on the operation flow or the login user, and it is possible to present the input candidates with high convenience.

The advantages (1) to (5) are a part of the advantages of the medical information management system 10. A user interface with high convenience is realized by various functions implemented in the medical information management system 10 according to the embodiment, and the user can create the administration record with a simple operation.

Modification Example

In the above-described embodiment, although the anesthesia record has been described as an example, the technique of the present disclosures is not limited to anesthesia, and can be applied for the purpose of creating administration records for various medicine types. In the anesthesia recording screen 50 illustrated in FIG. 3, although an example where the biological information, the administration information, and the supplementary information are recorded has been described, a form in which the function of recording and displaying the supplementary information is omitted may be made depending on the purposes.
Others The embodiments of the present disclosure described above can appropriately change, add, or delete configurations without departing from the spirit and scope of the present disclosure. The present invention is not limited to the above-described embodiments and may be modified in various ways by those skilled in the art within the technical scope and spirit of the present invention.
Explanation of References
    10: medical information management system
    12: information processing apparatus
    14: input device
    16: display device
    20: medical information system
    22: communication line
    24: patient information management system
    26: data server
    30: biological information sensor
    32: anesthesia machine
    40: application screen
    41: patient information display field
    42: navigation bar
    43: anesthesia record button
    44: login screen
    46: OK button
    50: anesthesia recording screen
    51: user name display field
    52: biological information display field
    54: administration information display field
    56: supplementary information display field
    58: recording information display field
    59: line segment
    60: input list
    62, 62*a*, 62*b*: medicine region
    63: medicine list
    63*a*: medicine type cell
    63*b*: unit cell
    63*c*: dose cell
    64: supplementary region
    65: supplementary list
    66*a*, 66*b*, 66*c*: combo box
    70: region
    71: line segment
    72: time information
    73: medicine information
    80: pop-up
    84: unit region
    86: pull-down menu
    87: region
    90: maintenance screen
    92: sorting tab

32

93: item
    96: detailed setting screen
    97: add button
    98: new button
    99: pattern list display field
    100: registration screen
    102: name input field
    104: explanation input field
    106: check box
    108: register button
    110: detailed setting screen
    112: pallet item list display field
    114: add button
    120: classification selection screen
    122: OK button
    130: flow-specific pattern setting screen
    132: flow-specific pattern set button
    134: flow set button
    140: flow setting screen
    142: OK button
    150: flow-specific pattern registration screen
    152: input field
    154: select button
    156: register button
    160: pattern setting screen
    162: OK button
    171, 172, 173, 174: tab
    176: scroll bar
    180: pallet item registration screen
    182: name input field
    184: add button
    186: pallet item display field
    190: set region
    194: line
    200: time designation menu
    201: time display field
    202, 203: adjust button
    204: OK button
    206: cancel button
    210: administration information input screen
    212: medicine name input field
    213: change button
    214: administration method selection field
    216: dose input field
    218: OK button
    220: time designation menu
    224: event button
    225: remarks button
    230: event input screen
    232: classification selection field
    234: event selection field
    236: select button
    240: confirmation screen
    242: OK button
    244: mark
    250: remarks input screen
    252: setting sentence display field
    254: classification selection field
    256: template selection field
    258: OK button
    270: medicine row
    271: display region
    272: display region
    274: right-click menu
    402: processor
    404: computer readable medium
    406: communication interface 408: input/output interface
410: bus
420: medical information management program
422: maintenance program
424: pallet setting storage unit
426: input list storage unit
428: administration record storage unit
432: biological information acquisition unit
434: input information acquisition unit
436: administration record creation unit
438: input list acquisition unit
440: input list creation unit
442: pallet setting unit
446: display controller
450: medicine information acquisition unit
452: event information acquisition unit
454: remarks information acquisition unit
456: input list designation information acquisition unit
458: setting information acquisition unit
462: biological information recording processing unit
464: administration information recording processing unit
466: supplementary information recording processing unit
470: timepiece unit
480: recording information display controller
482: biological information display controller
484: administration information display controller
486: supplementary information display controller
490: input list display controller
492: setting screen display controller
PLA, PLB, PL1, PL2, PL3, PL4, PL5: medicine pallet row

What is claimed is:

1. A medical information management system comprising:

a processor; and
a storage device in which a program that is executed by the processor is stored,
wherein the processor is configured to execute the program to:
display a display field having a biological information display field where biological information of a target patient is displayed along a time axis and an administration information display field where administration information including information regarding an administered medicine, a dose, and an administration timing to the target patient in a period corresponding to a display range of the time axis of the biological information display field is displayed, and an input list where a plurality of medicine regions in correlation with combination information of a plurality of medicines and doses are arranged;
in response to an input of dragging a first region from among the plurality of medicine regions of the input list, read out medicine information that corresponds to the first region being dragged from the storage device, wherein the read medicine information is a first medicine and a first dose correlated with the first region; and
in response to an input of dropping the first region to a second region of the biological information display field,
determine a drop position within the second region, wherein the drop position is at which the input of dropping the first region is performed, determine a first time point on the time axis closest to the drop position in the second region in the biological information display field,
add the information indicating that the first medicine and the first dose correlated with the first region is administered to the target patient at the first time point, to update and store the administration information in the storage device, and
update the display of the administration information display field based on the updated administration information such that the information indicating the first medicine and the first dose correlated with the first region is displayed at the drop position of the second region of the biological information display field.

2. The medical information management system according to claim 1,
wherein the processor is configured to display a line segment perpendicular to the time axis,
wherein the line segment is displayed at the drop position, and
wherein the first time point on the time axis is an intersection of the line segment and the time axis.

3. The medical information management system according to claim 1,
wherein, in the first region on the input list, the first dose is indicated by a numerical value in a first unit, and
the processor is configured to display a second dose indicated by a numerical value in a second unit different from the first unit in a case where the first region is designated on the input list.

4. The medical information management system according to claim 1,
wherein the processor is configured to change a display format of characters of a medicine and a dose in the input list depending on a type of the medicine or an administration method.

5. The medical information management system according to claim 1,
wherein the processor is configured to receive an input of display setting including an instruction for display of a part of a plurality of medicines and doses of the medicines displayed in the input list in a different display format, and display the part of the input list in the different display format based on the display setting.

6. The medical information management system according to claim 1,
wherein the processor is configured to receive an input of setting including an instruction for at least one of change, addition, or deletion regarding at least one item among medicines and doses of the medicines displayed in the input list, and display the plurality of medicine regions in the input list depending on the setting.

7. The medical information management system according to claim 1,
wherein the processor is configured to have a plurality of list patterns in which at least one of a medicine or a dose displayed in the input list is different, receive an input of designating a list pattern for use from the plurality of list patterns, and display the plurality of medicine regions indicating input candidates of medicines and doses corresponding to the designated list pattern in the input list.

8. The medical information management system according to claim 7, wherein at least one of the plurality of list patterns is correlated with a type of an operation or a user, and an input of designating the type of the operation or the user is performed to designate the list pattern for use.

9. The medical information management system according to claim 1, wherein at least one medicine region among the plurality of medicine regions in the input list is in correlation with a set of information including a plurality of medicines and doses of the medicines.

10. The medical information management system according to claim 1, wherein the biological information display field further has a supplementary information display field where supplementary information regarding a matter within the period of the display range is displayed, the input list includes a plurality of supplementary regions in correlation with a plurality of supplementary items to be input candidates, and the processor is configured to receive an input of dragging a third region from the plurality of supplementary regions of the input list and dropping the third region to a fourth region of the biological information display field, add information indicating that a matter of a supplementary item correlated with the third region is executed at a time corresponding to a position of the fourth region of the biological information display field, to update the supplementary information in a case where the input of dragging the third region and dropping the third region to the fourth region is received, and update display of the supplementary information display field based on the updated supplementary information.

11. The medical information management system according to claim 10, wherein the supplementary information includes at least one of event information or remarks information, the plurality of supplementary items include at least one of an event item or a remarks item, and the plurality of supplementary regions include at least one of an event region in correlation with the event item or a remarks region in correlation with the remarks item.

12. The medical information management system according to claim 10, wherein the processor is configured to receive an input of setting including an instruction for at least one of change, addition, or deletion regarding at least one item among medicines, doses of the medicines, and a supplementary item displayed in the input list, and display the plurality of medicine regions and the plurality of supplementary regions in the input list depending on the setting.

13. The medical information management system according to claim 10, wherein the processor is configured to have a plurality of list patterns in which at least one of a medicine, a dose of each medicine, or a supplementary item displayed in the input list is different, receive an input of designating a list pattern for use from the plurality of list patterns, and display the plurality of medicine regions and the plurality of supplementary regions indicating input candidates of medicines, doses of the medicines, and supplementary items corresponding to the designated list pattern in the input list.

14. The medical information management system according to claim 12, wherein the input list includes a set region in correlation with a set of information regarding a supplementary item, a medicine, and a dose, and the processor is configured to receive an input of dragging the set region of the input list and dropping the set region to a fifth region of the biological information display field, add a record indicating that a matter of a supplementary item correlated with the set region is executed at a time corresponding to a position of the fifth region of the biological information display field, to update the supplementary information and add information indicating that a medicine and a dose correlated with the set region are administered to the target patient, to update the administration information in a case where the input of dragging the set region and dropping the set region to the fifth region of the biological information display field is received, and update the display of the supplementary information display field based on the updated supplementary information and update the display of the administration information display field based on the updated administration information.

15. The medical information management system according to claim 1, wherein the processor is configured to acquire the biological information of the target patient from at least one of a biological information sensor or a data server, and display a graph of the acquired biological information in the biological information display field.

16. The medical information management system according to claim 1, further comprising:

a display device that displays the biological information display field and the input list; and an input device that receives an operation of drag-and-drop.

17. A medical information management method that is executed by a computer, the medical information management method comprising:

at the computer, acquiring biological information of a target patient;

displaying, on a display device, a display field having a biological information display field where the acquired biological information is displayed along a time axis and a administration information display field where administration information including information regarding an administered medicine, a dose, and an administration timing to the target patient in a period corresponding to a display range of the time axis of the biological information display field is displayed, and an input list where a plurality of medicine regions in correlation with combination information of a plurality of medicines and doses are arranged;

in response to an input of dragging a first region from among the plurality of medicine regions of the input list, reading out medicine information that corresponds to the first region being dragged from a storage device, wherein the read medicine information is a first medicine and a first dose correlated with the first region; and in response to an input of dropping the first region to a second region of the biological information display field, determining a drop position within the second region, wherein the drop position is at which the input of dropping the first region is performed, determining a first time point on the time axis closest to the drop position in the second region in the biological information display field, adding the information indicating that the first medicine and the first dose correlated with the first region is administered to the target patient at the first time point, to update and store the administration information in the storage device, and updating the display of the administration information display field based on the updated administration information such that the information indicating the first medicine and the first dose correlated with the first region is displayed at the drop position of the second region of the biological information display field.

18. A non-transitory computer recording medium storing a program that causes a computer to realize:

displaying a display field having a biological information display field where biological information of a target patient is displayed along a time axis and an administration information display field where administration information including information regarding an administered medicine, a dose, and an administration timing to the target patient in a period corresponding to a display range of the time axis of the biological information display field is displayed, and an input list where a plurality of medicine regions in correlation with combination information of a plurality of medicines and doses are arranged;

in response to an input of dragging a first region from among the plurality of medicine regions of the input list, read out medicine information that corresponds to the first region being dragged from a storage device, wherein the read medicine information is a first medicine and a first dose correlated with the first region; and in response to an input of dropping the first region to a second region of the biological information display field, determining a drop position within the second region, wherein the drop position is at which the input of dropping the first region is performed, determining a first time point on the time axis corresponding closest to the drop position in the second region in the biological information display field, adding the information indicating that the first medicine and the first dose correlated with the first region is administered to the target patient at the first time point, to update and store the administration information in the storage device, and updating the display of the administration information display field based on the updated administration information such that the information indicating the first medicine and the first dose correlated with the first region is displayed at the drop position of the second region of the biological information display field.

* * * * *